(12) United States Patent
Schulz-Raffelt et al.

(10) Patent No.: US 10,513,680 B2
(45) Date of Patent: Dec. 24, 2019

(54) GREEN MICROALGAE LACKING A FUNCTIONAL DYRKP-1 GENE, FOR USE FOR INCREASED PRODUCTION OF FEEDSTOCK

(71) Applicant: COMMISSARIAT A L'ENERGIE ATOMIQUE ET AUX ENERGIES ALTERNATIVES, Paris (FR)

(72) Inventors: Miriam Schulz-Raffelt, Puyricard (FR); Vincent Chochois, Canberra (AU); Yonghua Li-Beisson, Aix-en-Provence (FR); Gilles Peltier, Pierrevert (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 181 days.

(21) Appl. No.: 15/308,341

(22) PCT Filed: May 7, 2015

(86) PCT No.: PCT/IB2015/053349
§ 371 (c)(1),
(2) Date: Nov. 1, 2016

(87) PCT Pub. No.: WO2015/170280
PCT Pub. Date: Nov. 12, 2015

(65) Prior Publication Data
US 2017/0058254 A1    Mar. 2, 2017

(30) Foreign Application Priority Data
May 7, 2014 (EP) .................................. 14305673

(51) Int. Cl.
*C12N 1/12* (2006.01)
*C12P 19/04* (2006.01)
*C12N 9/12* (2006.01)
*C12P 7/64* (2006.01)

(52) U.S. Cl.
CPC ........ *C12N 1/12* (2013.01); *C12Y 207/12001* (2013.01); *C12N 9/12* (2013.01); *C12P 7/6463* (2013.01); *C12P 19/04* (2013.01); *Y02E 50/17* (2013.01)

(58) Field of Classification Search
None
See application file for complete search history.

(56) References Cited

U.S. PATENT DOCUMENTS

2016/0273061 A1*  9/2016  Hayakawa ............... C12N 1/12

OTHER PUBLICATIONS

Friedberg, Automated protein function prediction—the genomic challenge. Brief. Bioinformatics. 7:225-242, 2006.*
Merchant et al, The Chlamydomonas genome reveals the evolution of key animal and plant functions. Science 318 (5848), 245-250, 2007.*
Aranda et al, DYRK family of protein kinases: evolutionary relationships, biochemical properties, and functional roles. FASEB Journal. 25, 449-462, 2011.*
Goodson et al, Structural Correlates of Cytoplasmic and Chloroplast Lipid Body Synthesis in Chlamydomonas reinhardtii and Stimulation of Lipid Body Production with Acetate Boost. Eukaryotic Cell, p. 1592-1606, 2011.*
Wilson et al, Regulation of glycogen metabolism in yeast and bacteria. FEMS Microbiol Rev 34, 952-985, 2010.*
Boyle et al (Three Acyltransferases and Nitrogen-responsive Regulator Are Implicated in Nitrogen Starvation-induced Triacylglycerol Accumulation in Chlamydomonas. The Journal of Biological Chemistry vol. 287, No. 19, pp. 15811-15825, May 4, 2012). (Year: 2012).*
Asamizu, E., et al., "Generation of Expressed Sequence Tags From Low-$CO_2$ and High-$CO_2$ Adapted Cells of Chlamydomonas reinhardtii," DNA Research 7(5):305-307, Jan. 2000.
Chochois, V., et al., "Relationships Between PSII-Independent Hydrogen Bioproduction and Starch Metabolism as Evidenced From Isolation of Starch Catabolism Mutants in the Green Alga *Chlamydomonas reinhardtii*," International Journal of Hydrogen Energy 35(19):10731-10740, Apr. 2010.
Goodson, C., et al., "Structural Correlates of Cytoplasmic and Chloroplast Lipid Body Synthesis in Chlamydomonas reinhardtii and Stimulation of Lipid Body Production With Acetate Boost," Eukaryotic Cell 10(12):1592-1606, Dec. 2011.
Han, J., et al., "Deep Evolutionary Conservation of an Intramolecular Protein Kinase Activation Mechanism," PLoS ONE 7(1):e29702, Jan. 2012, 9 pages.
International Search Report dated Aug. 3, 2015, issued in corresponding International Application No. PCT/IB2015/053349, filed May 7, 2015, 5 pages.
Karpov, P.A., et al., "Identification of Plant Homologues of Dual Specificity Yak1-Related Kinase 1A," Proceedings of the International Moscow Conference on Computational Molecular Biology (MCCMB '11), Moscow, Jul. 21-24, 2011, pp. 148-149.
Larkum, A.W.D., et al., "Selection, Breeding and Engineering of Microalgae for Bioenergy and Biofuel Production," Trends in Biotechnology 30(4):198-205, Apr. 2012.
Wilson, W.A., et al., "Regulation of Glycogen Metabolism in Yeast and Bacteria," FEMS Microbiology Reviews 34(6):952-985, Nov. 2010.
Written Opinion dated Aug. 3, 2015, issued in corresponding International Application No. PCT/IB2015/053349, filed May 7, 2015, 6 pages.

* cited by examiner

*Primary Examiner* — Medina A Ibrahim
*Assistant Examiner* — Wayne Zhong
(74) *Attorney, Agent, or Firm* — Christensen O'Connor Johnson Kindness PLLC

(57) ABSTRACT

The present invention relates to a method for producing biomass feedstock, by cultivating green microalgae cells in which the expression and/or the activity of the dual-specificity tyrosine-phosphorylation-regulated kinase (DYRKP-1) protein is altered, inducing reserve accumulation and/or increase in biomass production by said microalgae.

11 Claims, 28 Drawing Sheets

Specification includes a Sequence Listing.

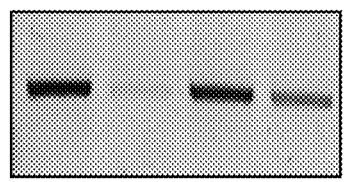
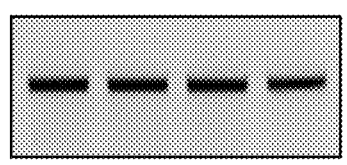
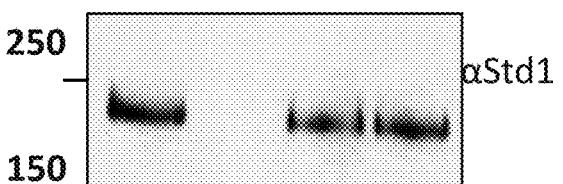
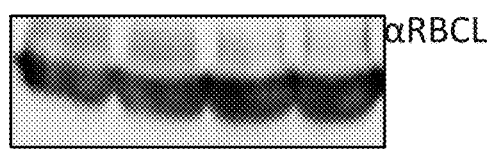
Figure 1C
Figure 1D
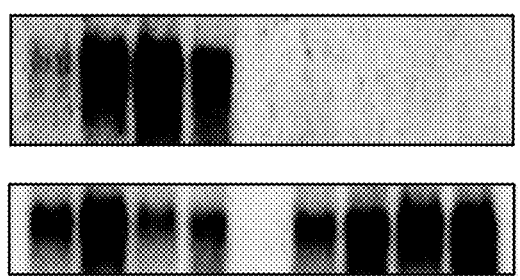
Figure 1E

| Becker and Joost, 1999 | N | X | G | Y/F | D | D | D/E | N | X | D | Y | X | X | X | X | D/E |
|---|---|---|---|---|---|---|---|---|---|---|---|---|---|---|---|---|
| DYRK1 | N | D/H | G | Y | D | D | D | N | H/Y | D | Y | I | K/R | N/S | G | E |
| DYRK2 | N | X | G | Y | D | D | D/E | R | G | D/S | Y | X | V | P/L | H/G/R | D |
| YAK1 | N | D/N | G | X | D | N | E | N | X | D | Y/L | I | X | V | N | D/X |
| DYRKP-A | N | R | T | G | F | E | E | D/E | K | N/D | F | N/P/N | V | L | N | S/A |
| DYRKP-B | N | R | T | G | F | E | E | N | K | D/E | F/L | P | V | X | N | S/T |
| DYRKP-algae | H | R/K | T | G | F | E | E | S | K | D/E | F | P | R | # | G | D | days in MM-N/CO$_2$

GREEN MICROALGAE LACKING A FUNCTIONAL DYRKP-1 GENE, FOR USE FOR INCREASED PRODUCTION OF FEEDSTOCK

STATEMENT REGARDING SEQUENCE LISTING

The sequence listing associated with this application is provided in text format in lieu of a paper copy and is hereby incorporated by reference into the specification. The name of the text file containing the sequence listing is 57068_Seq_Revised Final_2019-10-23.txt. The text file is 27 KB; was created on Oct. 23, 2019; and is being submitted via DFS-Web with the filing of the specification.

BACKGROUND

The present invention relates to the field of green microalgae and their use in biotechnology. More particularly, the present invention describes the use of *Chlamydomonas* lacking a functional DYRKP-1 protein, for producing large amounts of neutral lipids (triacylglycerides: TAGs, or oils) and/or large amounts of starch, under stress conditions.

Because of their high biomass productivity and their ability to accumulate high intracellular amounts of starch (convertible into bioethanol), or oil (convertible into biodiesel), microalgae represent a promising feedstock for the production of next-generation biofuels (Hu et al., 2008; Wijffels and Barbosa, 2010). However, their productivity needs to be increased in order to reach sustainable biofuel production (Delrue et al., 2013).

Microalgae and, more generally, photosynthetic organisms have developed sophisticated strategies to optimize growth and survival under constantly fluctuating conditions of light, temperature and nutrient availability. In microalgae, deprivation of essential macronutrients strongly affects growth and induces drastic changes in the cellular metabolism. A general response to nitrogen or sulfur deprivation consists in a decrease in protein synthesis, an arrest in cell division, a massive accumulation of energy-rich storage compounds such as starch and triacylglycerols (Ball et al., 1990; Merchant et al., 2012), and a down-regulation of photosynthesis (Grossman, 2000; Peltier and Schmidt, 1991). This requirement of nutrient deprivation to trigger accumulation of reserve compounds is one of the major biological limitations of microalgae for biotechnology purposes because it impairs biomass productivity (Hu et al., 2008). Despite considerable interest for microalgae as a new feedstock (Larkum et al., 2012), little is known about signaling and regulatory genes and pathways controlling processes of photosynthetic energy conversion and storage in relation to nutrient and energy status.

Deciphering regulatory mechanisms controlling growth, photosynthesis and reserve accumulation in response to the nutrient and energy status is hence a key issue towards optimizing microalgal productivity for biotechnological applications.

With the aim to unravel regulatory mechanisms involved in the dynamics of reserve in response to nutrient availability, the inventors have now characterized one mutant of *Chlamydomonas reinhardtii*, screened on a defect in starch degradation and called std1 (for starch degradation). The std1 mutant harbors an insertion in a gene of the DYRK family, initially annotated as DYRK2 (*Chlamydomonas* genome version 4.0), and renamed here DYRKP-1. The *Chlamydomonas* std1 mutant, the first dyrk mutant of the green lineage reported so far, accumulates much more starch and oil than its wild-type progenitor in response to nutrient deprivation in photoautotrophic conditions, and more oil than its wild-type progenitor in response to nutrient deprivation also in mixotrophic conditions. The present invention hence provides methods to cultivate microalgae cells so as to optimize their growth for optimum production of starch and/or lipids from the microalgae. The methods of the present invention induce and enhance accumulation of starch and/or oil, depending on the culture conditions, within the microalgae cells. The methods disclosed are suitable for large-scale production of starch- and/or oil-rich microalgae.

A first aspect of the present invention is hence a method for producing biomass feedstock, comprising the steps of:
(i) cultivating green microalgae cells in which the expression and/or the activity of the DYRKP-1 protein is altered; and
(ii) inducing reserve accumulation and/or increase in biomass production by said microalgae.

As defined herein, the "DYRKP-1 protein" is a DYRK protein expressed by microalgae, which possesses a DH-box having the following sequence: H(R/K)TGFEEXK(D/E/N)(F/L) (SEQ ID No: 3). The amino acid sequence and coding sequence (cDNA sequence including the 5'- and 3'-UTRs) of the DYRKP-1 protein of *Chlamydomonas reinhardtii* are disclosed herein (SEQ ID NO: 1 and 2, respectively). From these sequences, the skilled artisan can perfectly identify the sequence of DYRKP-1 in any green microalga different from *Chlamydomonas reinhardtii*, by identifying in said microalga the protein homologous to that of SEQ ID NO: 1. In the present text, a protein is considered as being an homolog of DYRKP-1 from *Chlamydomonas reinhardtii* if both proteins share a common ancestor, as shown by very similar primary sequences (at least 50, 60, 70, 75, 80, 85, 90, 95 or 99% identity, as measured by BLAST) and secondary and tertiary structures.

In the present text, "altered" or "impaired" means that the expression and/or the activity of the DYRKP-1 protein is changed, so that the activity of the protein is decreased. For example, the DYRKP-1 gene can be silenced, knocked down, mutated and/or interrupted, so that the microalgae lack a functional DYRKP-1 protein. Activity of the DYRK-P protein could also be inhibited by chemical compounds acting as specific inhibitors.

As disclosed in the experimental part below, the method according to the invention can be performed with *Chlamydomonas*, especially with *Chlamydomonas reinhardtii*.

In step (i), the cells are cultured according to any usual protocol known by the skilled artisan. For example, they can be grown photoautotrophically in a MOPS-buffered minimal medium (MM) supplied with 2% $CO_2$ to a density of $2-5 \times 10^6$ cells/nil.

In a particular embodiment of this aspect, said inducing reserve accumulation comprises incubating the microalgae cells in a deficient medium, i.e., a medium which does not comprise, in sufficient quantities, all the nutrients required for optimal growth of green microalgae. Examples of such a deficient medium include a medium deficient in at least one element selected from the group consisting of nitrogen, sulfur and phosphorus, in a form which can be metabolized by the microalgae. Of course, the phrase "deficient in" is not to be read in an absolute sense (i.e., with a concentration equal to zero), but means that the concentration of said nutrient in the medium is far below (at least 10-fold below) the concentration of said nutrient in a classical medium used for microalgae culture.

Between step (i) and step (ii), the cells can be harvested and transferred into the deficient medium. Alternatively, typically in a continuous culture device, the deficit in the medium is created by the cell's metabolism, in absence of exogenous addition of at least one nutrient. For example, as illustrated in the experimental part and in FIG. 9A, addition of minimal N-free medium in a photobioreactor operated as a turbidostat (to maintain the cellular biomass at a constant level) resulted in a decrease in the ammonia content of the culture medium, which was fully exhausted in less than 2 days.

In a particular embodiment, the step of inducing reserve accumulation comprises illuminating the microalgae cells with a light enabling photosynthesis to occur.

For example, this illumination can be performed at an intensity of at least 25 µmol photons $m^{-2} s^{-1}$, or at least 100 µmol photons $m^{-2} s^{-1}$, for example comprised between 25 and 2000 µmol photons $m^{-2} s^{-1}$, during 8 to 24 hours per day. The skilled artisan perfectly knows that the effects of the light intensity depend in fact on the intensity which is really received by the microalgae, and hence depend on several parameters such as cell density and the shape of the photobioreactor, etc., and is able to adapt the illumination intensity to the specific encountered conditions.

Remarkably, the inventors have shown that nutrient deprivation does not lead to a rapid stop of photosynthesis by microalgae lacking DYRKP-1 activity, as is usually the case for wild-type microalgae. This is particularly advantageous, since the cells can not only be oil- and/or starch-enriched, but in addition, the global biomass increases during several days of deficient conditions, leading to remarkable overall increased lipid and starch productivity.

Hence, in an advantageous embodiment of the present invention, the step of incubating the microalgae cells in a deficient medium lasts at least 24 hours, for example from 2 to 8 days, preferably from 3 to 6 days. Of course, the cell growth in a deficient medium strongly depends on experimental conditions, particularly of the cell density, and hence the skilled artisan will adapt the duration of the incubation with a deficient medium so that, under the specific conditions used, the reserve accumulation and/or biomass increase is optimal.

According to a particular embodiment of the invention, step (ii) comprises incubating the microalgae cells in a medium comprising organic carbon such as, for example, acetate. According to a non-limitative example of such mixotrophic conditions, illustrated in the examples below, the cells are incubated in step (ii) during 2 to 6 days in a nitrogen-deficient medium comprising acetate, under constant illumination of at least 50 µmol photons $m^{-2} s^{-1}$. The inventors have shown that in mixotrophic conditions, microalgae lacking DYRKP-1 activity respond to nutrient depletion by increased lipid accumulation compared to wild-type cells. Hence, this particular embodiment of the method is advantageously used for producing oil, for example for biodiesel production.

According to another embodiment, the inducing step (ii) comprises incubating the microalgae cells in a deficient medium as defined previously and in photoautotrophic conditions, i.e., in conditions such that they convert radiant energy into biologically useful energy and synthesize metabolic compounds using only carbon dioxide, bicarbonate or carbonates as source of carbon. Typically, the microalgae cells are incubated under illumination in a medium essentially devoid of organic carbon which they can metabolize. In what precedes, "essentially devoid of organic carbon" means that no organic carbon which can be metabolized by the microalgae has been added into the medium. According to a preferred version of this embodiment, the cells are incubated in step (ii) during at least 15 hours, preferably at least 1, 2 or 3 days, and up to 6 or more days in a nutrient-deficient medium, for example in a nitrogen-deficient medium essentially devoid of organic carbon which can be metabolized by the microalgae. The inventors have shown that in photoautotrophic conditions, microalgae lacking DYRKP-1 activity accumulate much more starch and oil than their wild-type progenitor in response to nutrient deprivation. Hence, this particular embodiment of the method is advantageously used for producing starch, for example for bioethanol production, as well as for producing oil, for example for biodiesel production. This embodiment is particularly interesting, because in photoautotrophic conditions, cells can supply their need for carbon completely through photosynthesis, which is a major advantage compared to cells requiring an additionally supplied carbon source for growth (such as yeast or *E coli*).

It is to be noted that microalgae naturally produce polyunsaturated fats (omega-3 and omega-6), as well as complex molecules such as carotenoids, and that these high-value products can also be produced according to the methods described herein. The invention hence also relates to methods for producing fatty acids, polyunsaturated fats, carotenoids and other compounds for cosmetic and/or pharmaceutical industries, as well as food supplements, comprising a step of starch and/or triacylglycerols accumulation in microalgae by performing a method as described above The methods of the invention may comprise one or more extraction steps after the triggering of starch and/or triacylglycerols accumulation step in microalgae. The extraction step may be implemented using solvents or another extraction method well known form the skilled artisan.

The present invention will be understood more clearly from the further description which follows, which refers to examples illustrating the response of microalgae lacking DYRKP-1 activity to nutrient deprivation, as well as to the appended figures.

FIGURE LEGENDS

FIGS. 1A through 1E describe the isolation and molecular characterization of the *Chlamydomonas* std1 mutant affected in the DYRKP-1 gene.

FIG. 1A depicts starch degradation phenotype of the std1 mutant. Algal colonies were spotted on paper filters onto N or S depleted TAP-agar for 5 days, leading to starch accumulation, and then placed in the dark on minimal medium (MM) for two days to induce starch breakdown. Starch accumulation was visualized by exposure to iodine vapor.

FIG. 1B depicts the *Chlamydomonas* DYRKP-1 gene model is composed of 14 exons (black boxes) and 13 introns (black lines). Sequence information about the exon-intron borders and the 5' start was obtained from three overlapping RT-PCRs. Insertion of the paromomycin resistance cassette (AphVIII gene, white box) in the third DYRKP-1 exon was determined by genome walking PCR.

FIG. 1E depicts DYRKP-1 transcript accumulation in response to N deprivation. Wild-type, std1 mutant and complemented strains std1::STD1 1 and 2 were starved for nitrogen for three days in photoautotrophic conditions. RNA was hybridized with probes coding for a DYRKP-1 fragment; the CBLP2 gene that served as a loading control.

Figure 2A:
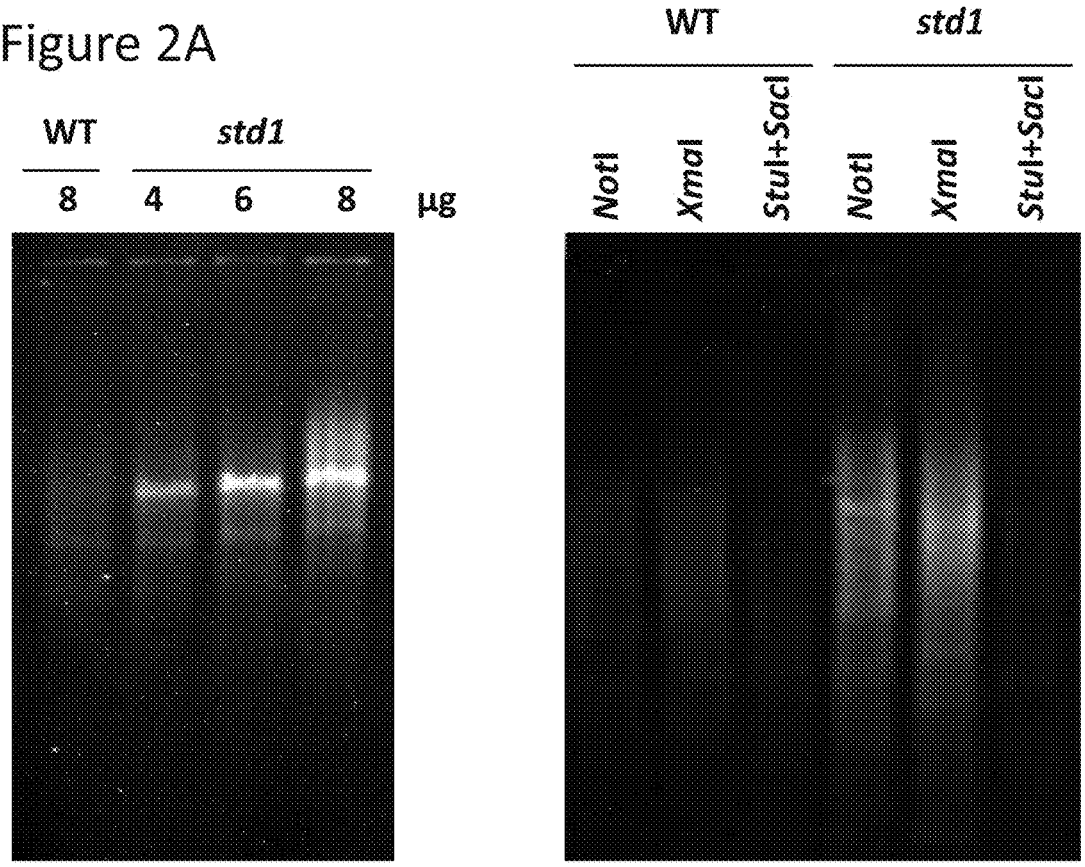
Figure 2B:
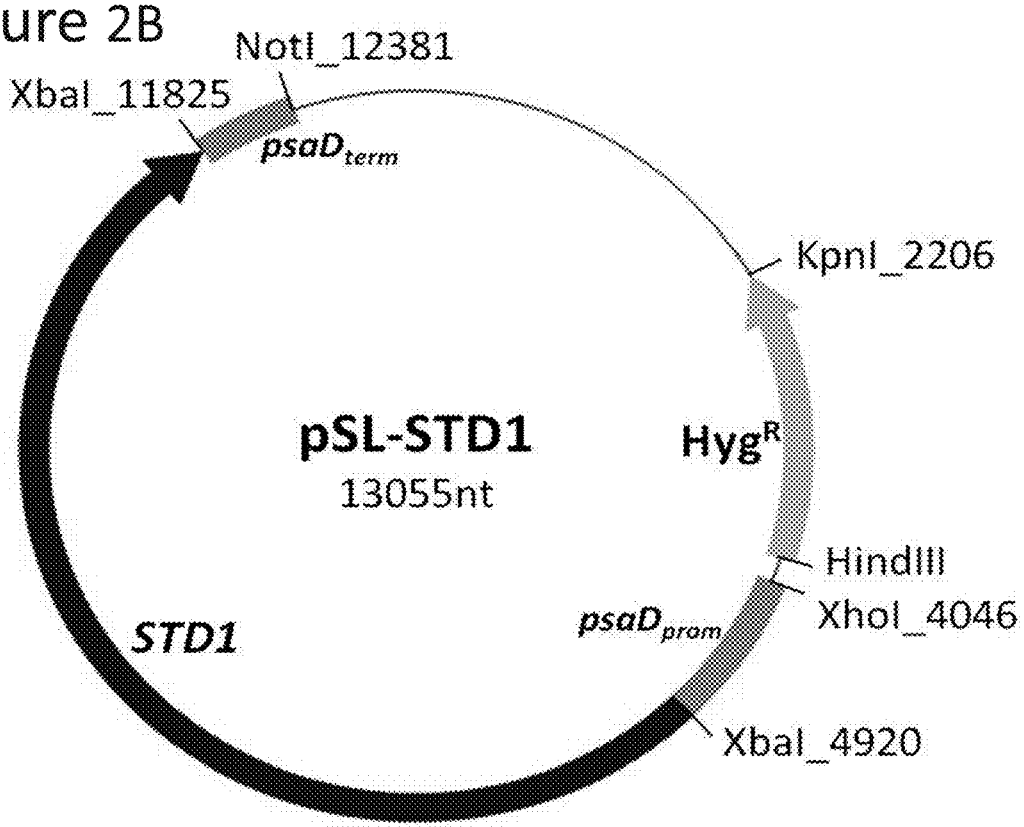
Figure 2C:
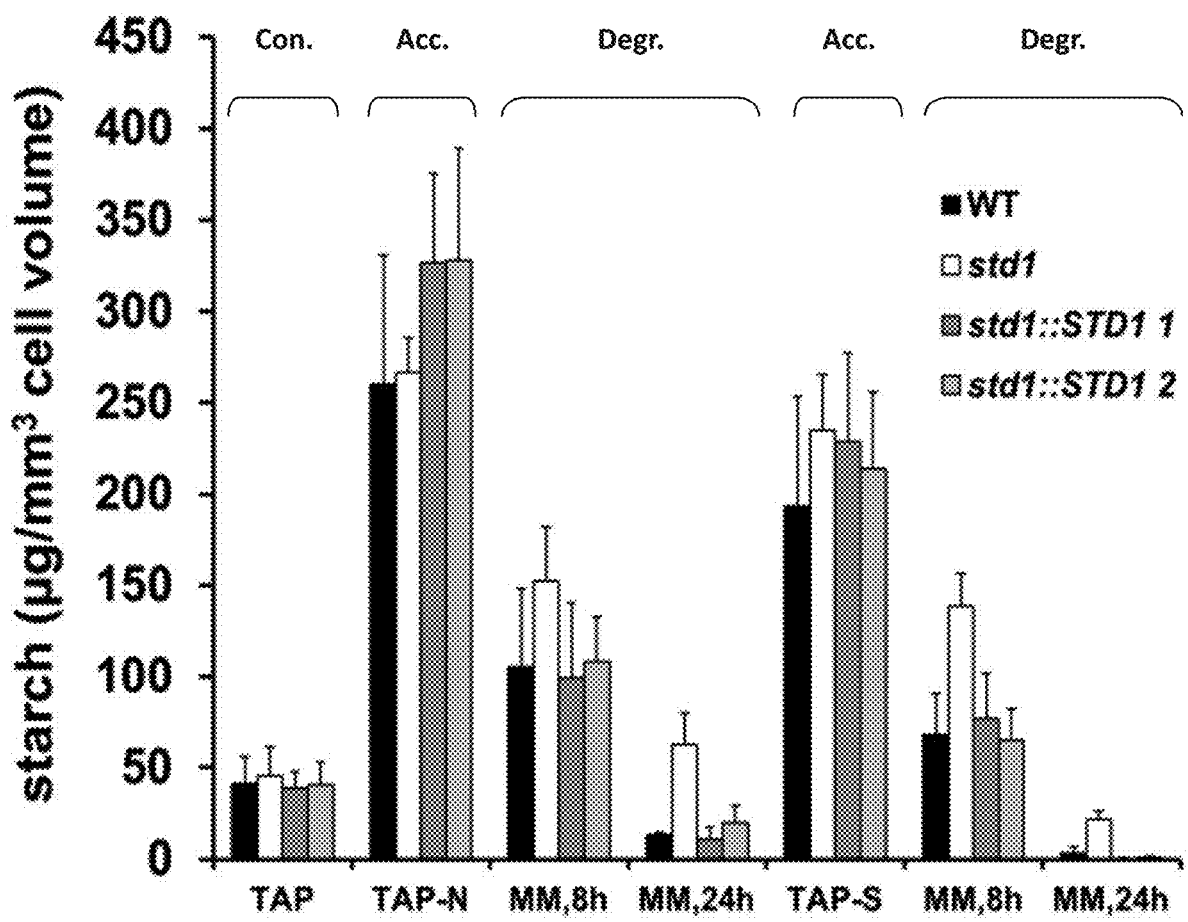

FIGS. 2A through 2C depict Southern blot analysis and mutant complementation.

FIG. 2A depicts Southern blot analysis of wild-type strain 137AH and std1 mutant strain. NotI-, XmaI- or StuI/SacI-restricted genomic DNA was loaded on an agarose gel, Southern blotted and hybridized with a probe against the AphVIII gene (paromomycin resistance cassette). Loaded amount of DNA per lane is indicated in µg.

FIG. 2B depicts construction of the plasmid for std1 complementation with hygromycin resistance marker. Genomic wild-type DNA coding for STD1 was amplified by PCR and cloned into pSL-Hyg vector that emerged from pSL18.

FIG. 2C depicts starch levels of wild-type strain (137AH, in black), std1 mutant strain (white) and two complemented strains (std1::STD1 1 and 2, in grey) in different deprivation conditions. Cultures were grown in TAP medium (Con.=Control), subjected for two days to nitrogen (TAP-N) or sulfur (TAP-S) starvation, which induced starch accumulation (Acc.). Subsequently, the starved cultures were centrifuged, resuspended in minimal medium (MM) and kept for 8 or 24 h hours in the dark. In MM (comprising N but no C) in the dark starch will be catabolized (Degr.). Starch values are the means of at least 3 biological replicates ±SD.

Figures 3A, 3B:
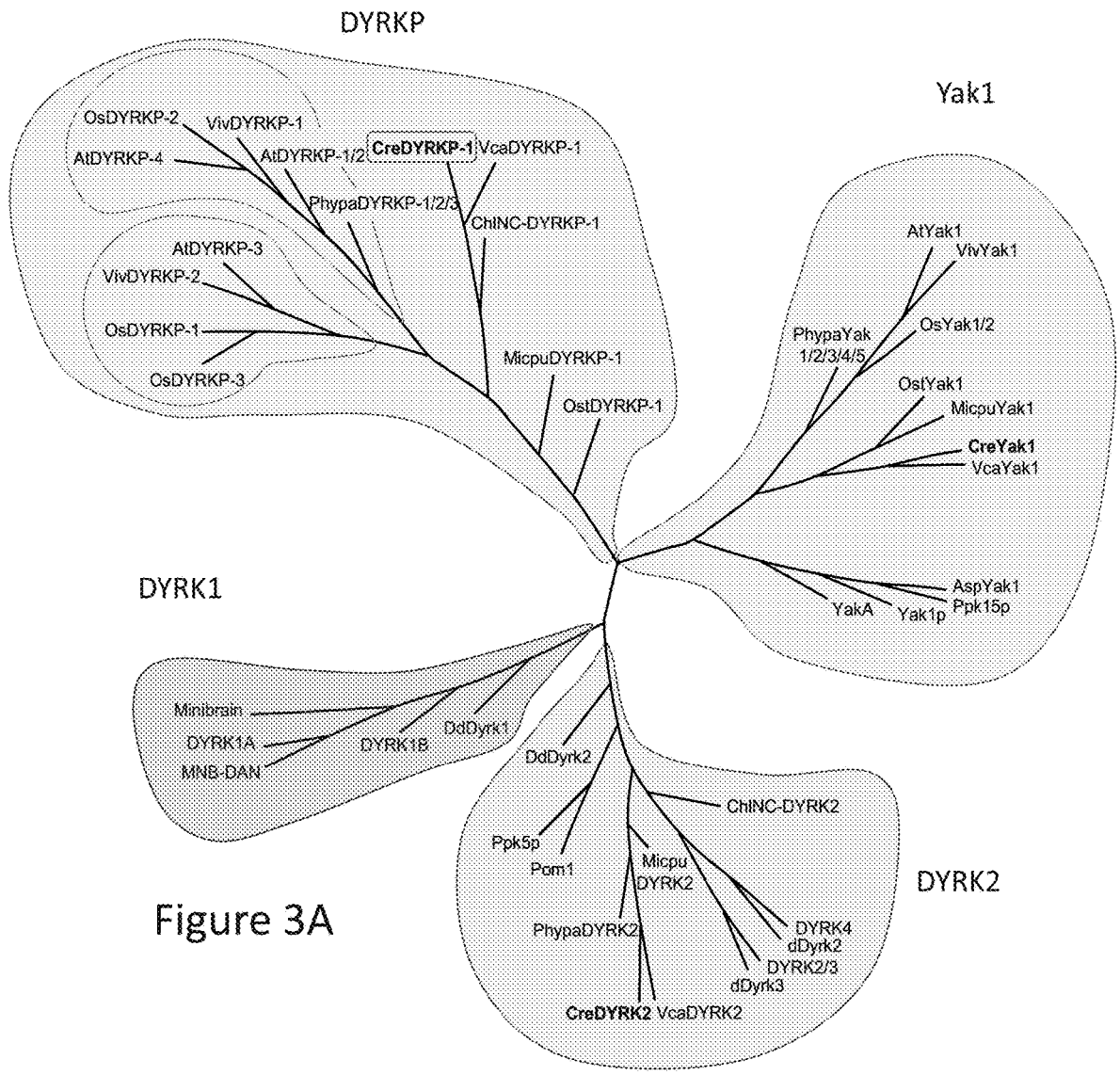

FIGS. 3A through 3B depict a phylogenetic tree of the DYRK protein family including the green lineage.

FIG. 3A depicts a phylogenetic tree of the DYRK protein family. Homologous amino acids sequences from algae, fungi and plants retrieved from JGI, Phytozome or NCBI databases were compared by performing a phylogenetic analysis. Sequences were aligned with the MAFFT version 6 program. The tree was obtained with the Neighbor-Joining method. The following abbreviations were used: Asp: *Aspergillus fumigatus*, At: *Arabidopsis thaliana*, d: *Drosophila melanogaster*, Dd: *Dictyostelium discoideum*, ChlNC: *Chlorella* sp. NC64A, Cre: *Chlamydomonas reinhardtii*, Micpu: *Micromonas pusilla* (CCMP1545/sp. RCC299), Os: *Oryza sativa*, Ost: *Ostreococcus* (*lucimarinus/tauri*), Phypa: *Physcomitrella patens*, Vca: *Volvox carteri*, Viv: *Vitis vinifera* (*Zea mays* sequences were combined with rice homologs and *Populus trichocarpa* with wine). DYRK sequences accession numbers and multi-alignment used to build the phylogenetic tree are shown in Table 1.

FIG. 3B depicts consensus sequence of the DYRK homology (DH)-box of six DYRK subgroups according to FIG. 3A; in the DYRKP subgroup three minor subgroups were distinguished giving the following seven classes: DYRK1 (7 sequences; SEQ ID NO:19), DYRK2 (22 sequences; SEQ ID NO:20), YAK1 (21 sequences; SEQ ID NO:21), DYRKP-A (12 higher plant sequences including moss; SEQ ID NO:22), DYRKP-B (11 higher plant sequences; SEQ ID NO:23), DYRKP-algae (7 sequences; SEQ ID NO:24), and the published DH consensus sequence from (Becker and Joost, 1999), in which nine sequences from different DYRK groups were compared (SEQ ID NO:18).

TABLE 1

Accession numbers for the sequences used for the phylogenetic tree in FIG. 2.

| Name | Group | Species | Accession Number NCBI | predicted aa |
|---|---|---|---|---|
| DYRK1A | DYRK1 | *Homo sapiens* | NP_001387; GI:18765758 | 763 |
| DYRK1B | DYRK1 | *Homo sapiens* | NP_004705; GI:4758222 | 629 |
| DYRK2 | DYRK2 | *Homo sapiens* | NP_006473; GI:153281169 | 601 |
| DYRK3 | DYRK2 | *Homo sapiens* | NP_003573; GI:51702240 | 588 |
| DYRK4 | DYRK2 | *Homo sapiens* | NP_003836; GI:28827774 | 520 |
| DYRK1A | DYRK1 | *Mus musculus* | NP_031916; GI:24418935 | 763 |
| DYRK1B | DYRK1 | *Mus musculus* | NP_001033046; GI:83816922 | 629 |
| DYRK2 | DYRK2 | *Mus musculus* | NP_001014412; GI:67846105 | 599 |
| DYRK3 | DYRK2 | *Mus musculus* | NP_663483; GI:21704000 | 586 |
| DYRK4 | DYRK2 | *Mus musculus* | NP_001028487; GI:161333817 | 616 |
| Minibrain (dDyrk1) | DYRK1 | *Drosophila melanogaster* | NP_728104; GI:24642876 | 908 |
| dDyrk2 (Smi35A) | DYRK2 | *Drosophila melanogaster* | NP_523564; GI:17737415 | 722 |
| dDyrk3 | DYRK2 | *Drosophila melanogaster* | NP_001033810; GI:85724756 | 828 |
| DYRK1B (Dyrk1b) | DYRK1 | *Danio rerio* | NP_001161737; GI:319996595 | 681 |
| DYRK2 | DYRK2 | *Danio rerio* | NP_001038298.1; GI:113677529 | 587 |
| DYRK4 | DYRK2 | *Danio rerio* | XP_693389; GI:189537435 | 634 |
| DYRK3 | DYRK2 | *Xenopus laevis* | NP_001088793; GI:148224808 | 567 |
| YakA | Yak | *Dictyostelium discoideum* | XP_638920; GI:66810395 | 1458 |

TABLE 1-continued

Accession numbers for the sequences used for the phylogenetic tree in FIG. 2.

| | | | | |
|---|---|---|---|---|
| DdDyrk1 | DYRK1 | *Dictyostelium discoideum* | XP_642598; GI:66817490 | 836 |
| DdDyrk2 | DYRK2 | *Dictyostelium discoideum* | XP_628965; GI:66800079 | 915 |
| Yak1p | Yak | *Saccharomyces cerevisiae* | NP_012394; GI:6322320 | 807 |
| Pom1 | Pom/DYRK2 | *Neurospora crassa* | XP_960871; GI:85099941 | 1300 |
| Pom1 | Pom/DYRK2 | *Pyrenophora tritici-repentis* | XP_001940188; GI:189207709 | 545 |
| Ppk15p | Yak | *Schizosaccharomyces pombe* | NP_593830; GI:19114742 | 534 |
| Pom1 (Pom1p) | Pom/DYRK2 | *Schizosaccharomyces pombe* | NP_592974; GI:19113886 | 1087 |
| Ppk5p | Pom/DYRK2 | *Schizosaccharomyces pombe* | NP_593081; GI:63054495 | 836 |
| AspYak1 | Yak | *Aspergillus fumigatus* | XP_746572; GI:70982087 | 894 |

| Name | Groupe | Species | Gene Model | Accession Number NCBI | predicted aa | genome website |
|---|---|---|---|---|---|---|
| AtYak1 | Yak | *Arabidopsis thaliana* | AT5G35980 | NP_198447; GI:42568145 | 956 | The Arabidopsis Information Resource |
| AtDYRKP-1 | DYRKP | *Arabidopsis thaliana* | AT1G73450 | NP_177487; GI:42563202 | 1152 | |
| AtDYRKP-2 | DYRKP | *Arabidopsis thaliana* | AT1G73460 | NP_177488; GI:42563204 | 1169 | |
| AtDYRKP-3 | DYRKP | *Arabidopsis thaliana* | AT2G40120 | NP_181541; GI:15225633 | 570 | |
| AtDYRKP-4 | DYRKP | *Arabidopsis thaliana* | AT3G17750 | NP_188402; GI:15229515 | 1138 | |
| OsYak1 | Yak | *Oryza sativa* ssp *japonica* | Os02g0702500 | NP_001047851; GI:115448143 | 813 | Michigan State University - Rice Genome Annotation Project |
| OsYak2 | Yak | *Oryza sativa* ssp *japonica* | Os04g0602800 | NP_001053776; GI:115460352 | 924 | Joint Genome Institute - Plant Comparative Genomics Portal (JGI) |
| OsDYRKP-1 | DYRKP | *Oryza sativa* ssp *japonica* | Os01g0832900 | NP_001044708; GI:115440857 | 729 | |
| OsDYRKP-2 | DYRKP | *Oryza sativa* ssp *japonica* | Os03g0719500 | NP_001051095; GI:115454989 | 1115 | |
| OsDYRKP-3 | DYRKP | *Oryza sativa* ssp *japonica* | Os05g0466900 | NP_001055789; GI:297604629 | 708 | |
| VivYak1 | Yak | *Vitis vinifera* | GSVIVG01024260001 | XP_002267912.1; GI:225454595 | 909 | JGI |
| VivDYRKP-1 | DYRKP | *Vitis vinifera* | GSVIVG01012107001 | XP_002276420.1; GI:225423662 | 1855 | |
| VivDYRKP-2 | DYRKP | *Vitis vinifera* | GSVIVG01032814001 | XP_002272072.1; GI:225448445 | 728 | |
| ZmYak1 | Yak | *Zea mays* | GRMZM2G156638 | NP_001159228.1; GI:259490627 | 706 | (incomplete) |
| ZmYak2 | Yak | *Zea mays* | GRMZM2G311051 | ACL53420.1; GI:219886091 | 556 | (incomplete) |
| ZmDYRKP-1 | DYRKP | *Zea mays* | GRMZM2G015073 | Not found | 1103 | Gramene Database |
| ZmDYRKP-2 | DYRKP | *Zea mays* | GRMZM2G181002 | Not found | 1098 | JGI |
| ZmDYRKP-3 | DYRKP | *Zea mays* | GRMZM2G068192 | NP_001145942.1; GI:226530085 | 391 | |
| ZmDYRKP-4 | DYRKP | *Zea mays* | GRMZM2G088409 | NP_001182917.1; GI:308081613 | 684 | |
| ZmDYRKP-5 | DYRKP | *Zea mays* | GRMZM2G357873 | NP_001130373.1; GI:212275250 | 724 | |
| ZmDYRKP-6 | DYRKP | *Zea mays* | GRMZM2G448633 | NP_001148168.1; GI:226506060 | 725 | |
| PhypaYak1 | Yak | *Physcomitrella patens* | Pp1s3_592V6.1 | No completed gene models at NCBI | 959 | Plant Genome Database JGI |
| PhypaYak2 | Yak | *Physcomitrella patens* | Pp1s16_333V6.1 | | 1064 | |
| PhypaYak3 | Yak | *Physcomitrella patens* | Pp1s132_192V6.1 | | 1108 | |
| PhypaYak4 | Yak | *Physcomitrella patens* | Pp1s192_46V6.1 | | 1089 | |
| PhypaYak5 | Yak | *Physcomitrella patens* | Pp1s401_7V6.1 | | 1136 | |

TABLE 1-continued

Accession numbers for the sequences used for the phylogenetic tree in FIG. 2.

| Name | Type | Species | Locus | Accession | Length | Source |
|---|---|---|---|---|---|---|
| PhypaDYRK2 | DYRK2 | Physcomitrella patens | Pp1s252_88V6.1 | | 1129 | |
| PhypaDYRKP-1 | DYRKP | Physcomitrella patens | Pp1s47_312V6.1 | | 726 | |
| PhypaDYRKP-2 | DYRKP | Physcomitrella patens | Pp1s312_23V6.1 | | 525 | |
| PhypaDYRKP-3 | DYRKP | Physcomitrella patens | Pp1s381_39V6.1 | | 1446 | |
| PoptrYak1 | Yak | Populus trichocarpa | POPTR_0013s07280 | EEE95157.1; GI:222857610 | 966 | |
| PoptrYak2 | Yak | Populus trichocarpa | POPTR_0019s06030 | EEF00267.1; GI:222862760 | 893 | |
| PoptrDYRKP-1 | DYRKP | Populus trichocarpa | POPTR_0008s06890 | EEE89528.1; GI:222851981 | 725 | |
| PoptrDYRKP-2 | DYRKP | Populus trichocarpa | POPTR_0010s19570 | EEF01327.1; GI:222864196 | 591 | |
| PoptrDYRKP-3 | DYRKP | Populus trichocarpa | POPTR_0012s03670 | EEE96543.1; GI:222858996 | 1158 | |
| PoptrDYRKP-4 | DYRKP | Populus trichocarpa | POPTR_0015s05140 | EEF07789.1; GI:222870658 | 1151 | |
| CreYak1 | Yak | Chlamydomonas reinhardtii | Cre08.g381950 | XP_001694330; GI:159472382 | 2202 | JGI |
| CreDYRK2 | DYRK2 | Chlamydomonas reinhardtii | Cre02.g146500 | XP_001695011; GI:159473779 | 1239 | |
| CreDYRKP-1 | DYRKP | Chlamydomonas reinhardtii | Cre07.g337300 | XP_001700085; GI:159484074 | 1278 | |
| VcaYak1 | Yak | Volvox carteri | Volca1|30949 | XP_002953068; GI:302843051 | 398 (incomplete) | JGI |
| VcaDYRK2 | DYRK2 | Volvox carteri | Volca1|61790 | XP_002951959; GI:302840826 | 512 | |
| VcaDYRKP-1 | DYRKP | Volvox carteri | Volca1|77582 | XP_002957430; GI:302851815 | 370 | |
| OstluYak1 | Yak | Ostreococcus lucimarinus CCE9901 | Ost9901_3|37908 | XP_001420045; GI:145351353 | 425 | JGI |
| OstluDYRKP-1 | DYRKP | Ostreococcus lucimarinus CCE9901 | Ost9901_3|36819 | XP_001417467; GI:145345962 | 395 | |
| Ostlu38674 | DYRK2? | Ostreococcus lucimarinus CCE9901 | Ost9901_3|38674 | XP_001418004; GI:145347077 | 397 (incomplete) | |
| Ostlu42173 | DYRK1? | Ostreococcus lucimarinus CCE9901 | Ost9901_3|42173 | XP_001422264; GI: 145356070 | 154 (incomplete) | |
| OsttaYak1 | Yak | Ostreococcus tauri | Ostta4|19878 | XP_003081795; GI:308808970 | 772 | JGI |
| OsttaDYRKP-1 | DYRKP | Ostreococcus tauri | Ostta4|16877 | XP_003078697; GI:308802768 | 652 | |
| Ostta17596 | DYRK2? | Ostreococcus tauri | Ostta4|17596 | XP_003079347; GI:308804069 | 837 (incomplete) | |
| Ostta22490 | DYRK1? | Ostreococcus tauri | Ostta4|22490 | XP_003084217; GI:308813822 | 472 (incomplete) | |
| ChlNC-DYRK2 | DYRK2 | Chlorella sp. NC64A | ChlNC64A_1|16563 | EFN52309; GI:307104053 | 364 (incomplete) | JGI |
| ChlNC-DYRKP-1 | DYRKP | Chlorella sp. NC64A | ChlNC64A_1|36965 | EFN52148; GI:307103891 | 285 (incomplete) | |
| MicpuC-Yak1 | Yak | Micromonas pusilla CCMP1545 | MicpuC3|39551 | XP_003057930; GI:303277273 | 605 | JGI |
| MicpuC-DYRK2 | DYRK2 | Micromonas pusilla CCMP1545 | MicpuC3|152430 | XP_003057384; GI:303276180 | 513 | |
| MicpuC-DYRKP-1 | DYRKP | Micromonas pusilla CCMP1545 | MicpuC3|16074 | XP_003058010; GI:303277433 | 341 | |
| MicpuC8718 | DYRK1? | Micromonas pusilla CCMP1545 | MicpuC3|8718 | XP_003057290; GI:303275992 | 143 (incomplete) | |
| MicpuN-Yak1 | Yak | Micromonas sp. RCC299 | MicpuN3|83368 | XP_002503782; GI:255080404 | 421 | JGI |
| MicpuN-DYRK2 | DYRK2 | Micromonas sp. RCC299 | MicpuN3|58615 | XP_002502528; GI:255077896 | 642 | |
| MicpuN-DYRKP-1 | DYRKP | Micromonas sp. RCC299 | MicpuN3|58100 | XP_002501491; GI:25507563 | 1019 | |
| MicpuN85819 | DYRK1? | Micromonas sp. RCC299 | MicpuN3|85819 | XP_002508509; GI:255083869 | 238 (incomplete) | |

Sequences in bold were not utilized for the alignment. Definitively incomplete gene models are indicated. When predicted number of amino acids differed at two compared genome databases, usually the longer version was chosen. Some genes have different splice variants, e.g. "ZmDYRKP3" that harbours three transcripts at this locus. In case of *Danio rerio* and *Xenopus laevis*, not all existing DYRK genes were provided for the alignment.

Figure 4A:
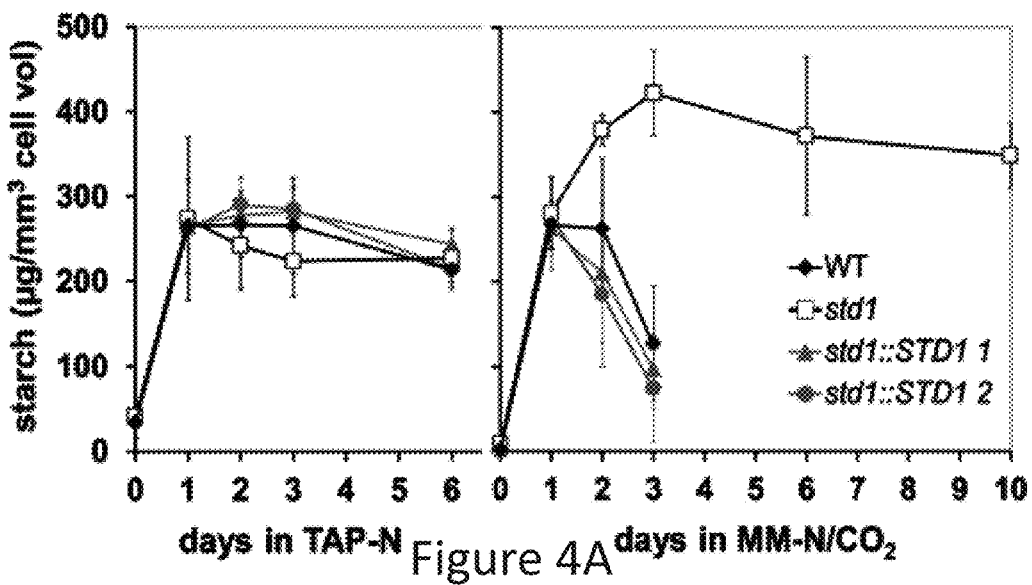
Figure 4B:
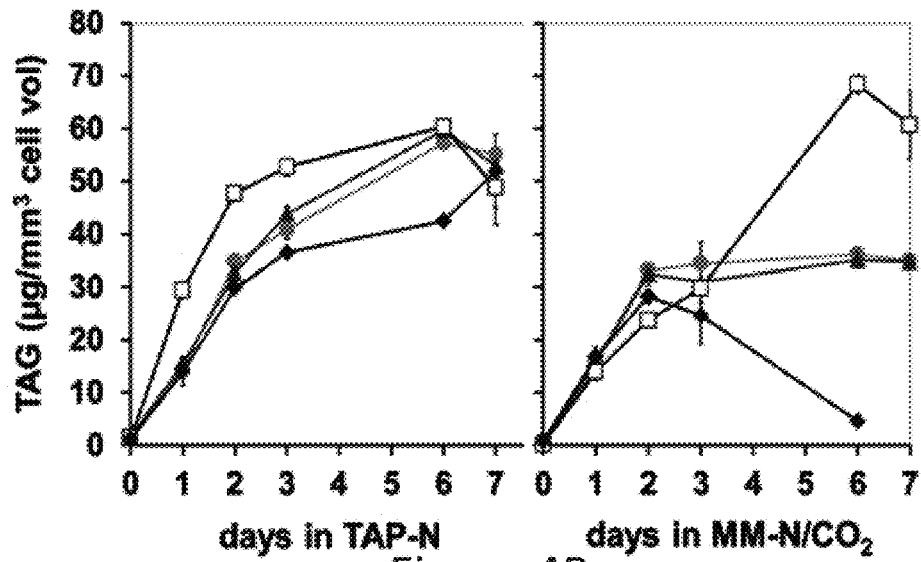
Figure 4C:
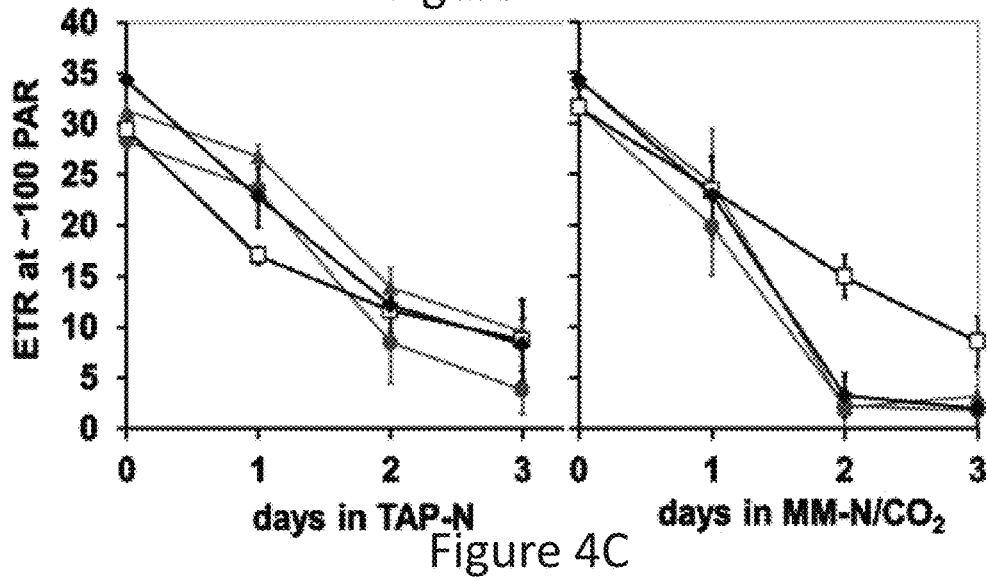

FIGS. 4A through 4D depict carbon storage and photosynthetic activity in the std1 mutant in response to nitrogen deprivation. Cells were grown in TAP or minimal medium with 2% $CO_2$ in air under a constant illumination of 100 µmol photons $m^{-2}$ $s^{-1}$. At day 0, cells were centrifuged, washed and resuspended in TAP-N (left panels; FIGS. 4A-4C) or MM-N (right panels; FIGS. 4A-4C). Measurements were performed in wild-type (WT), std1 mutant and in two complemented strains std1::STD1 1 and std1::STD1 2 (FIGS. 4A-4C).

FIG. 4A depicts intracellular starch accumulation. Shown are means of 4 experiments (3 for day 6)±SD for TAP-N and means of 6 experiments (3 for day 10)±SD for MM-N.

FIG. 4B depicts intracellular accumulation of neutral lipids (TAGs). Upon extraction of total cellular lipids, TAGs were separated by thin layer chromatography and quantified. One representative experiment out of three biological replicates is shown for each condition (TAP-N or MM-N). TAG values are mean of three technical replicates ±SD.

FIG. 4C depicts photosynthetic electron transport rate (ETR) as determined from chlorophyll fluorescence measurements during the first three days of N deprivation. Plotted values are the means of 4 (TAP-N) or 6 (MM-N) measurements ±SD under actinic illumination of ~100 µmol photons $m^2$ $s^{-1}$.

Figure 4D:
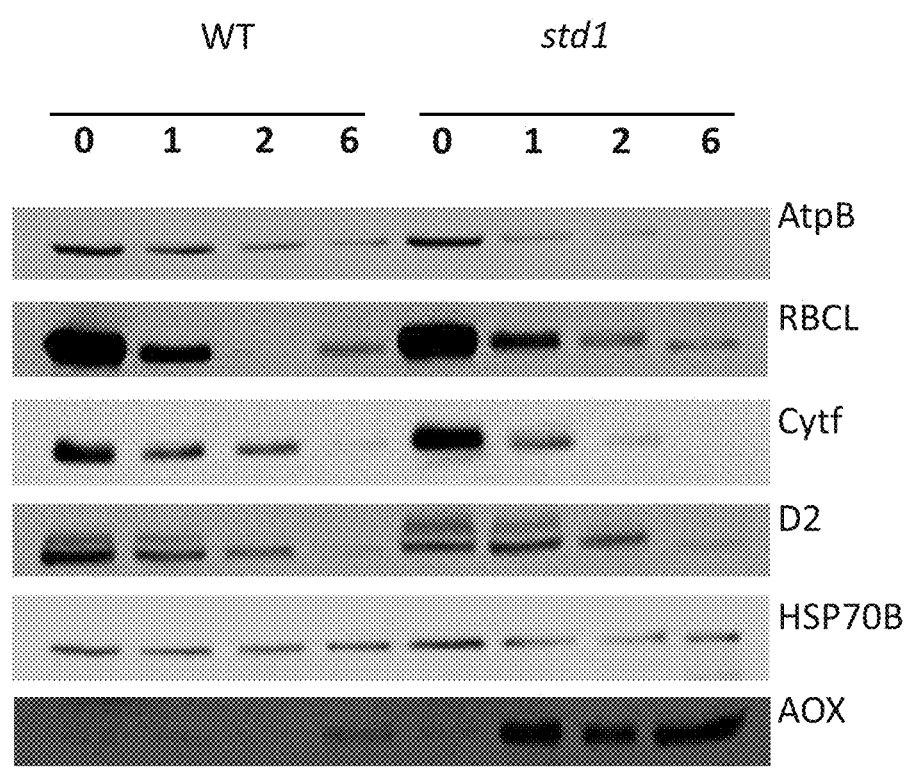

FIG. 4D depicts immunodetection of proteins of interest. Whole cell protein extracts were analyzed by immunodetection after 1, 2 or 6 days of nitrogen starvation in photoautotrophic conditions (MM-N). Proteins were separated on a 10% SDS-polyacrylamide gel and stained by Coomassie blue for loading control (FIG. 7C) or immunoblotted to detect the indicated proteins.

FIGS. 5A through 5D depict intracellular starch accumulation and photosynthetic activity in photoautotropically grown cultures submitted to N-deprivation or S-deprivation.

At day 0, phototoautropically grown cultures (MM, 2% $CO_2$ in air) of wild-type (WT), mutant (std1) and two complemented (std1::STD1 1 and 2) strains were centrifuged, washed and resuspended in MM-N or MM-S in the presence of 2% $CO_2$ in air. At different time points, cell pellets, total cellular volume and dry weight biomass were analyzed.

Figure 5A:
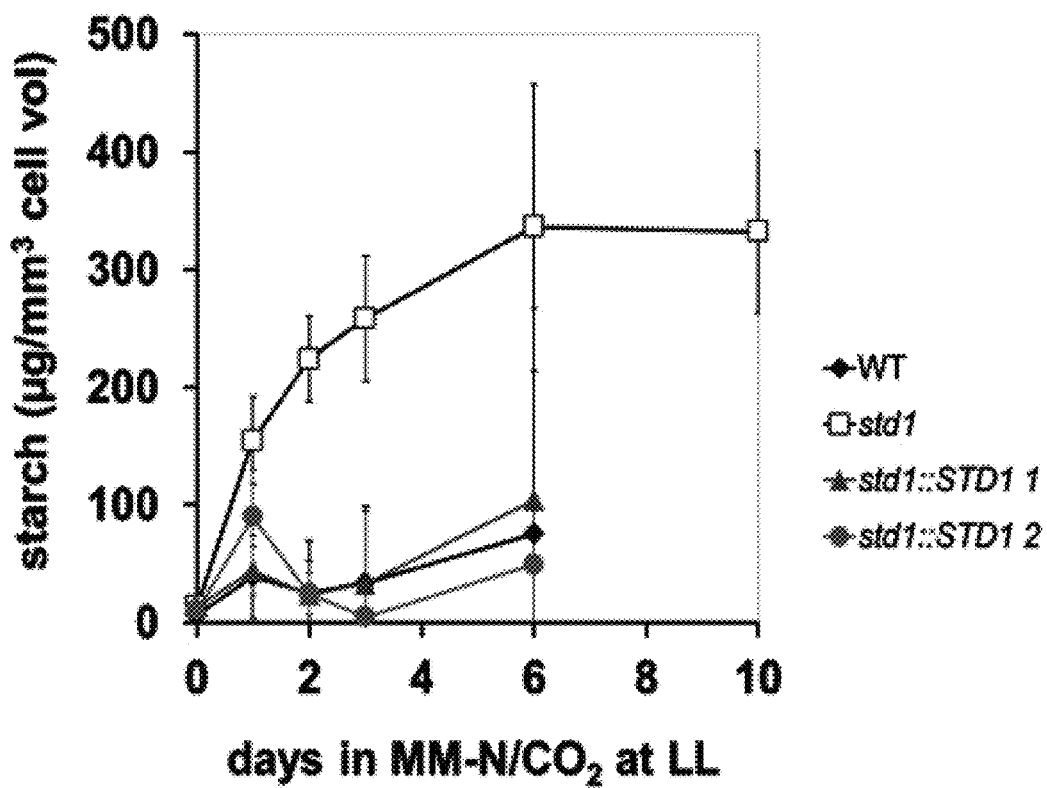
Figure 5B:
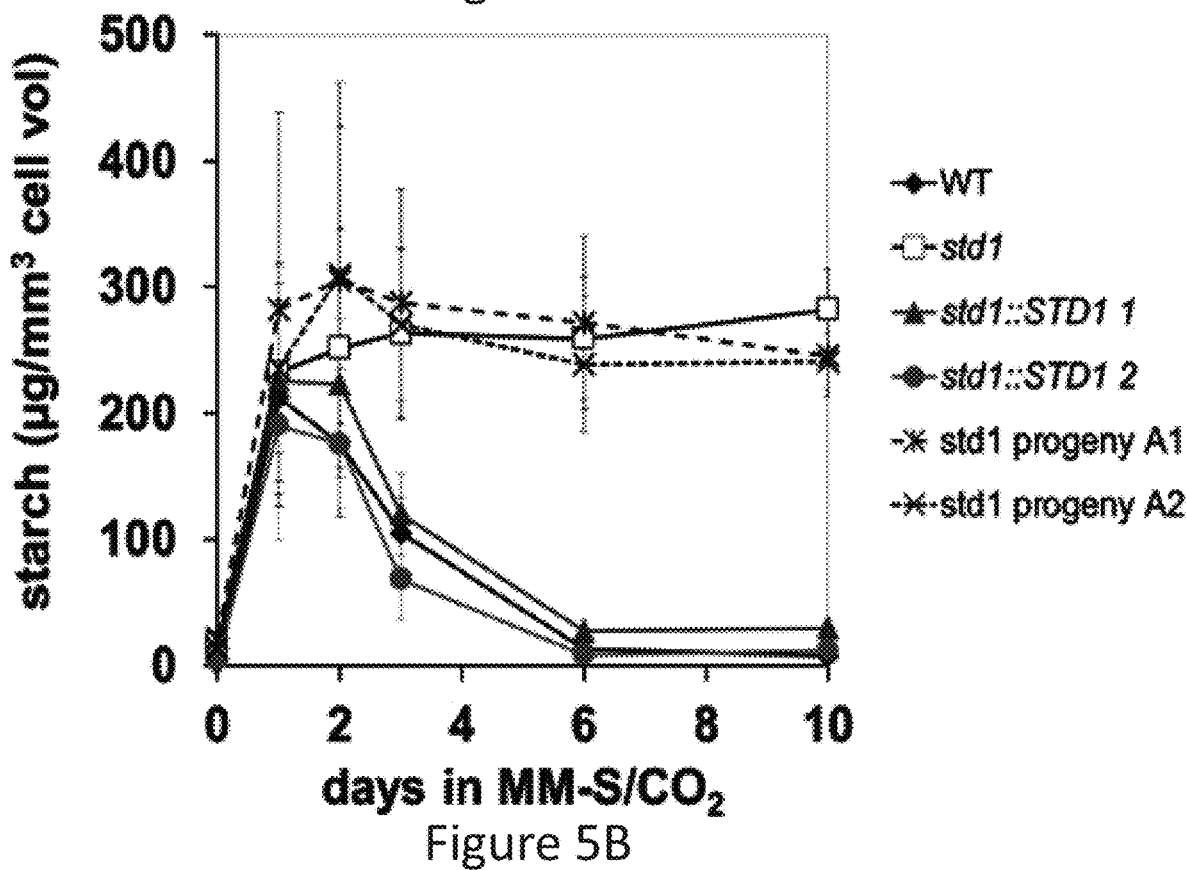

FIG. 5A depicts starch dynamics in autotrophic N deprivation and FIG. 5B depicts autotrophic S deprivation at low light intensities of 30-40 µmol photons $m^{-2}$ $s^{-1}$. Starch values are the means of 5 biological replicates ±SD and means of 3 experiments for the std1 progeny strains 1A and 2A resulting from a backcross of std1 (mt−nit1 nit2) with the wild-type CC125 (mt+nit1 nit2), both are of the type "137c" strain. Four experiments were performed in MM-N/$CO_2$ at low light intensities of 30-40 µmol photons $m^{-2}$ $s^{-1}$.

Figure 5C:
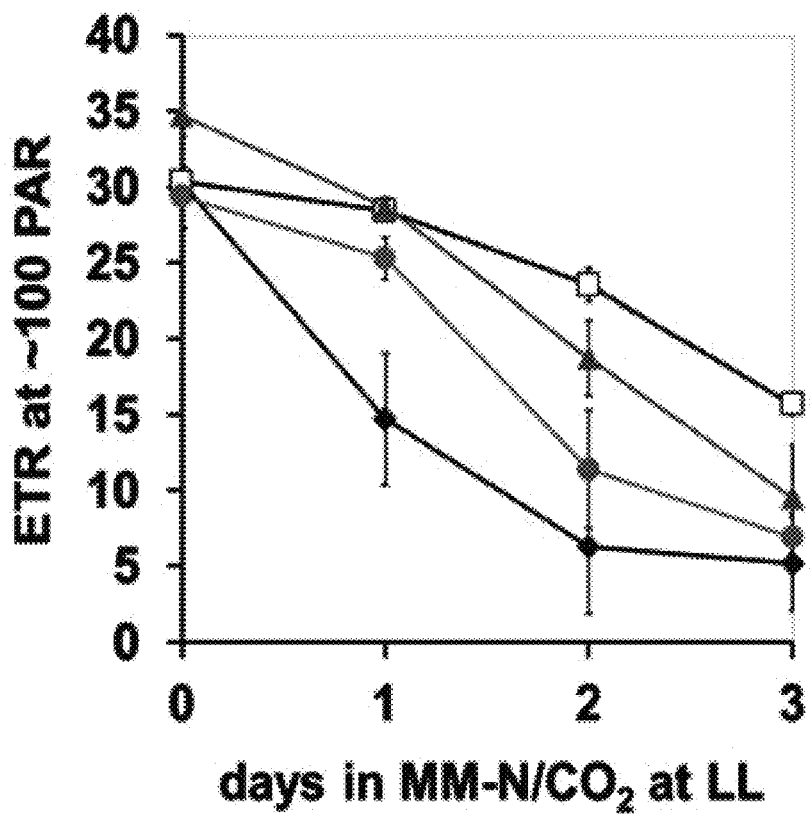
Figure 5D:
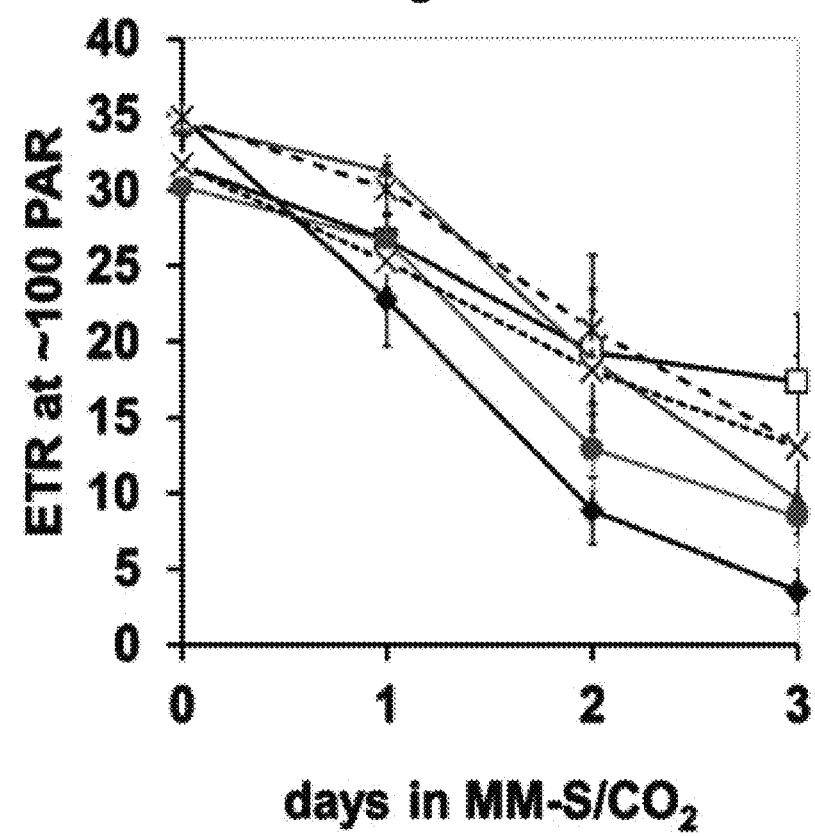

FIG. 5C depicts photosynthetic efficiencies of wild-type, std1 mutant and complemented cells during three days of N deprivation at ~35 µE $m^{-2}$ $s^{-1}$ in autotrophic conditions or FIG. 5D depicts S deprivation at 100 µE $m^{-2}$ $s^{-1}$. Plotted values are the means of 5 measurements ±SD at an illumination of ~100 µE $m^{-2}$ $s^{-1}$.

Figure 6A:
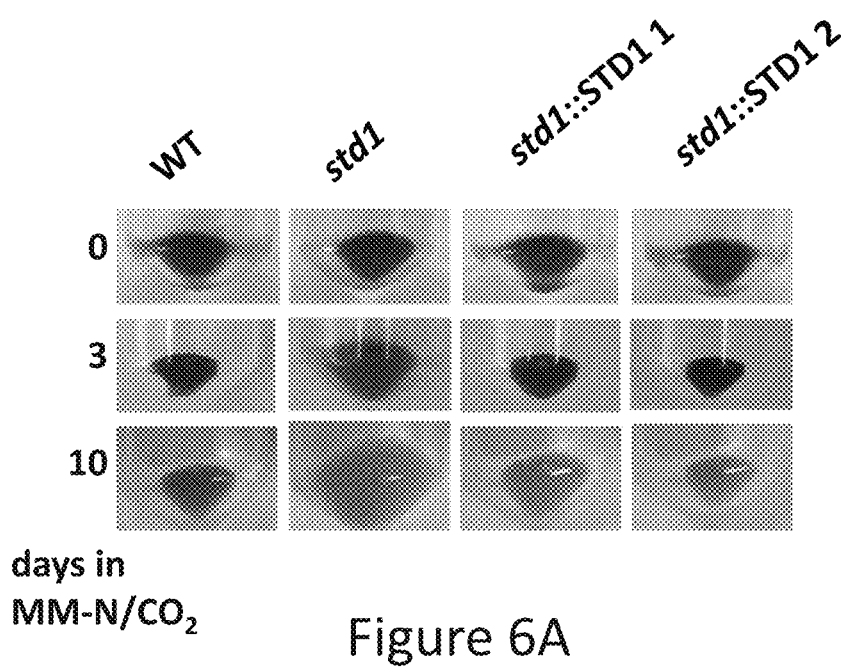
Figure 6B:
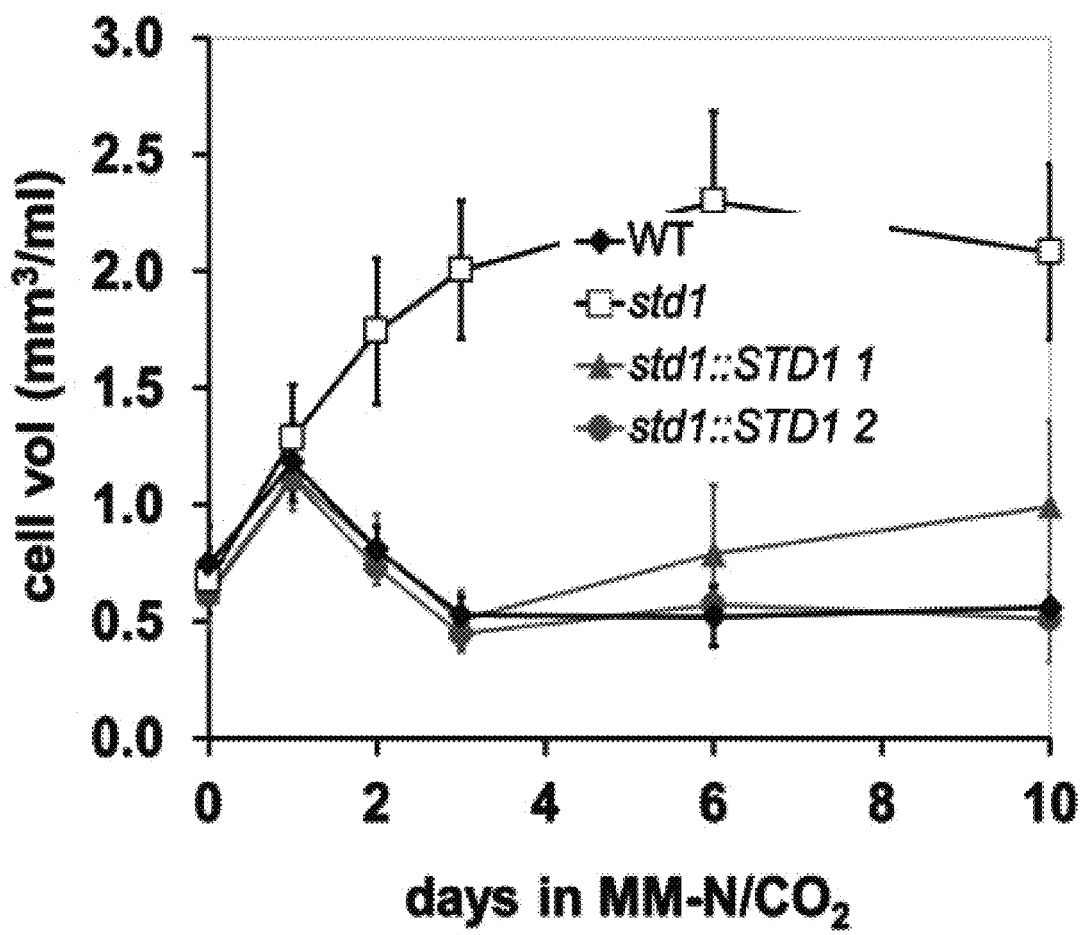
Figure 6C:
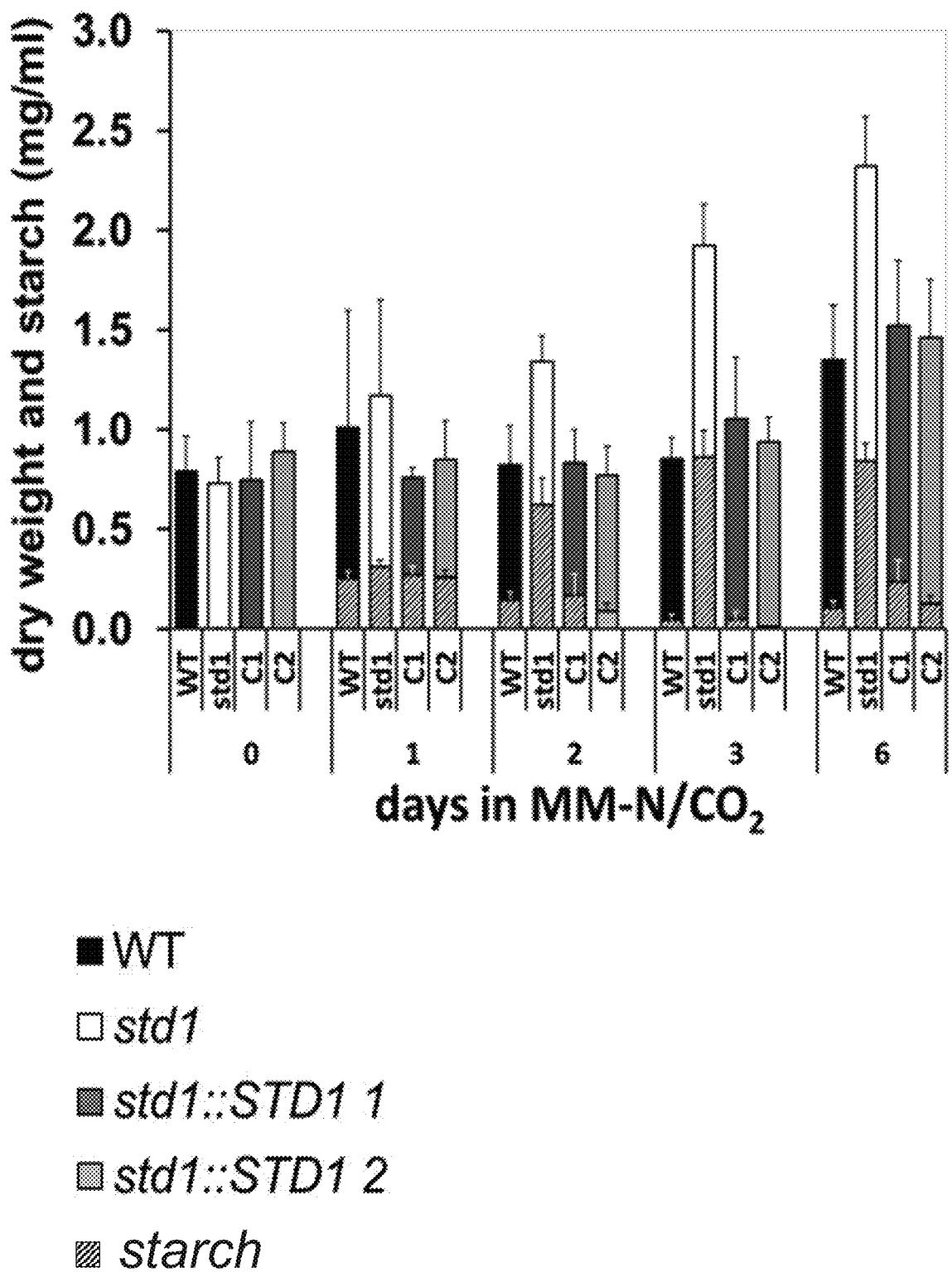

FIGS. 6A through 6C depict biomass productivity of the std1 mutant during N deprivation in photo-autotrophic conditions. Experimental setup was the same as in FIG. 5 but using only a MM-N medium.

In FIG. 6A cells were harvested from 1 mL culture, centrifuged and pellets pictured.

In FIG. 6B total cellular volume was determined per mL. Shown are means±SD (n=7).

In FIG. 6C was determined as dry weight from five 5 mL cultures harvested by filtration, rinsed, and dried overnight. Analysis of intracellular starch allowed determination of the starch fraction of total biomass (hatched area). Shown are means±SD (n=3).

Figure 7A:
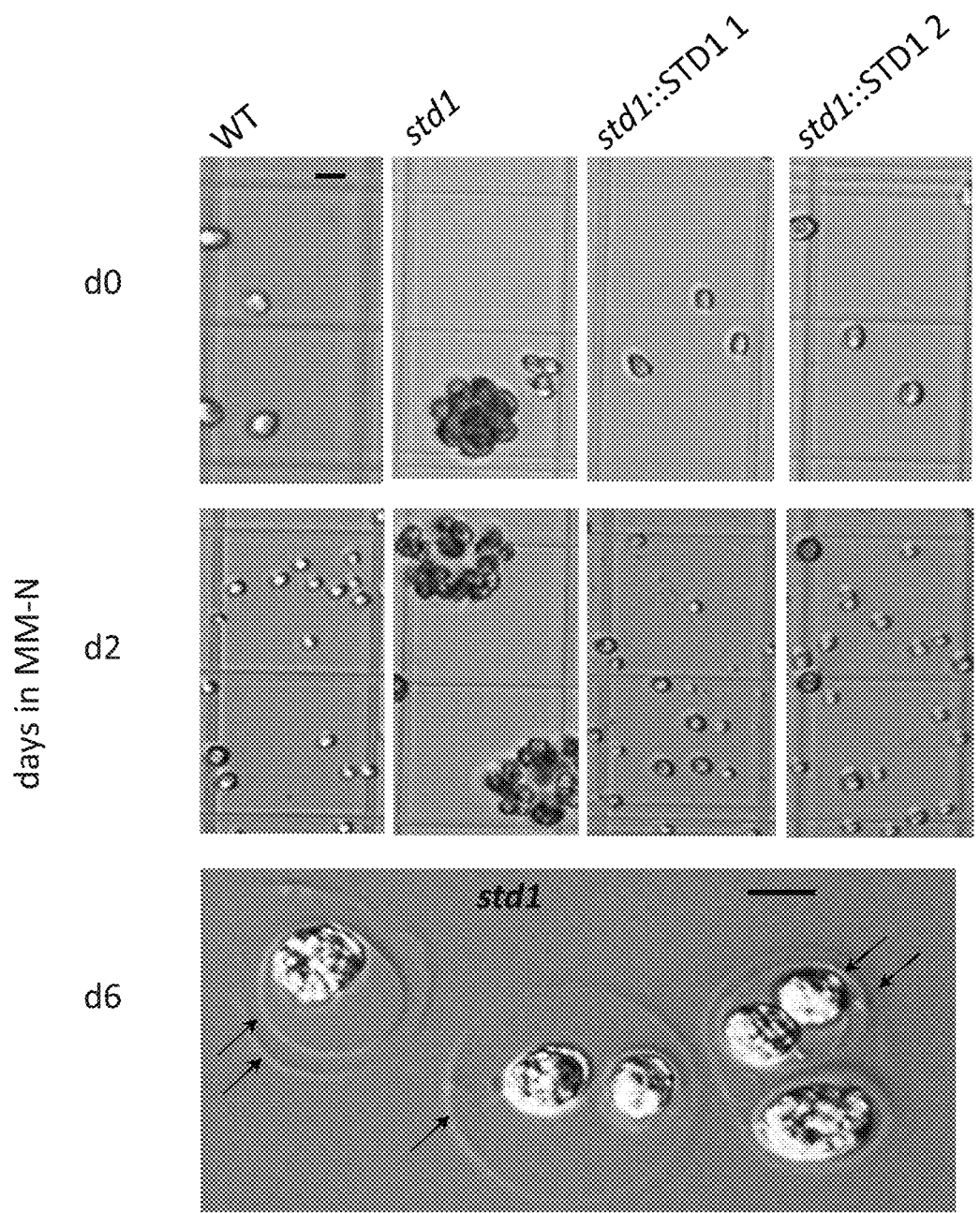
Figure 7B:
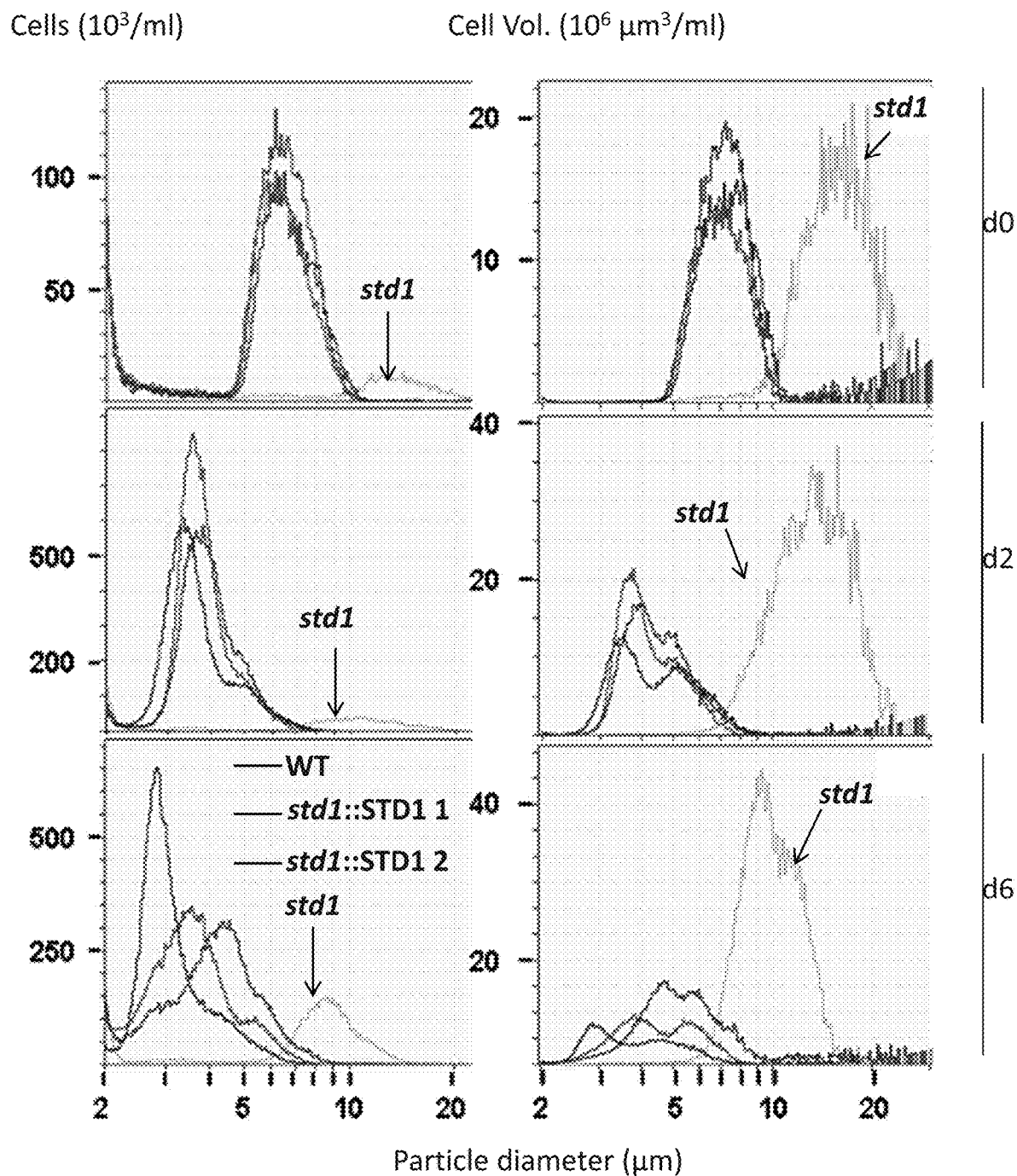
Figure 7C:
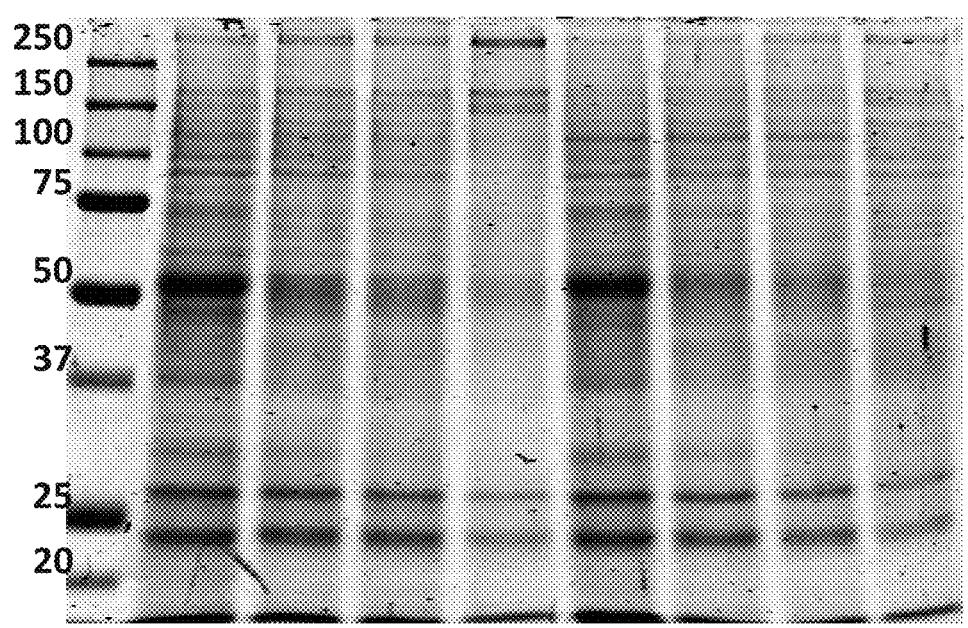

FIGS. 7A through 7C show that std1 mutant cells form aggregates (palmelloids) enclosed by the mother cell wall.

FIG. 7A depicts bright field and differential interference contrast images of wild-type, std1 mutant and complemented (std1::STD1 1 and 2) strains grown in minimal medium and 2% $CO_2$ and then subjected to N deprivation for 0, 2 or 6 days. Arrows indicate mother cell walls. Scale bars=10 µm.

FIG. 7B shows the distribution of cell or aggregate diameter, respectively, and comparison of the cell volume per ml of WT, std1 mutant and rescued strains std1::STD1 1 and 2 in 0, 2 or 6 days MM-N/$CO_2$ condition. Same representative experiment as in FIG. 7A.

FIG. 7C depicts the Commassie blue loading control of the immuno-detection experiment shown on FIG. 4D.

Figure 8A:
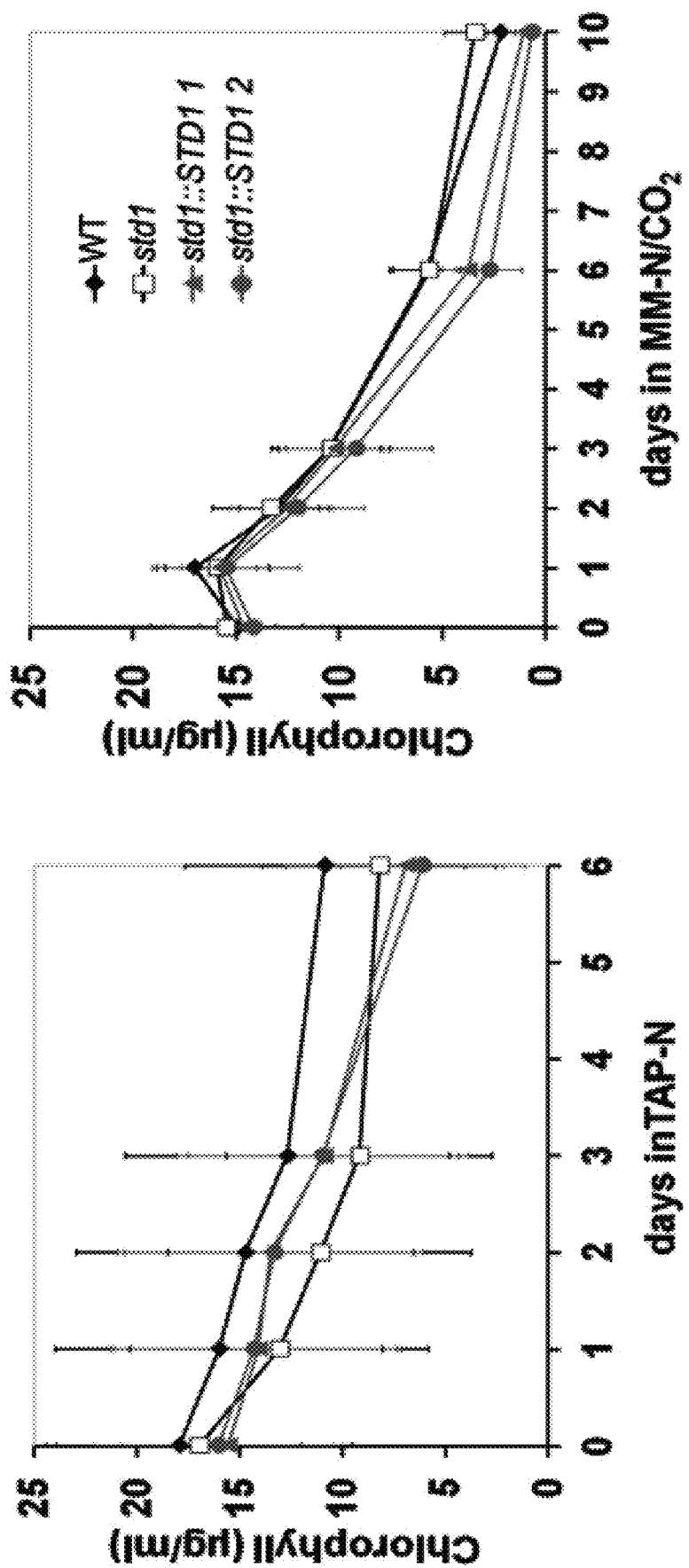
Figure 8B:
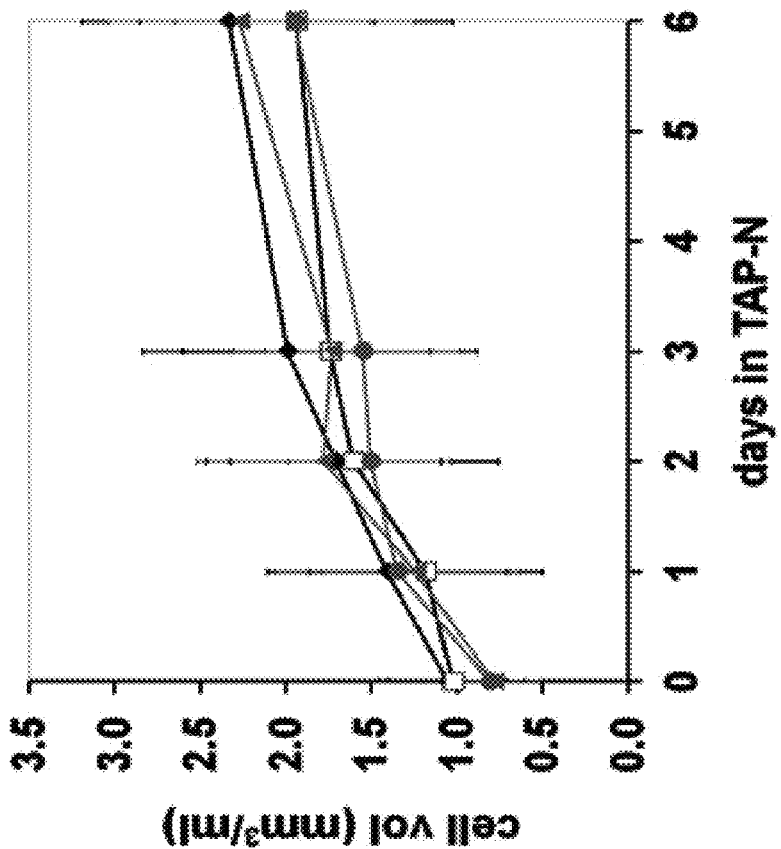
Figure 8B:
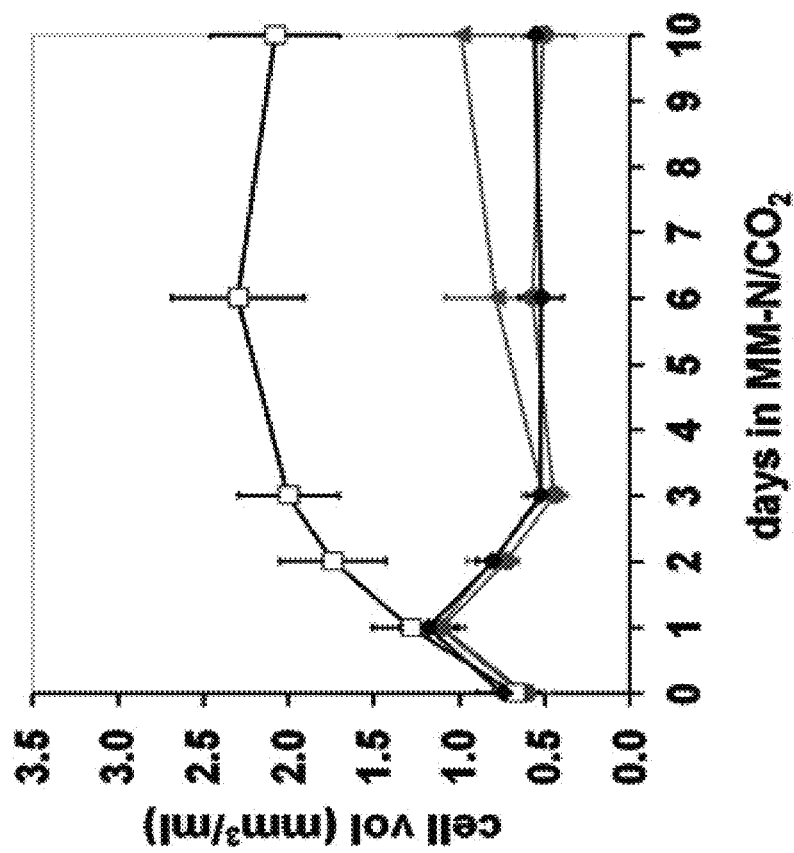
Figure 8C:
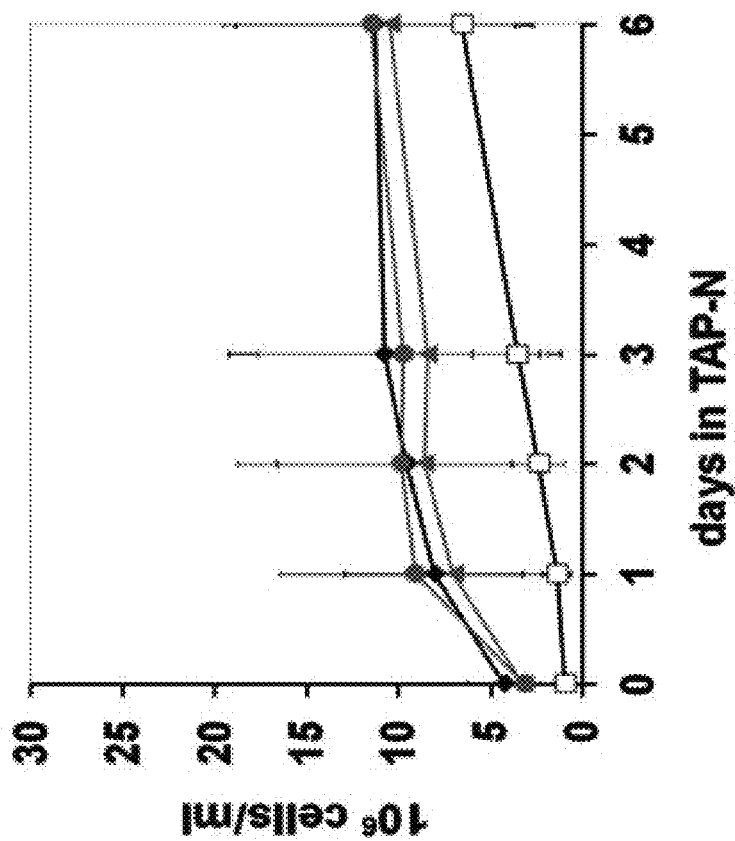
Figure 8C:
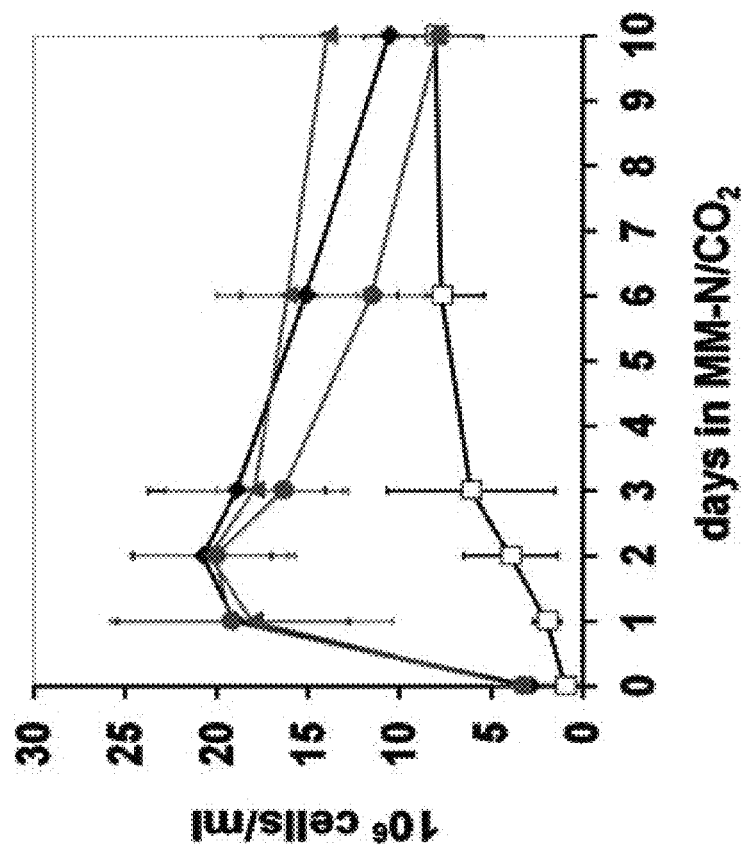

FIGS. 8A through 8C depict the evolution of chlorophyll contents, total cellular volume, and cell number during nitrogen deprivation. Cells were grown in TAP or minimal medium with 2% $CO_2$ in air under a constant illumination of 100 µmol photons $m^{-2}$ $s^{-1}$. At day 0, cells were centrifuged, washed and resuspended in TAP-N (left panels) or MM-N (right panels). Measurements were performed in wild-type (WT), std1 mutant and in two complemented strains std1::STD1 1 and std1::STD1 2.

FIG. 8A depicts the chlorophyll concentration. Shown are means±SD of 5 experiments for TAP-N and 7 experiments for MM-N (3 for 10 d).

FIG. 8B depicts the total cellular volume in $\mu m^3$ $mL^{-1}$, and FIG. 8C depicts the cell or particle concentration per mL which were recorded by Multisizer™ 3 Coulter Counter® (Beckman). Shown are means±SD (n=6 for TAP-N experiments and n=7 for MM-N experiments).

Figure 9A:
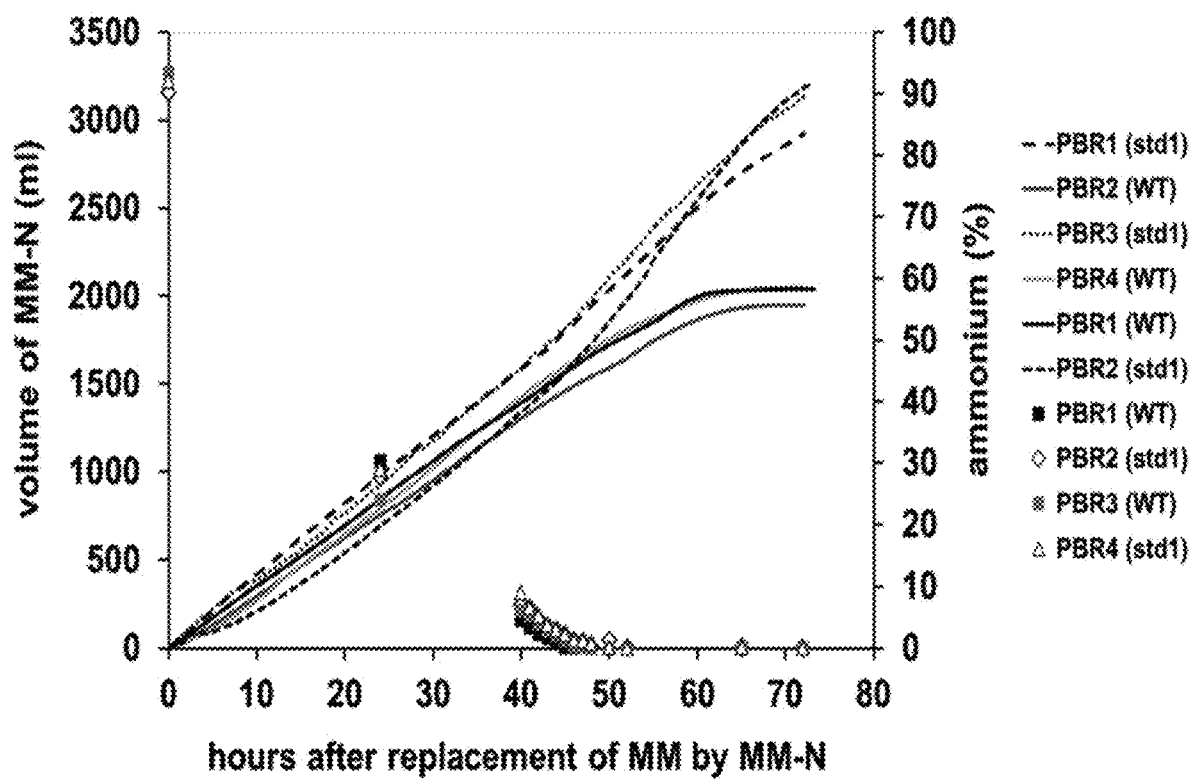
Figure 9B:
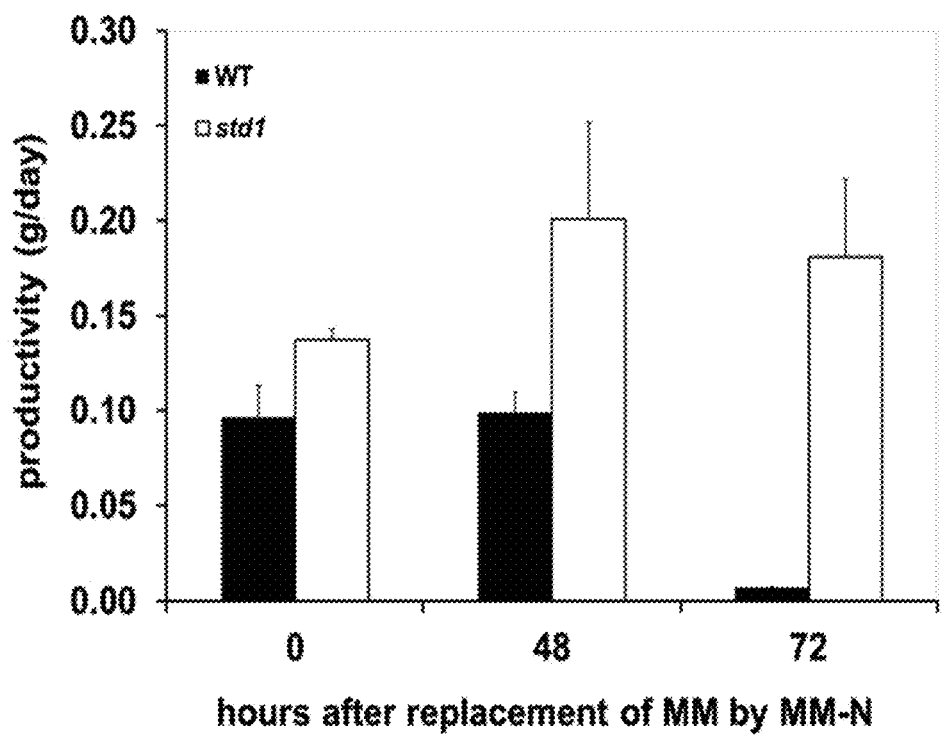

FIGS. 9A and 9B depict the growth performances of std1 and wild-type *Chlamydomonas* cells cultivated photo-autotrophically in 1 L photobioreactors operated as turbidostats during transition from exponential growth to N-deprivation conditions. Cell density was measured using an absorption probe and maintained at a constant level by injection of fresh medium. Due to the aggregation phenotype of std1, $OD_{880\ nm}$ was regulated at different values for WT ($OD_{880\ nm}$=0.4) and std1 ($OD_{880\ nm}$=0.3) to reach similar biomass concentrations (0.15 g dry weight $L^{-1}$) in both cultures. After 48 h of stabilization in the presence of MM under constant illumination (500 µmol photons $m^{-2}$ $s^{-1}$) in the presence of 2% $CO_2$ enriched air, the dilution medium was replaced by MM-N (t0). Measurements of ammonium concentration in the culture medium showed complete exhaustion after 45 h.

FIG. 9A shows the cumulated amounts of fresh medium added to maintain the culture at a constant biomass concentration. Shown are data from three biological replicates for WT and std1 cultures;

FIG. 9B depicts productivity measurements (g dry weight. $d^{-1}$. $L^{-1}$) were determined from at t0, t48 and t72 from dilation rates and biomass measurements. Shown are means±SD (n=3).

Figure 10A:
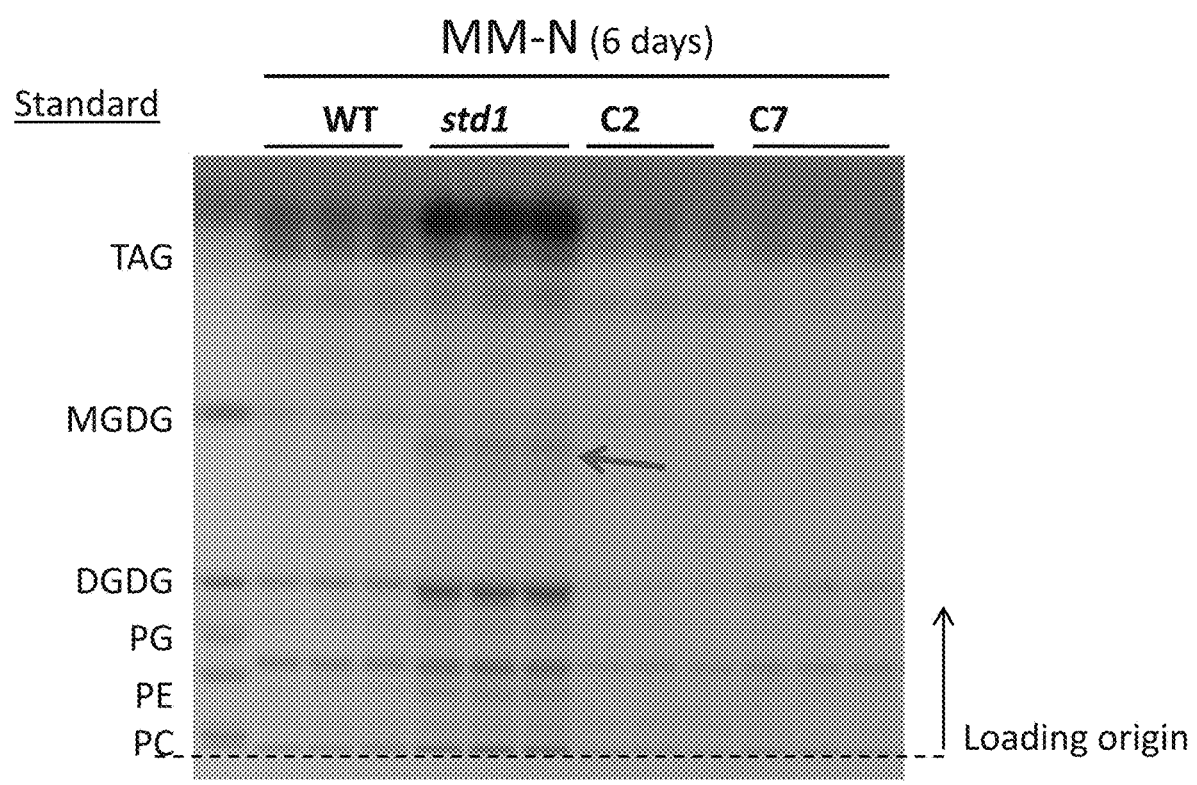
Figure 10B:
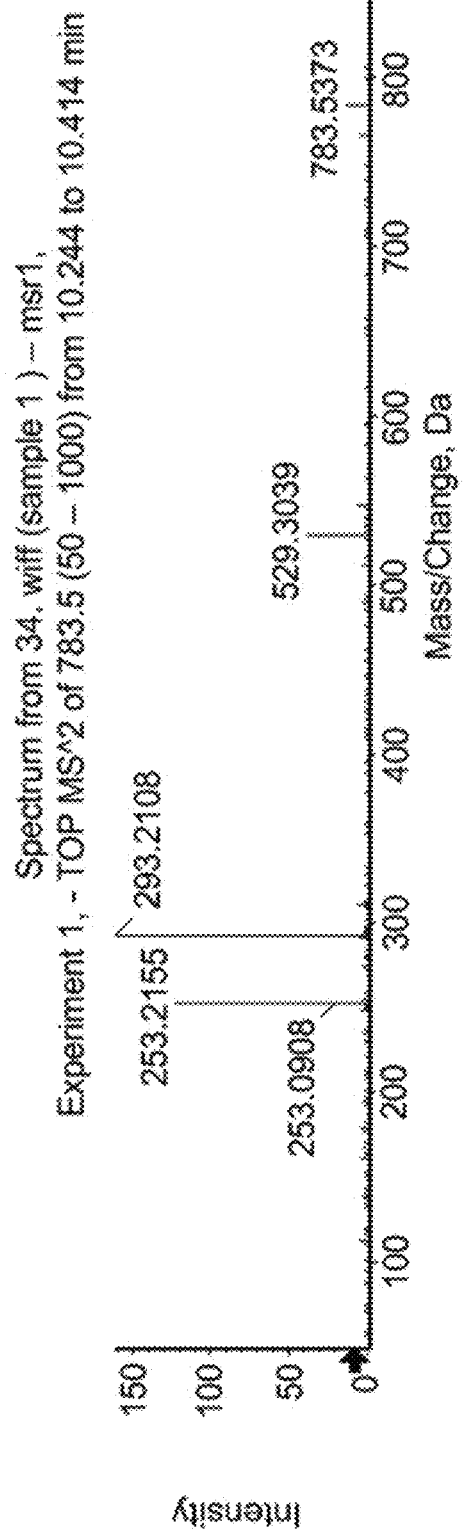

FIGS. 10A and 10B show the formation of oxidized MGDG in the mutant std1.

FIG. 10A shows the over-accumulation of oxidized MGDG species in the std1 mutant detected on the TLC plate.

FIG. 10B shows the structural elucidation of one oxidized MGDG 34 (16:2 O2; 18:1) species accumulating in std1.

Note: C2 and C7 represent two independent complemented lines of the std1 mutant.

Figure 11A:
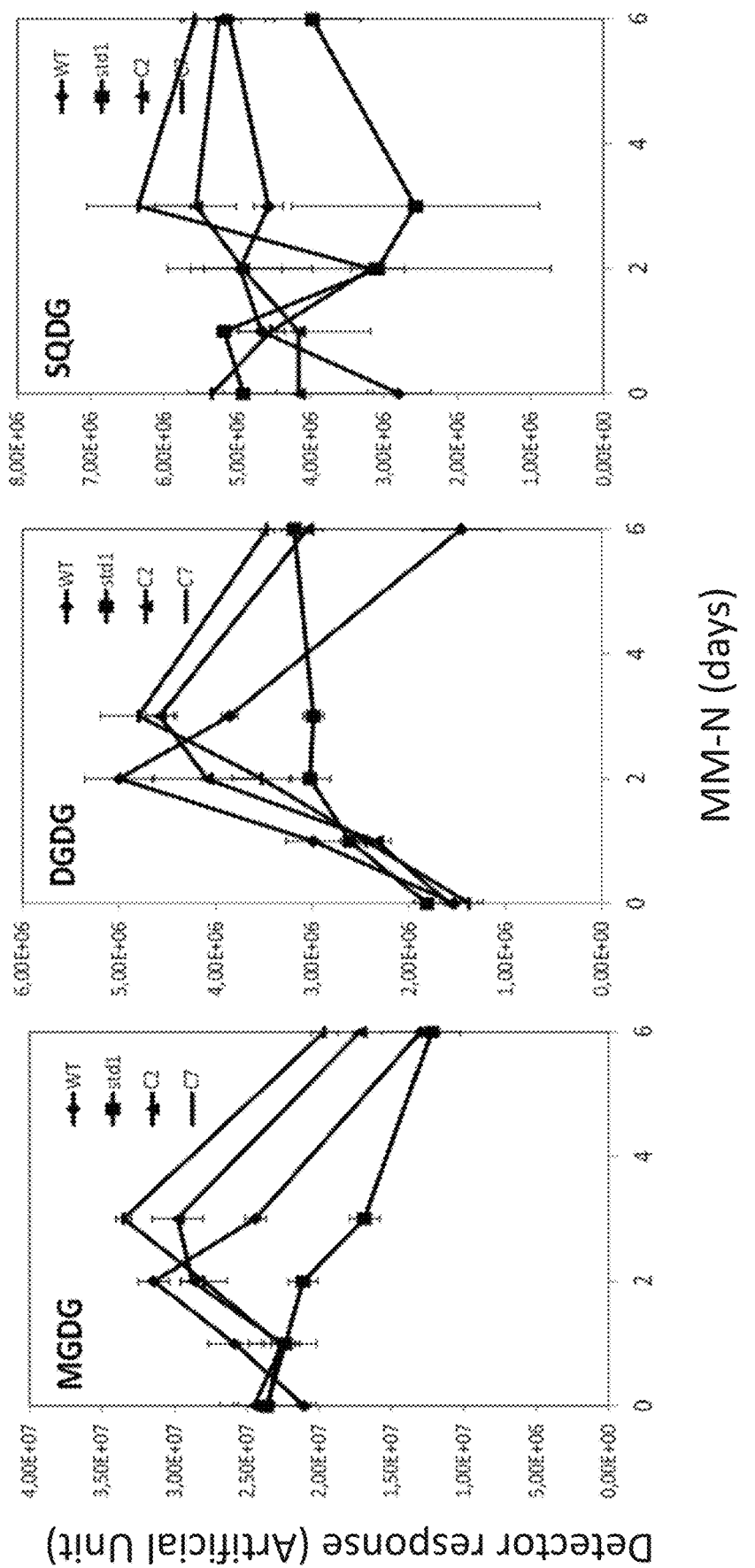
Figure 11B:
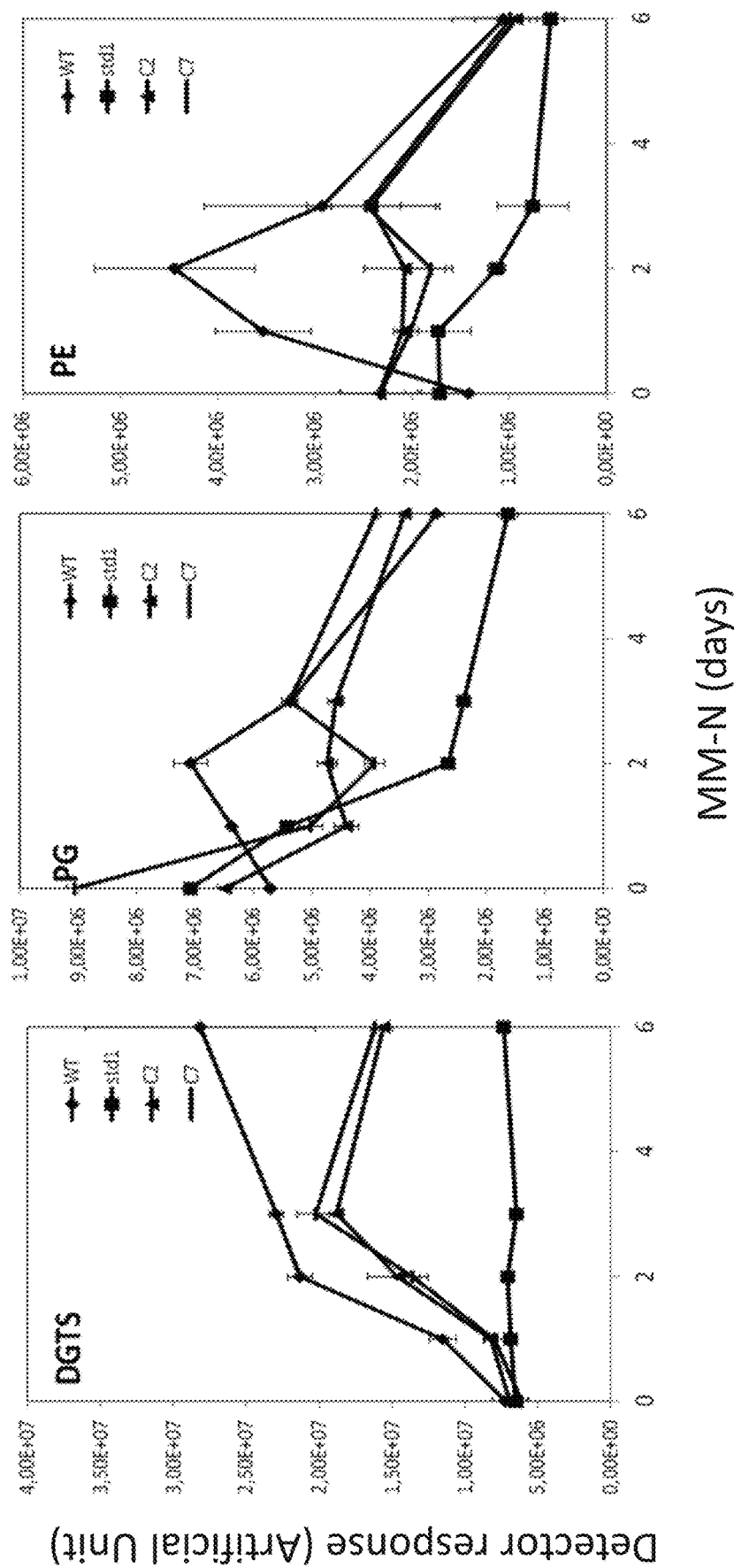
Figure 11C:
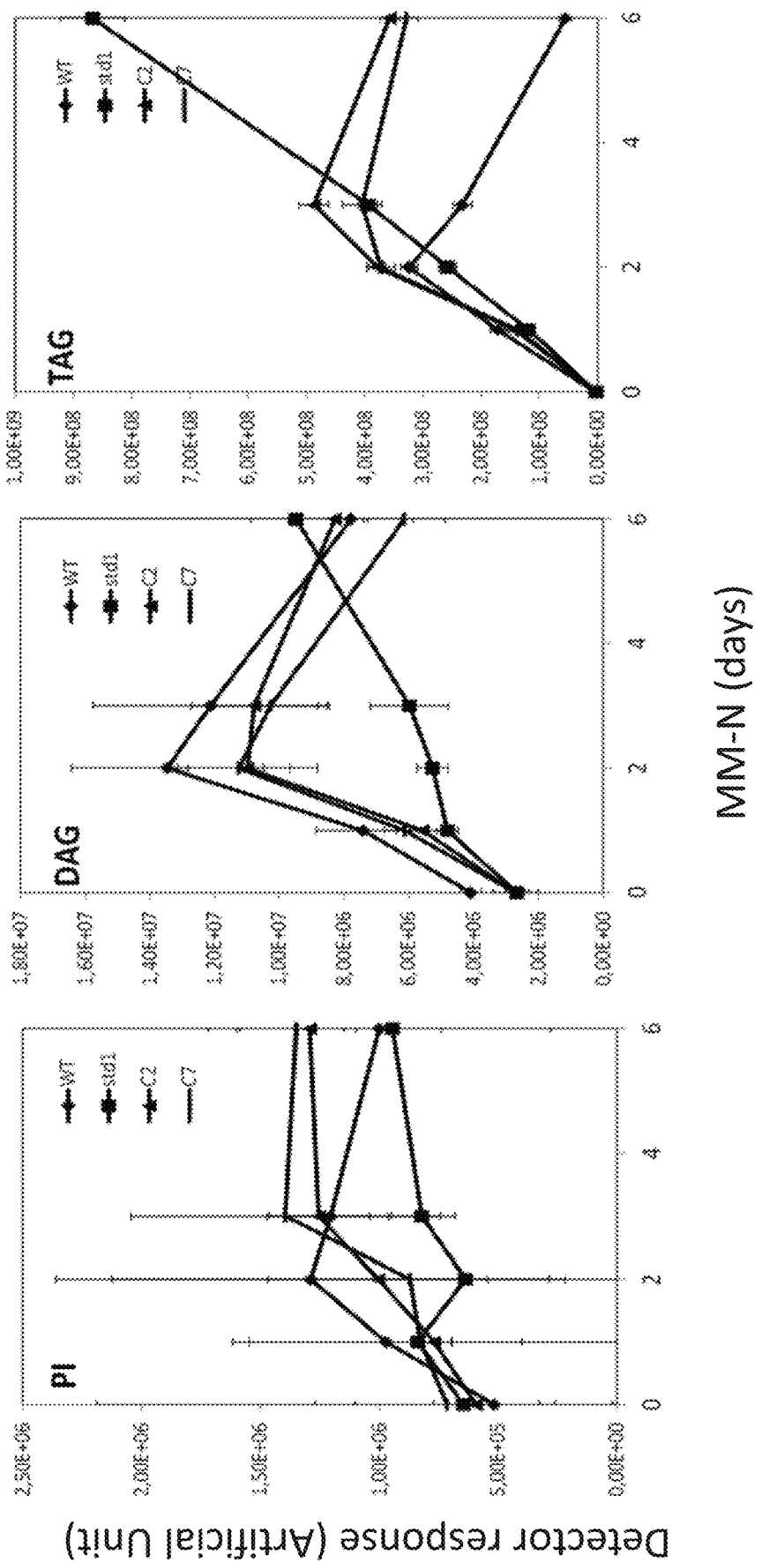

FIG. 11 depicts complete analyses of lipidome in WT, std1 mutant and the two complemented lines in response to nitrogen starvation.

Figure 12A:
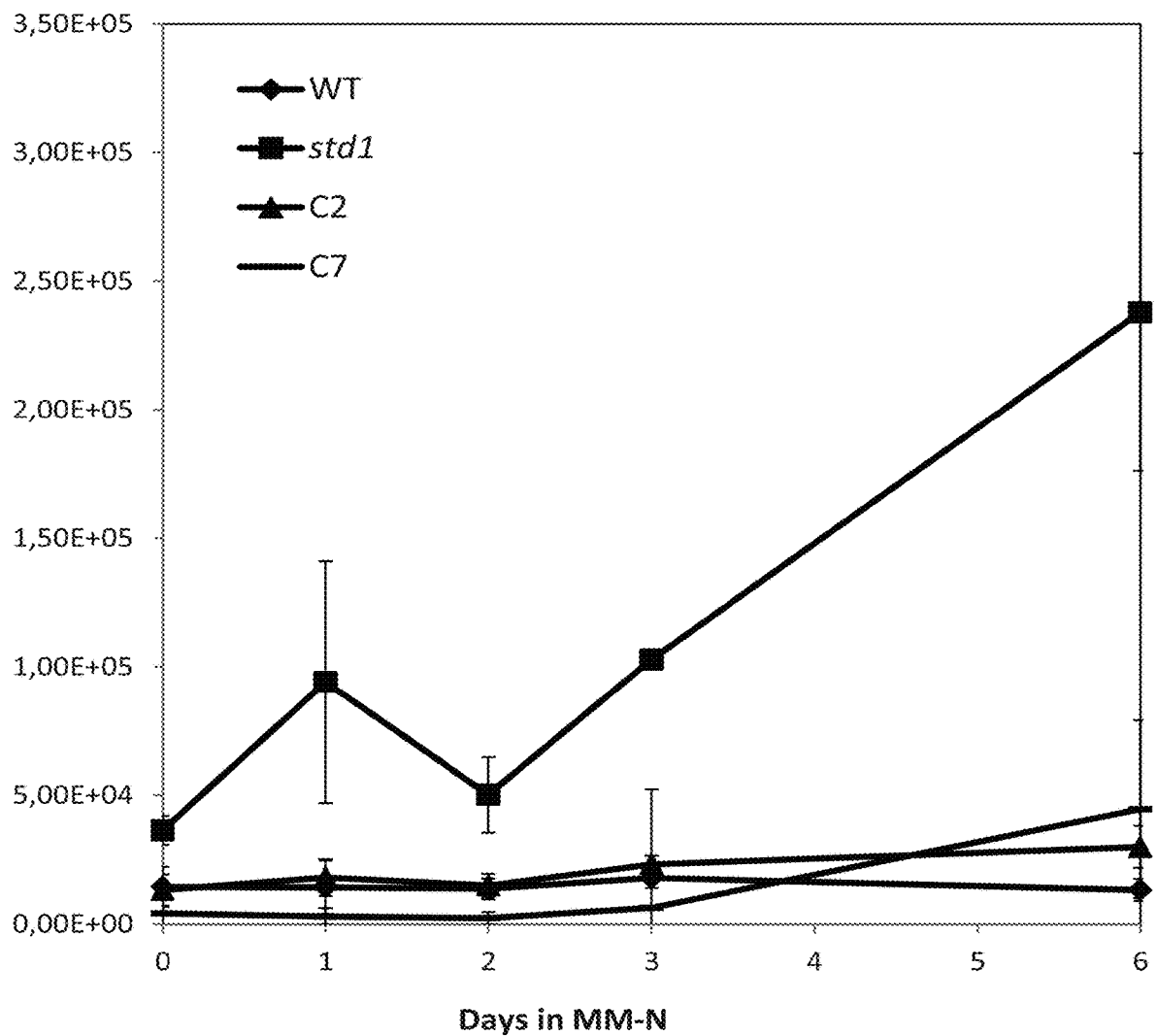
Figure 12B:
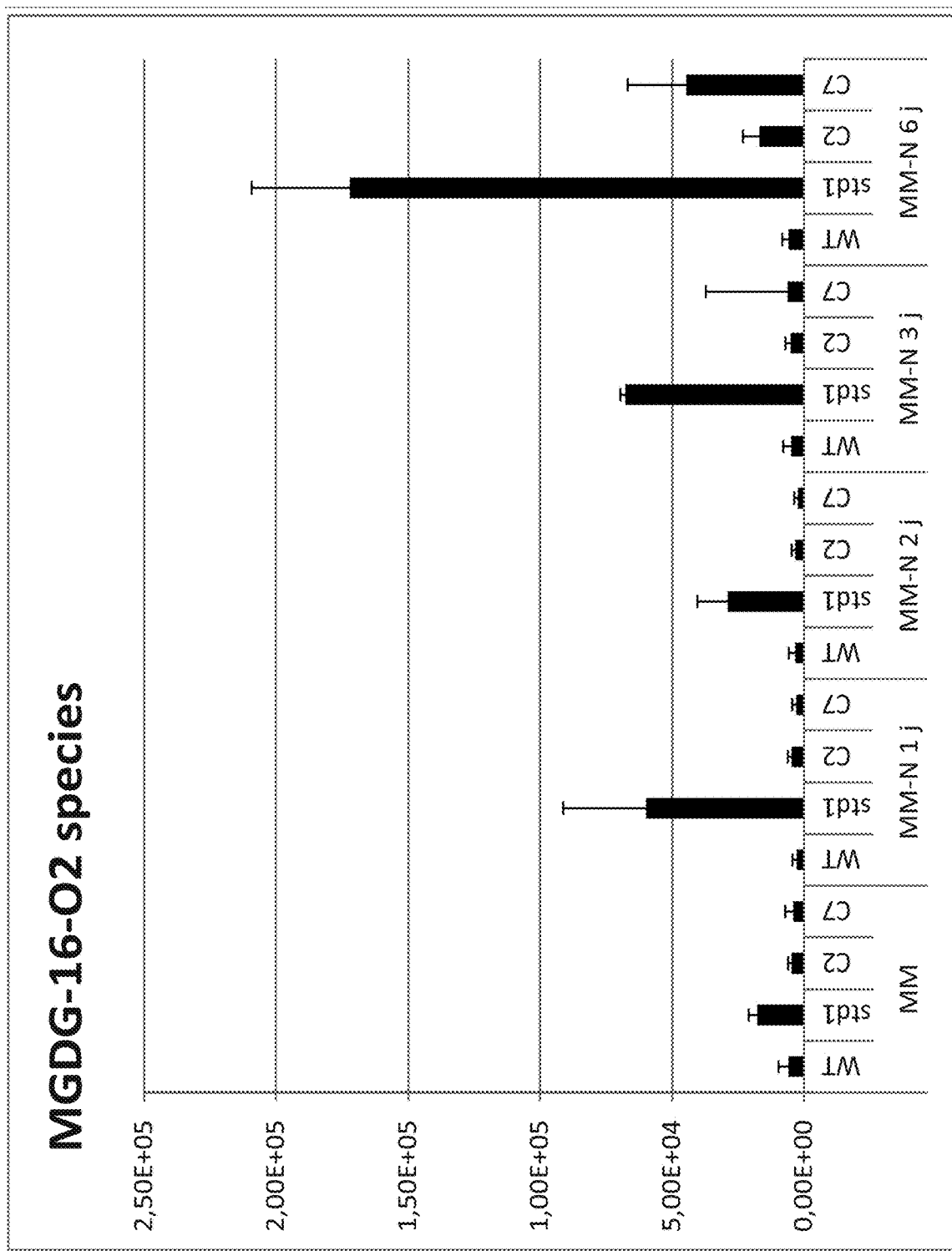
Figure 12B:
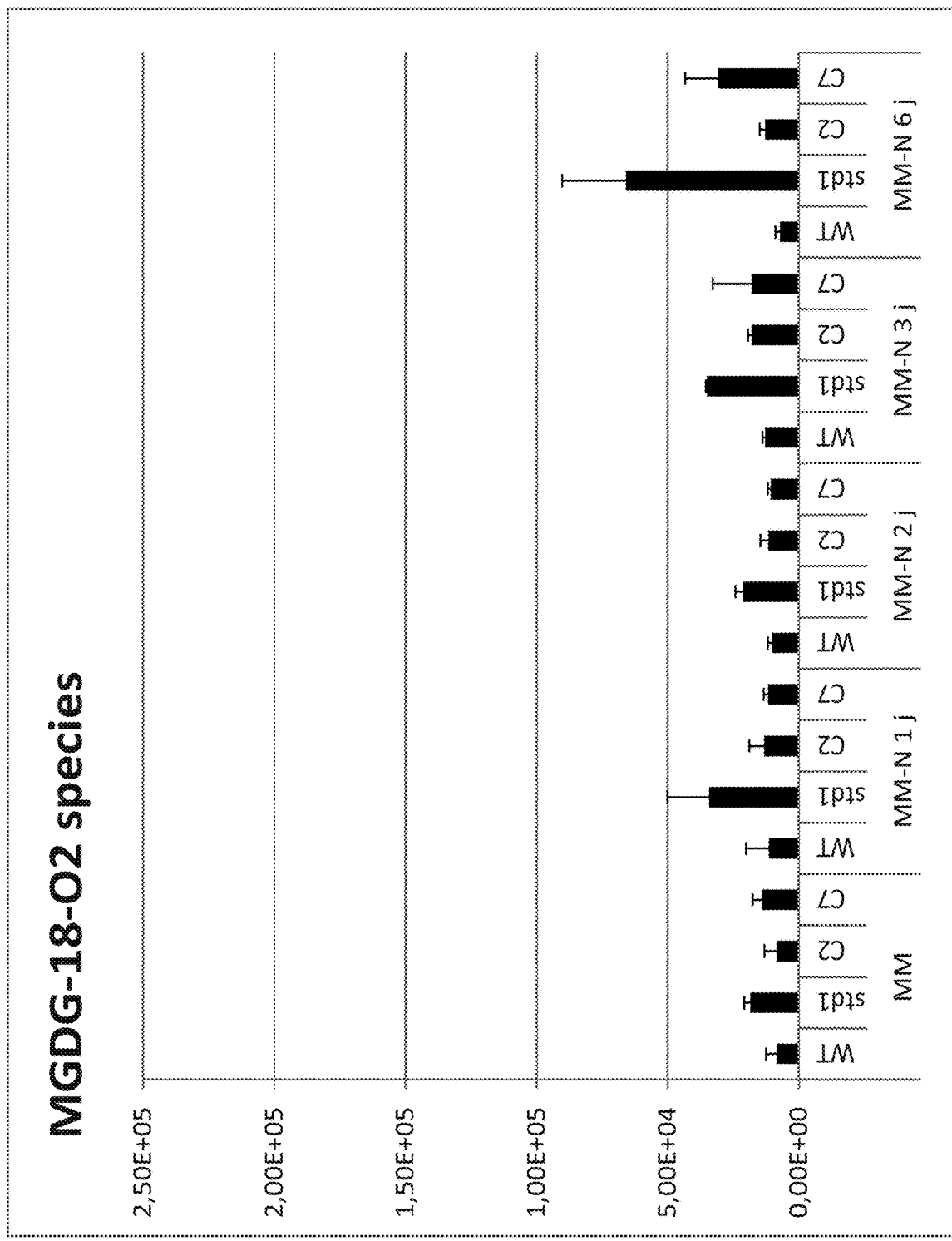

FIGS. 12A and 12B show the over-accumulation of oxidized MGDG in the mutant and its species distribution.

FIG. 12A depicts the total accumulation of oxidized MGDG in response to days of nitrogen starvation in WT, std1 mutant, and two complemented lines.

FIG. 12B shows the molecular species distribution of oxidized MGDG.

Figure 13:
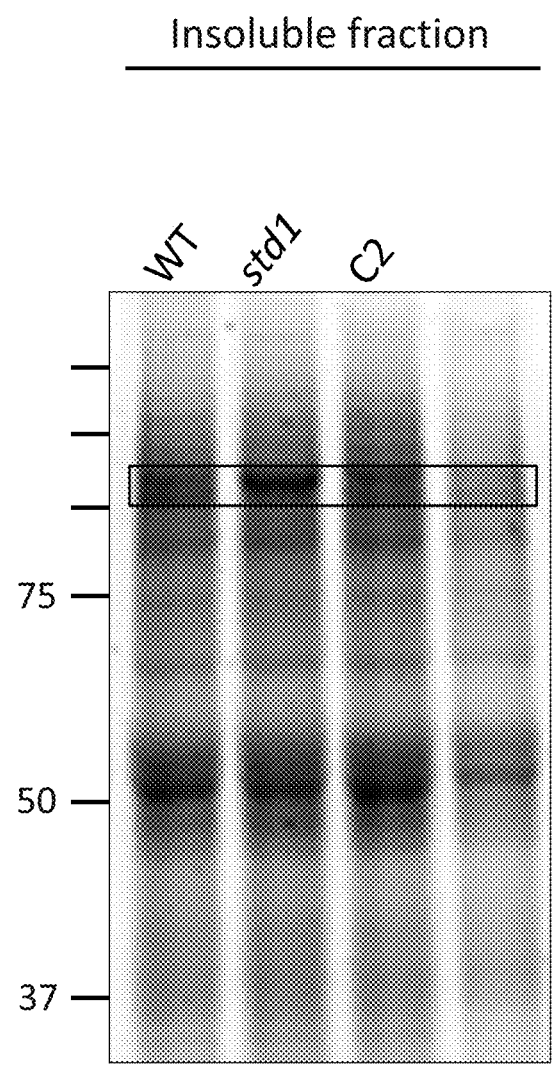

FIG. 13 shows the over-accumulation of a putative lipoxygenase 1 (CreLOX1) in the *Chlamydomonas* mutant std1. An image of SDS-PAGE gel stained by Coomassie blue demonstrating the appearance of a stronger band with a mass of ~110 kDa. Wild-type, the std1 mutant and two independent complemented lines (C2, C7) were grown to exponential phase at standard autotrophic conditions in minimum medium supplied with 2% $CO_2$ at 100 µmol photons $m^{-2}$ $s^{-1}$. After cell lysis, soluble and insoluble proteins were fractionated by ultracentrifugation with a sucrose cushion. Proteins from the pellet fraction containing membranes were resolubilized by addition of Triton X-100, ultracentrifuged and separated on a 10% NuPAGE® Bis-Tris gel. After being stained with Coomassie Brilliant Blue, a strong band was detected in the std1 mutant at ~110 kDa and the corresponding gel regions of all samples were excised and subjected to mass spectrometric analysis.

Figure 14A:
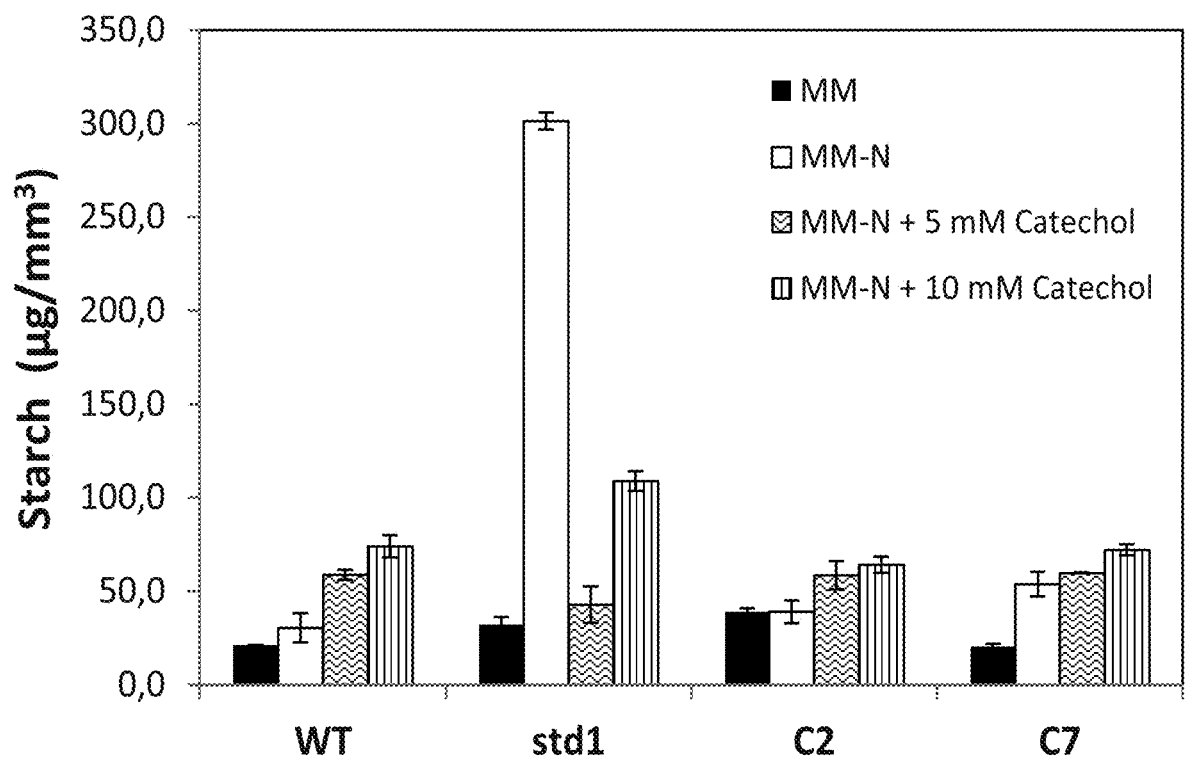
Figure 14B:
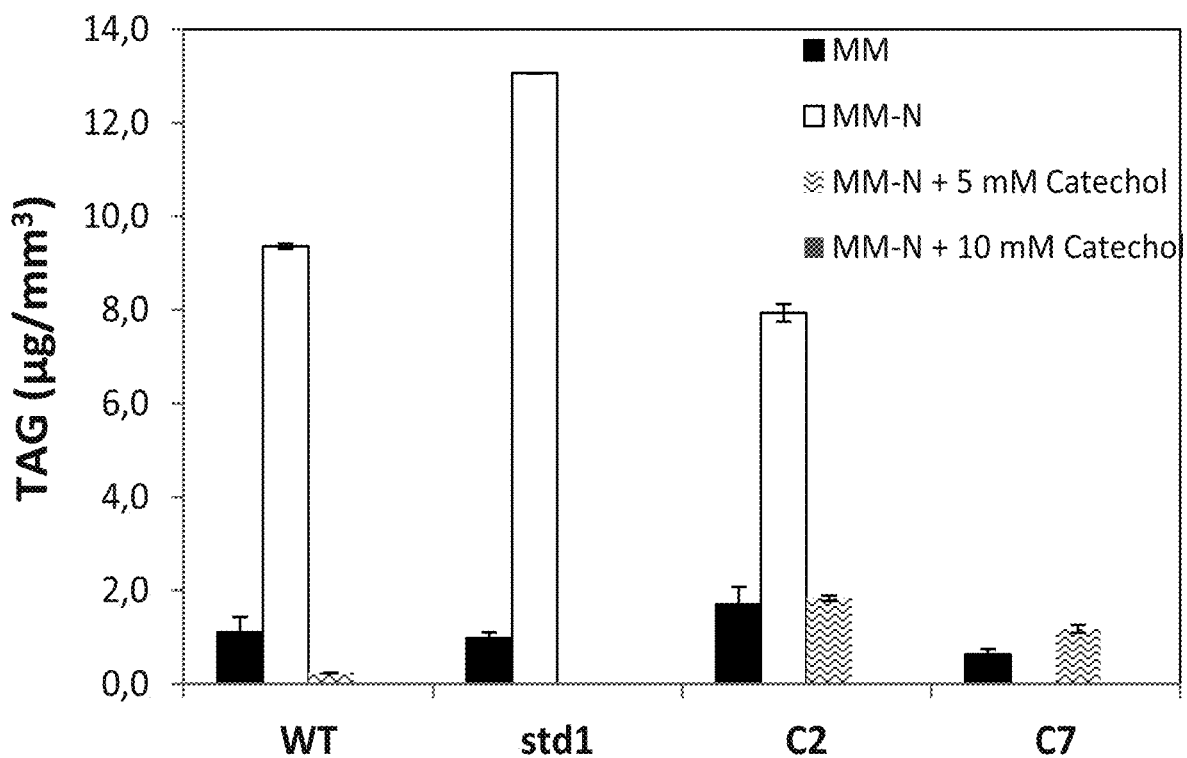

FIGS. 14A and 14B depict the inhibition of TAG and starch accumulation in the mutant by LOX inhibitors.

FIG. 14A depicts starch accumulation.

FIG. 14B depicts TAG accumulation.

EXAMPLES

Example 1: Dual Specificity Tyrosine-Phosphorylation-Regulated Kinase DYRKP-1 Negatively Controls Starch and Oil Accumulation During Nutrient Deprivation in *Chlamydomonas reinhardtii*

Methods

Strains and Cultivation Conditions

As described in (Chochois et al., 2010), the strain CC125 (mt–nit1 nit2) was chosen as genetic background for mutant generation and used as wild-type strain in this study. The mutant strain std1 was generated by transformation with KpnI-linearized plasmid pSL-X harboring the paromomycin resistance cassette AphVIII. In the case of std1, only a ~1900 bp-fragment of the ~4800 bp-pSL-X was inserted into the genome. Cells were grown mixotrophically in Tris-acetate-phosphate (TAP) medium (Harris, 2009) in an incubator shaker at 25° C., under continuous light at ~100 µE $m^{-2}$ $sec^{-1}$. For deprivation experiments, precultures were grown mixotrophically in TAP medium or photoautotrophically in a MOPS-buffered minimal medium (Harris, 2009) and 2% $CO_2$ in the air to a density of 2-5×10$^6$ cells $mL^{-1}$. After taking samples at t=0, the culture was centrifuged at 25° C. and 1789 g for 4 min, the cell pellet was washed once and resuspended in N- or S-deprived medium. It should be noted that an ideally identical initial cell density of the cultures is critical to get comparable data for all studied strains. Because of palmelloid formation of std1 total cellular volume per mL or chlorophyll content was compared to adjust the cultures before starvation.

Genetic Characterization and Complementation of the Mutant Strain Std1

To check the integration frequency of the inserted DNA, Southern blot analysis was performed with wild-type and std1 mutant cells. Genomic DNA was prepared as described previously (Tolleter et al., 2011), and 4, 6 or 8 µg genomic DNA restricted with NotI were separated in an 0.8% agarose gel, blotted on a nylon membrane and hybridized with a digoxygenin-labelled probe complementary to part of the AphVIII gene of the inserted resistance cassette. A PCR DIG Probe Synthesis Kit (Roche) was utilized for probe labelling using primers 5'-CGAAGCATGGACGATGCGTT-3' (SEQ ID NO: 4) and 5'-CGAGACTGCGATCGAACGGACA-3' (SEQ ID NO: 5). The hybridization with the resulting 400 bp-PCR fragment was performed overnight at 50° C. using DIG Easy Hyb™ buffer (Roche). Anti-Digoxigenin-AP and CSPD as substrate (Roche) were applied to detect signals using G:BOXChemin XL (Syngene). In order to determine the site of integration of the paromomycin resistance cassette, genome walking was performed according to the GenomeWalker Kit from Clontech. Genomic DNA of the strain std1 was digested with FspI and processed appropriately according to the manufacturer's instruction. The sequences 5'-CTGGTGCTGCGCGAGCTGGCCCAC-GAGGAG-3' (SEQ ID NO: 6) (GPS1) and 5'-TGGT-TCGGGCCGGAGTGTTCCGCGGCGTT-3' (SEQ ID NO: 7) (GPS2) served as gene-specific primers allowing the determination of the genomic sequence downstream of the inserted Aph VIII cassette. The Advantage GC genomic LA polymerase (Clontech) was used for amplification reactions. For complementation of the strain std1, a PCR reaction was carried out on genomic wild-type DNA using primers 5'-GTCTAGAATGTCGCTCCGCCTGAACCGATG-3' (SEQ ID NO: 8) (XbaG4forHyg) and 5'-GTCTAGACTA-CATGCTGTCGAGCGAGG-3' (SEQ ID NO: 9) (XbaG4RevHyg) and the DyNAzyme™ EXT DNA Polymerase (FinnzymesOy). The amplified 6913 bp coding for the DYRKP-1 gene were restricted by XbaI and cloned into XbaI-digested vector pSL-Hyg, originating from pSL18, (Dauvillee et al., 2003) under control of the PSAD promoter and carrying a resistance cassette for hygromycin (Berthold et al., 2002). std1 cells were transformed with KpnI-linearized pSL-Hyg-STD1 by agitation with glass beads (Kindle, 1990), selected on 20 mM hygromycin and then screened applying the same protocol as for isolating the mutant strain (Chochois et al., 2010). Transformants were exposed for several days to S or N deprivation, transferred to minimal medium and subjected to darkness followed by iodine staining to test for remaining starch levels.

Phylogenetic Analysis

Amino acid sequences were aligned using MAFFT version 6 software (Katoh et al., 2002). Next, the resulting alignment was manually refined using SeaView version 4 (Gouy et al., 2010) and regions where homology was doubtful were removed from further analysis. A total of 313 amino acid positions were kept for the phylogenetic analysis of DYRK proteins. Phylogentic analyses were conducted using Neighbour-Joining (NJ), Maximum Likelihood (ML) and Parsimony (Pars) approaches in the Phylogenetic Inference Package Phylip version 3.69 (Folenstein et al., 2005). The PROTML program was used for ML analysis and the sequence input order was randomized (20 jumbles). The SEQBOOT and CONSENSE programs were used for bootstrap value calculations on 100 replications and consensus tree reconstructions, respectively. To examine the confidence of nodes, NJ and Pars analysis were done using NEIGHBOR and PROTPARS programs. Distance matrices used for the NJ analysis were created with the PROTDIST program. The phylogenetic trees were drawn with MEGA5 (Tamura et al., 2011).

RNA Analyses and RT-PCR

Total RNA was isolated as described in (Liu et al., 2005). For RT-PCR reactions 1 µg of DNaseI-treated total RNA was employed for application of the OneStep RT-PCR Kit (Qiagen). To obtain sequence information of the complete transcribed DYRKP-1/STD1 gene, three overlapping RT-PCRs were performed using primer pairs 5'-CATAGTGCTCAGCAGGGGACAAGGC-3' (SEQ ID NO: 10) (Std1UTR1) and 5'-AGCGTGCCAGAGGTTTCGCCGTC-3' (SEQ ID NO: 11) (Std1P3rev), 5'-CCGCGGACGGCGAAACCTCTGGCAC-3' (SEQ ID NO: 12) (Std1FW2) and 5'-GATCTCGTCCAGCGACTGGTCAAAGTAG-3' (SEQ ID NO: 13) (G4rev14), and 5'-GCGGATCCGACGAGCAGGGCAACGTGCTG-3' (SEQ ID NO: 14) (ACG4_FW3) and 5'-CGGCAAGCTTCTACATGCTGTCGAGCGAGG-3' (SEQ ID NO: 15) (ACG4_Rev1), the latter primer pair was initially created to express the corresponding region as antigen. For comparison of transcript levels in wild-type, mutant and complemented strains, the primer pairs Std1FW2 and G4rev14 were used to amplify part of the DYRKP-1 transcript. Specific primers were designed for an actin (Locus name Cre13. g603700, Protein ID 515031), serving as constitutively expressed control gene (5'-AATCGTGCGCGACATCAAGGAGAA-3' (SEQ ID NO: 16) and 5'-TTGGCGATCCACATTTGCTGGAAGGT-3' (SEQ ID NO:17)).

Northern Blot Analyses

For RNA extraction, 15 mL of cell cultures at relative time points were collected on ice, centrifuged for 1 min at 1789 g and the 500 µL-cell suspension was transferred to 1.5 mL-tube on ice and mixed with 500 µL of RNA lysis buffer. RNA extraction, separation on formaldehyde agarose gels and Northern blot were performed as described in (Liu et al., 2005). Membranes were hybridized with DNA probes containing a fragment of the STD1 gene or CBLP2 gene as a loading control. A 1. pAC-STD1 plasmid was obtained by a ligation of the BamHI-HindIII-restricted vector pQE-30 (Qiagen) and a BamHI-HindII-restricted RT-PCR product coding for the 3'-part of DYRKP-1. RT-PCR was carried out using the primers 5'-GCGGATCCGACGAGCAGGGCAACGTGCTG-3' (SEQ ID NO: 14) (ACG4_FW3) and 5'-CGGCAAGCTTCTACATGCTGTCGAGCGAGG-3' (SEQ ID NO: 15) (ACG4_Rev1), giving rise to a 1116 pb product. 1-kb BamHI-HindIII fragment from this pAC-STD1 plasmid, and the 1-kb cDNA of CBLP2, were used for hybridization. Radioactive signals were detected using BAS-IP MS2040 phosphorimager plates (Raytest), scanned with a Molecular Imager FX phosphorimager (Bio-Rad), and imaged using the Quantity One-4.5.1 program (Bio-Rad).

Genomic DNA Analysis

To determine genomic DNA concentration during nitrogen deprivation time course experiments, cells equivalent to 1.2 $mm^3$ total cellular volume on average were harvested by centrifugation and stored at −80° C. Genomic DNA of two replicate samples for each time point was prepared by phenol-chloroform extraction as described previously (Tolleter et al., 2011). DNA concentrations were measured using a NanoDrop™ 2000 Spectrophotometer (Thermo Scientific).

Protein Preparation, Quantification and Immunoblot Analysis

For the detection of DYRKP-1, soluble cell lysates were prepared as follows: 100 mL of C. reinhardtii cell cultures in the exponential phase (eq. to $5 \times 10^6$ cells/mL or 0.8 $mm^3$/mL) were harvested by centrifugation for 2 min at 1789 g and resuspended in 1 mL lysis buffer (20 mM HEPES-KOH pH 7.2, 10 mM KCl, 1 mM $MgCl_2$, 154 mM NaCl, 0.1× protease inhibitor cocktail; Sigma P9599). Cells were sonicated on ice for 90 sec with a setting of 1 sec pulse/1 sec pause. Lysates were loaded onto a sucrose cushion (20 mM HEPES-KOH pH 7.2, 0.6 M sucrose) and centrifuged in a MLA-55 rotor (Beckman Coulter) for 30 min at 151 300 g and 4° C. Soluble proteins were mixed with one volume of 2× sample buffer (Schulz-Raffelt et al., 2007) or 2×LDS sample buffer (Invitrogen) and heated for 5 min at 95° C. or 10 min at 70° C. prior to loading on an 8% SDS-polyacrylamide gel. Western blotting was carried out for 1:45 h to detect the expression of DYRKP-1 by ECL (SuperSignal West Pico Chemiluminescent Substrate, Thermo Scientific), using a purified peptide antibody (Proteogenix). Protein samples taken during nitrogen starvation kinetics were treated as follows: cell pellets equivalent to 1.2 $mm^3$ total cellular volume on average were stored at −80° C. until use. Total proteins of two replicate samples at each time point were extracted in 70 µL buffer containing 50 mM Tris pH 8, 10 mM EDTA and 2% SDS for 30 min at RT, followed by a 2-min cold centrifugation. To quantify protein concentrations, 2 µL of protein extracts were analyzed by colorimetric measurements with bicinchonic acid (Pierce BCA Protein Assay kit, Thermo Scientific). For immunoblot analysis, 10-12 µg of total protein extracts were separated on 10% SDS-polyacrylamide gels, transferred to BioTrace™ NT nitrocellulose membrane (Pall Life Sciences) and analyzed by immunodecoration with antibodies against AtpB, RbcL, CytF, PsbD (D2) (Agrisera) and HSP70B (Schroda et al., 1999). The DYRKP antibody was obtained by immunization of two rabbits with two synthesized peptides (DG-MDDPGYSRKEVPNP-cys (SEQ ID NO:25) and PAVN-HEDVELFRN-cys (SEQ ID NO:26)) conjugated to KLH (keyhole limpet hemocyanin) as carrier protein (Proteogenix).

Starch and Chlorophyll Measurements

The starch and chlorophyll contents were measured according to (Chochois et al., 2010). One mL of culture was harvested, centrifuged at ~20,000 g for 10 min, resuspended in 1 mL of methyl alcohol for chlorophyll extraction and stored at −80° C. The pellets were dried, and 400 µL of water were added. To solubilize starch, the samples were autoclaved setting "dry cycle". Subsequently, starch was degraded to glucose by adding 200 µL amyloglucosidase solution (1 U/mL, Roche) and incubation at 55° C. for 1-2 h. Using an automated sugar analyzer (Ysi model 2700 select, Yellow Springs, Ohio, USA), glucose concentration were determined. Chlorophyll was extracted by methanol, and chlorophyll a and b were determined by measuring the absorbance at 653, 666 and 750 nm using UV-VIS spectrophotometer (SAFAS UVmc2 with the software SP2000).

Oil Content Quantification

C. reinhardtii cells (eq. to 2 $mm^3$ total cellular volume) were harvested by centrifuge at 1000 g for 2 min (at 4° C.). The cells were either frozen right away under −80° C., or quenched in hot isopropanol for immediate lipid extractions. Total cellular lipids were extracted using a mixture of hexane and isopropanol (Li-Beisson et al., 2010). Organic solvent phase containing total cellular lipids were collected and dried under a stream of nitrogen gas, then resuspended into 200 μL chloroform:methanol (2:1, v/v). Triacylglycerols (TAG) were first separated from other lipid classes on thin layer chromatograph, charred with 2% $CuSO_4$ dissolved in 8% $H_3PO_4$ in water, then TAG content was calculated based on a densitometry method after being compared to a standard curve generated with a C17:0 TAG standard (Siaut et al., 2011).

Chlorophyll Fluorescence

Chlorophyll fluorescence was measured using a Dual Pam-100 (Heinz Walz). Samples were placed into a cuvette under constant stirring at room temperature and dark-adapted for 5-10 min before measurement. Light Curves were recorded with ten illumination steps ranging from 15 to 715 μmol $m^{-2}$ $s^{-1}$ PAR, each light intensity was kept for 30 s following a saturating flash to measure Fm'. ETR was calculated as described previously (Rumeau et al., 2005).

Biomass Determination

To determine biomass accumulation of a culture, at each time point three 5 mL-samples were dropped on glass fiber filter on disposable aluminum dishes (VWR, Ref. 611-0739 and -0741) and dried overnight in an oven at 80° C. Three 10 mL-samples of the medium were treated equally. The paper filters were weighed before and after adding cells and the mean value for the medium was subtracted.

Microscopy

For light microscopy, a Leica DMRXA microscope was used (Leica Microsystems, Germany). Cells were fixed with 0.25% glutaraldehyde in the medium, if necessary. To compare cell concentrations easily, a Neubauer chamber was used. Images were captured with the Spot Insight 4 software (Diagnostic Instruments Inc., Sterling Heights, USA; the SpotImaging website).

Results

Identification and Genetic Characterization of the Starch Degradation Mutant std1

Figure 1A:
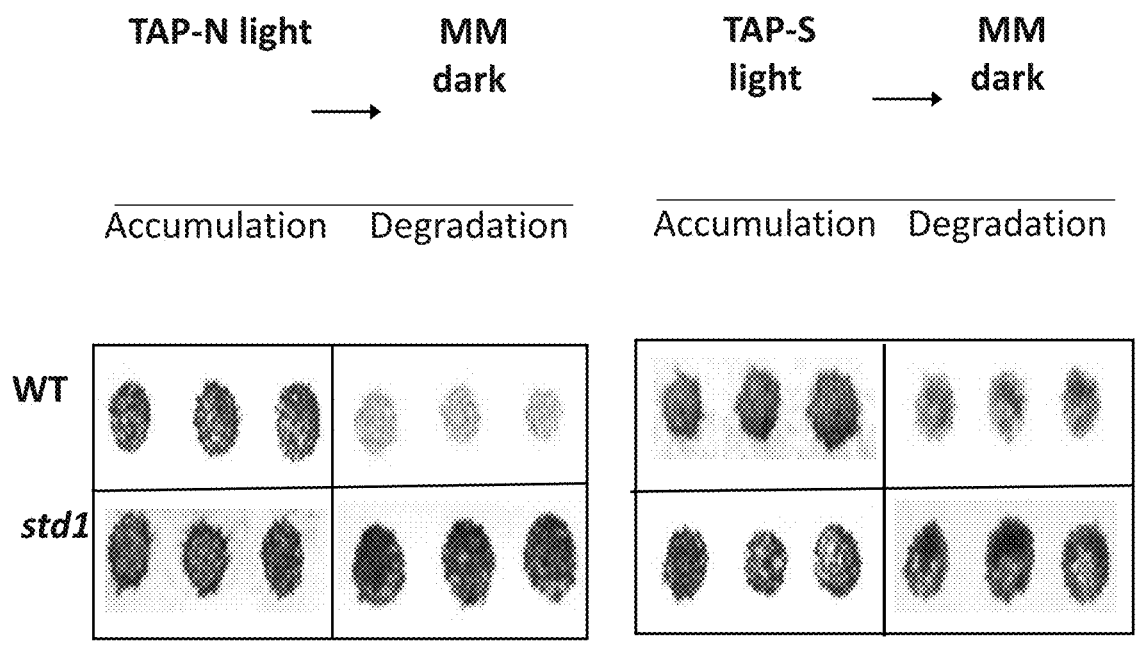
FIG. 1C depicts DYRKP-1 gene expression analyzed by RT-PCR in wild-type, std1 and two complemented strains (std1::STD1 1 and 2) grown in TAP. Actin was used as a control gene.
FIG. 1D depicts DYRKP-1 protein expression analyzed by immuno-detection in soluble protein lysates from photoautotrophically grown cells separated on an 8% SDS-polyacrylamide gel.
Figure 1B:
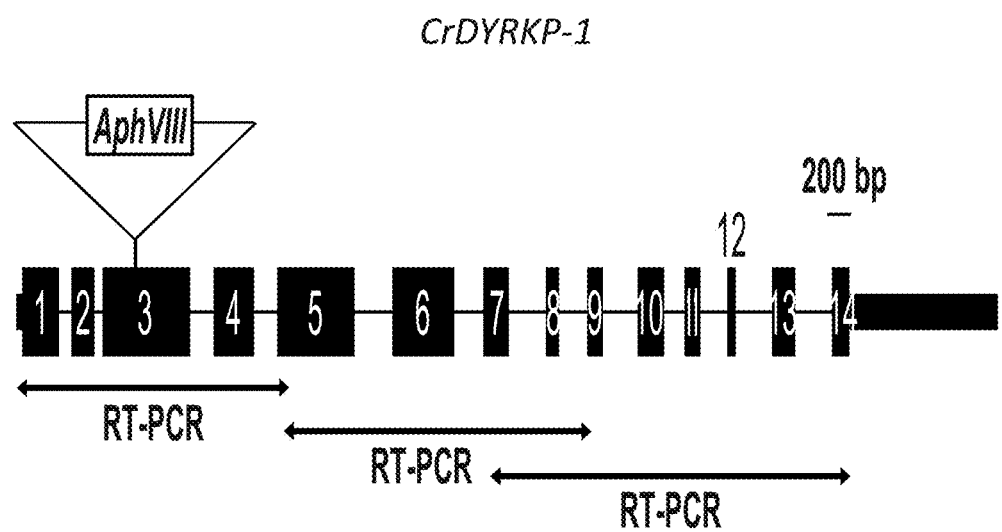

From the screening of a DNA insertional library created by transformation of the C. reinhardtii wild-type strain CC125 with a paromomycin (AphVIII) resistance cassette, several mutants affected in starch degradation were previously isolated (Chochois et al., 2010). One of these mutants, called std1 for starch degradation 1, showed a slower rate of starch degradation in the dark compared to its wild-type progenitor (FIG. 1A). Southern blot analysis indicated a single integration of the paromomycin cassette into the mutant genome (FIG. 2A). Sequencing of DNA flanking regions showed insertion of the AphVIII cassette within the third exon of a gene, annotated as Dual-Specificity Tyrosine-Phosphorylated Protein Kinase DYRK2 (Chlamydomonas genome version 4.0), and renamed here DYRKP-1 (FIG. 1B). The Chlamydomonas DYRKP-1 gene model was confirmed by sequencing three overlapping cDNA fragments produced by RT-PCRs (FIG. 1B). The Chlamydomonas DYRKP-1 consists of 14 exons and 13 introns, the coding region containing 3834 nucleotides. With regard to the gene model Cre07. g337300 (Phytozomev 9.0), the start codon is located 51 nucleotides upstream. The std1 mutant was complemented using a construct holding the wild-type DYRKP-1 genomic sequence driven by the psaD promoter (FIG. 2B). Two independent complemented strains std1:: STD1 1 and std1::STD1 2 were isolated, showing STD1 gene expression levels and Std1 protein amounts slightly lower to the wild-type progenitor (FIGS. 1C, 1D). Similar patterns of starch accumulation and degradation kinetics were observed in response to N or S deprivation in both complemented lines and in the wild-type progenitor (FIG. 2C). Northern blot analysis revealed that the DYRKP-1 transcript is strongly induced after 1 day of N depletion, the transcript levels remaining at a high level after 3-days of deprivation (FIG. 1E). Note that although DYRKP-1 gene expression was driven by the constitutive PSAD promoter in the complemented line, accumulation of the DYRKP-1 transcript increased in the same manner as in wild-type cells in response to N deprivation, suggesting that regulation of DYRKP-1 gene expression is regulated at a post-transcriptional level.

Chlamydomonas DYRKP-1/STD1 is a Member of a Novel Plant Specific Group of the DYRK Protein Family A phylogenetic analysis of the DYRK gene family allowed to distinguish four distinct branches: the previously described DYRK1, DYRK2 and Yak sub-families, and a novel DYRK group, named here DYRKP (for Plant DYRK) that solely comprises members of the green lineage (plants, mosses and algae), including the Chlamydomonas DYRKP-1/STD1 (FIG. 3A). While algal genomes harbor only one member of the DYRKP group, mosses and higher plants hold two to six plant-like homologues. Interestingly, plant and algal genomes contain Yak homologues, but no DYRK1 homologue (Han et al., 2012), DYRK2 homologues being only identified in algae and mosses, but not in higher plants. DYRK kinases exhibit conserved sequence features, particularly the DYRK homology (DH)-box that precedes the conserved catalytic domain (FIG. 3B). The consensus sequence for DYRK1 and DYRK2 sub-groups is NxGYDD (D/E)(N/R)xDY, slightly different for the Yak group (FIG. 3B). The DH-box of the novel identified DYRKP group shows an altered motif: (N/H)(R/K)TGFEExK(D/E/N)(F/L).

Std1 Shows a Strong Increase in Reserve Accumulation and More Robust Photosynthetic Activity Under Nutrient Deprivation in Conditions of Photoautotrophy The effect of nitrogen depletion was then studied in different growth conditions (mixotrophic vs. photoautotrophic) known to differentially affect the intracellular energy status and accumulation of reserve compounds such as starch (Ral et al., 2006) or TAGs (Goodson et al., 2011). In mixotrophic conditions (in the presence of both acetate and light), no difference in starch accumulation was observed between the WT and the std1 mutant in response to N deprivation (FIG. 4A), but an increase in the oil content was observed in the mutant after 1 to 3 days of starvation (FIG. 4B). In fully photoautotrophic conditions, a much higher and persistent starch accumulation was observed in std1 in comparison to the WT and to both complemented lines (FIG. 4B), the oil content increasing in the mutant after 3 days of starvation (FIG. 4B). When N deprivation was conducted in photoautotrophic conditions at a lower fluence rate (35 μmol photons $m^{-2}$ $s^{-1}$), WT and complemented mutant lines accumulated only low starch levels, whereas the std1 mutant accumulated high starch amounts (FIGS. 5A-D). Higher starch accumulation was also observed in std1 in response to sulfur deprivation (FIG. 5B). Photosynthetic electron transport rate (ETR), determined from chlorophyll fluorescence measurements, showed a parallel decline in std1 and control strains when N deprivation was realized in mixotrophic conditions (FIG. 4C, left panel). In contrast, when N deprivation was conducted under photoautotrophic conditions, the drop in ETR was less pronounced in std1 as compared to control strains (FIG. 4C, right panel). Taken together, these data show that, depending on the intracellular energy status, std1 accumulates more reserve compounds and maintains higher photosynthetic activity than control strains in response to nutrient deprivation. Immunodetection of major photosynthetic components showed a similar decrease of PSII, PSI, cytochrome $b_6f$, ATPase, and Rubisco subunits in std1 compared to the wild-type progenitor (FIG. 4D). Interestingly, the mitochondrial alternative oxidase (AOX) was much more abundant in the mutant than in the WT (FIG. 4D), indicating a redox imbalance in the mutant.

Increased Biomass Production in Std1 Mutant During Autotrophic Nitrogen Deprivation A strong increase in biomass production was observed in std1 from the size of cell pellets harvested after 3 and 10 days of culture in a N-deprived medium (FIG. 6A). Noticeably, while wild-type and complemented lines were counted as single cell particles of about 6-7 μm diameter, the std1 mutant consisted of aggregates of 2, 4 and 8 cells enclosed by the mother cell wall, and measured as particles of 10-20 μm diameter (FIG. 7). This phenotypical characteristic, previously described in several C. reinhardtii mutants, is called palmelloids (Harris, 2009). Despite cell aggregation, the total cellular volume was similar in wild-type and mutant cultures under N-replete conditions (FIG. 6B). In response to nitrogen deprivation, the total cellular volume showed only slight variations in wild-type and complemented cultures, but strongly increased in std1 (FIG. 6B). When nitrogen deprivation was conducted in mixotrophic condition (TAP-N), the std1 mutant showed a similar behavior as wild-type cells (FIG. 8). Biomass, measured as dry weight, showed a 1.7-fold increase in wild-type and complemented strains after 6 days of N depletion, and a more than 3-fold increase in std1 (FIG. 6C). In order to confirm the spectacular increase in biomass and starch production observed in std1, additional experiments were carried out in more controlled conditions using 1 L photobioreactors operated as turbidostats (FIG. 9). In these experiments, the cellular biomass was maintained at a constant level (monitored by $OD_{880\ nm}$) by addition of fresh culture medium, thus allowing dilution rate and biomass productivity measurements. At $t_0$, dilution by minimal N-replete medium was replaced by minimal N-free medium, resulting in a decrease in the ammonia content of the culture medium, which was fully exhausted after 45 h (FIG. 9A). At that time, the biomass productivity of the WT started to gradually decrease and completely stopped after 72 h. In sharp contrast, biomass productivity of std1 increased (from 45 h to 65 h) and then started to gradually decrease, the biomass productivity at 72 h being still higher than the initial productivity of the WT. These experiments demonstrate that std1 produces more starch and biomass than the control strain when submitted to N-deprivation under photoautotrophic conditions.

Discussion

We report here on the characterization of the std1 mutant affected in a DYRK kinase homologue belonging to a novel subgroup (called DYRKP), specific to the green lineage. The std1 mutant, the first DYRK mutant of the green lineage reported so far, accumulates high intracellular starch and oil amounts and shows a persistent photosynthetic activity in response to nutrient starvation.

Control of Biomass and Reserve Accumulation by DYRK Kinases

As shown in the experiments performed in different trophic conditions (mixotrophic vs. photoautotrophic), the cellular energy status, in addition to the nutrient status, plays a central role in the control of starch and oil accumulation in the mutant. In mixotrophic conditions (illuminated cells growing in an acetate-containing medium), conditions in which the energy status is high, high starch levels accumulate in the WT in response to N-deprivation, but no starch increase is observed in std1. Note that in these conditions an increase in the oil content was observed in the mutant. In photoautotrophic conditions however, starch accumulation in the WT depends on the intensity of illumination (low at low light intensity and higher at higher light). Strikingly, the dependence of starch accumulation upon the energy status is lost in std1, mutant cells accumulating similar starch amounts, while at different rates, in the different trophic conditions (FIG. 4A and FIG. 5A). In yeast, the DYRK homologue Yak1 has been reported to control glycogen storage, deletion of the YAK1 gene inducing an increase in the intracellular glycogen content (Wilson et al., 2010). Yak1 would control the arrest of the cell cycle in response to glucose deprivation by phosphorylating the transcription factors Msn2 and Hsf1 (Moriya et al., 2001). More recently, Yak1 was proposed to lie at the centre of a regulatory cascade controlling growth and stress response by targeting different transcription factors (Malcher et al., 2011). As for the yeast Yak1 mutant, the increased reserve and biomass production of std1 in response to nutrient deprivation indicates that a signal required to stop growth and reserve accumulation is not correctly perceived or transferred. In yeast, Yak1 is among others transcription factors such as Sfp1 and Msn2/4, at the intersection between PKA and TOR pathways (Rohde et al., 2008). To which extent *Chlamydomonas* and higher plants DYRKP are involved in TOR and cAMP-PKA signalling cascades will need further investigation to be elucidated.

Loss of Feedback Regulation of Photosynthesis in Std1

In microalgae, the decline in photosynthetic activity is part of the general cellular response to nutrient deprivation which helps to maintain a balance between the generation of reducing power by photosynthesis and the ability to use it for metabolic purposes (Grossman, 2000). The sac1 mutant (defect in Sacclimation response) was reported to die upon two days of S deprivation in the light due to an inability to down-regulate photosynthesis, resulting in an over-production of reactive oxygen species (ROS) damaging PSII centers (Davies et al., 1996; Wykoff et al., 1998). In contrast, the std1 mutant shows a decrease in photosynthetic complexes similar to that observed in control strains (FIG. 4D), but its photosynthetic activity, while decreasing, remains higher than in the control strain in photoautotropic conditions (FIG. 4C and FIG. 5B). In parallel, the std1 mutant accumulates more reserve compounds than control strains. The inventors therefore propose that the pronounced starch accumulation occurring in std1 functions as a sink for reducing power generated by photosynthesis, therefore decreasing the feedback inhibition of photosynthesis. Metabolite profiling studies have shown the existence in higher plants of a negative correlation between starch biomass production (Sulpice et al., 2009). Such a negative correlation is abolished in the std1 mutant in conditions of nutrient limitation where parallel starch and biomass productions are observed, at least in conditions of nutrient shortage.

Biotechnological Implications

The discovery of a negative regulator controlling growth and reserve accumulation in conditions of nutrient deprivation has important biotechnological implications for microalgae. Indeed, these unicellular microorganisms are increasingly considered as a promising biomass feedstock for the production of next generation biofuels. One of the major advantages of microalgae, when compared to higher plants, is their ability to accumulate high starch or lipid amounts, these compounds being convertible into bioethanol or biodiesel, respectively. However, techno-economic analyses have shown that productivity of reserve compounds need to be increased in order to reach economic feasibility.

Example 2: Additional Information on Characterization of the Std1 Mutant

Example 1 describes a massive accumulation of oil and starch after prolonged nitrogen starvation in the mutant std1. To dissect the molecular mechanism(s) between the mutated gene DYRK and the observed phenotype in carbon reserve formation, comparative transcriptomic, quantitative proteomic as well as lipidomic analyses of the mutant std1 were carried out and compared to its wild-type background strain 137AH.

Results

The Mutant Std1 Over-Accumulated Oxidized MGDG

In example 1, the inventors observed the over-accumulation of triacylglycerols (TAGs, oils) in the mutant std1 after prolonged nitrogen starvation (FIG. 4B). To gain a full picture of overall lipidomic changes in the mutant, they quantified lipid classes based on thin layer chromatograph (TLC), and compared changes in lipid molecular species using the state-of-the-art LC-MS/MS. First, each lipid class was quantified based on TLC. As shown in FIG. 10A, besides the classical polar lipids (i.e., MGDG, DGDG, DGTS, PG, PE) present in all strains, a new band was detected just below the MGDG only in the mutant std1 on the TLC plate (pointed by an arrow). The lipids present in the band were recovered via eluting with a mixture of chloroform and methanol (2:1) and subjected to identification by LC-MS/MS. Mass spectrometry analyses revealed the presence of a mixture of oxidized MGDG 34 with a combination of C16 and C18 fatty acids with different level of unsaturations. The mass spectrometry identification for one of the molecular species oxidized MGDG34:x is shown in FIG. 10B.

The relative quantity of these oxidized MGDG in the mutant cells was then further examined as compared to WT, also in a time dependent manner in response to nitrogen starvation. Mid-log phase grown cells were harvested once a day for 5 days, and total cellular lipids were extracted by the method of hexane and hot isopropanol. The total lipid extract was then subjected to lipidomic analyses by the state-of-the-art qTOF UPLC-MS/MS. Samples were subjected to both positive and negative analyses, for polar membrane lipid and for neutral lipid detection, respectively. As shown in FIG. 11, except DGTS, no significant differences were observed for all other cellular lipids between WT, the mutant std1 and two complemented strains (named here C2, and C7 respectively). Significant TAG accumulation after prolonged nitrogen starvation was observed, which confirms the previous TLC based analyses. For yet non-understood reasons, DGTS level remains constant in the mutant std1, yet increased dramatically in the WT in response to nitrogen starvation.

A basal level of oxidized MGDGs is present in cells of *Chlamydonomas reinhardtii*, which remained unaltered in response to nitrogen starvation in WT (FIG. 12A). Under nutrient sufficient conditions, the std1 mutant already accumulated over twice more oxidized MGDG than the wild-type cells, which significantly increased even further (up to 18 fold higher) in a time dependent manner in response to nitrogen starvation. The major oxidized MGDG species include the C16 and C18 species and the detailed structure for these oxylins are under investigation in the laboratory at the moment (FIG. 12B).

Collectively, the higher accumulation/synthesis of hydroperoxide MGDG points to potential dys-regulation of the gene(s) encoding proteins catalyzing or regulating lipid oxidation reactions. Lipid oxidation is a common metabolic reaction in all biological systems. This reaction is mainly catalyzed by proteins called lipoxygenases (LOX: EC:1.13.11.12). Lipoxygenases are a family of non-heme iron containing dioxygenases. LOXs catalyze the insertion of molecular oxygen into stereospecific position of a polyunsaturated fatty acid chain. LOXs are ubiquitously found in plants, mammals, coral, moss, fungi and also a number of bacteria and microalgae.

CreLOX1 is Upregulated at Both Transcriptomic as Well as at the Proteomic Level in the Std1 Mutant To gain better understanding of the potential regulatory networks involving STD1 protein, a comparative transcriptomic study based on the Illumina RNA-seq sequencing technology (Genoscope) was performed. Preliminary analyses of the transcriptomic dataset revealed an over 6 log fold (Log FC) increase of the CreLOX1 transcript as compared to WT cells under photoautotrophic conditions (Table 2). Quantitative proteomic analyses based on $^{15}N/^{14}N$ labelling showed striking increase in the CreLOX1 protein (up_to 30 log FC) in the mutant than in the WT (Table 2). This large increase in CreLOX1 protein amount in the mutant cells is further supported by the observation of an increased signal (~110 kDa) on the SDS-PAGE. This band was recovered and identified as indeed containing mainly the CreLOX1 protein (FIG. 13 and Table 3).

Products derived from these fatty acid oxidation reactions are collectively called oxylipins, which are lipophilic signaling molecules in many biological processes. Based on protein homology searches with the known *Arabidopsis* lipoxygenases as baits, only one putative homolog (CreLOX1) is encoded in the genome of *Chlamydomonas reinhardtii* (version 5). The locus encoding the putative CreLOX1 is Cre12.g512300 (phytozome version 5). The CreLOX1 protein has a theoretical molecular weight of 118 kDa, and contains two lipoxygenase domains similar to all its higher plant homologs. CreLOX1 is predicted to harbor a 65 amino acid long chloroplast transit peptide (cTP) at its N-terminus using the online ChloroP software. This is in agreement with the notion that the closet *Arabidopsis* homolog is the plastid localized AtLOX5.

TABLE 2

CreLOX1 is unregulated in the *Chlamydomonas* mutant std1 at both transcript and protein level.

| System biology approach | method | growth condition | Comparison | gene id | Annotation | LogFC | adj. p-value |
|---|---|---|---|---|---|---|---|
| Transcriptomics | RNA-Seq sequencing platform Illumina | MM 2% $CO_2$ | std1 vs. WT | Cre12.g512300.t1.1 Cre07.g337300.t1.2 | lipoxygenase 1 DYRKP-1 | 6.7 −1.93 | 0.000 0.000 |

TABLE 2-continued

CreLOX1 is unregulated in the Chlamydomonas mutant std1 at both transcript and protein level.

| System biology approach | method | growth condition | Comparison | gene id | Annotation | LogFC | adj. p-value |
|---|---|---|---|---|---|---|---|
| Quantitative proteomics | (14)N/(15)N-labeling Mass spectrometry | 24 h MM-N 2% $CO_2$ | std1 vs. WT | Cre12.g512300.t1.1 Cre07.g337300.t1.2 | lipoxygenase 1 DYRKP-1 | 29.6 n.d. | 0.063 |

Two large-scale studies were performed, a transcriptomic and a proteomic approach, that reveal an upregulation of lipoxygenase 1 in std1 mutant cells. The transcriptome dataset was obtained by RNA Sequencing using Illumina technology (Genoscope). Wild-type and std1 mutant cells were grown at standard autotrophic condition in minimum medium and 2% $CO_2$ in the air at 100 µE $m^{-2}$ $s^{-1}$ in triplicate precultures that were combined before harvesting. For quantitative proteomic analysis wild-type and mutant cells were grown at autotrophic conditions in 4 replicates for each strain, 2 replicates in minimum medium containing $^{14}N$ and 2 replicates containing $^{15}N$ ammonium salts leading to an overall metabolic labeling. Cells were centrifuged, washed, resuspended in MM-N medium and harvested after 24 h of nitrogen deprivation. Before protein extraction, cells from $^{14}N$-labeled wild-type were combined with cells from $^{15}N$-labeled std1 and vice versa giving 4 biological replicates. Log 2 fold change (log FC) for protein results is the mean of 4 replicates and given relative to wild-type. "Adj. p-value" is the p-value adjusted for Multiple Comparisons.

TABLE 3

Identification of proteins in the highlighted band in FIG. 13A by mass spectrometry.

| | | | WT | | | | | |
|---|---|---|---|---|---|---|---|---|
| accession | Annotation | mass (kDa) | rk | score | coverage | #peptides | emPAI | spectral counts |
| Cre06.g269050.t1.1 | NmrA-like family, Predicted dehydrogenase | 91.26 | 1 | 4671.86 | 67.26 | 54 | 15.31 | 95 |
| Cre12.g512300.t1.1 | LIPOXYGENASE | 117.92 | 2 | 4172.78 | 62.19 | 53 | 8.18 | 123 |
| Cre11.g477950.t1.2 | unknown function | 94.80 | 3 | 4440.31 | 77.86 | 39 | 6.21 | 66 |
| Cre06.g288700.t1.1 | Glycolate dehydrogenase | 120.45 | 4 | 3137.98 | 50.18 | 41 | 3.87 | 64 |
| Cre01.g054500.t1.1 | NADP TRANSHYDROGENASE | 112.85 | 5 | 2873.82 | 41.22 | 37 | 4.27 | 64 |

| | | | std1 | | | | | |
|---|---|---|---|---|---|---|---|---|
| accession | Define (aug10.2; 169) | mass (kDa) | rk | score | coverage | #peptides | emPAI | spectral counts |
| Cre12.g512300.t1.1 | LIPOXYGENASE | 117.92 | 1 | 3659.18 | 49.04 | 48 | 7.72 | 248 |
| Cre06.g269050.t1.1 | NmrA-like family, Predicted dehydrogenase | 91.26 | 2 | 3740.72 | 56.12 | 43 | 7.61 | 67 |
| Cre11.g477950.t1.2 | unknown function | 94.80 | 3 | 3733.94 | 62.53 | 34 | 3.44 | 50 |
| Cre01.g054500.t1.1 | NADP TRANSHYDROGENASE | 112.85 | 4 | 2429.72 | 43.65 | 31 | 2.13 | 37 |
| Cre06.g288700.t1.1 | Glycolate dehydrogenase | 120.45 | 5 | 2112.46 | 34.45 | 25 | 1.55 | 37 |

| | | | C2 | | | | | |
|---|---|---|---|---|---|---|---|---|
| accession | Define (aug10.2; 169) | mass (kDa) | rk | score | coverage | #peptides | emPAI | spectral counts |
| Cre06.g269050.t1.1 | NmrA-like family, Predicted dehydrogenase | 91.26 | 1 | 4919.95 | 64.92 | 56 | 17.04 | 108 |
| Cre11.g477950.t1.2 | unknown function | 94.80 | 2 | 4349.85 | 72.75 | 38 | 7.76 | 77 |
| Cre01.g054500.t1.1 | NADP TRANSHYDROGENASE | 112.85 | 3 | 2898.18 | 42.87 | 36 | 4.88 | 86 |
| Cre06.g288700.t1.1 | Glycolate dehydrogenase | 120.45 | 4 | 2823.34 | 45.52 | 38 | 2.59 | 50 |
| Cre12.g512300.t1.1 | LIPOXYGENASE | 117.92 | 5 | 2743.81 | 47.76 | 38 | 3.31 | 57 |

| | | | C7 | | | | | |
|---|---|---|---|---|---|---|---|---|
| accession | Define (aug10.2; 169) | mass (kDa) | rk | score | coverage | #peptides | emPAI | spectral counts |
| Cre06.g269050.t1.1 | NmrA-like family, Predicted dehydrogenase | 91.26 | 1 | 4052.68 | 59.24 | 46 | 9.18 | 73 |
| Cre11.g477950.t1.2 | unknown function | 94.80 | 2 | 3862.11 | 69.64 | 36 | 4.39 | 58 |
| Cre01.g005050.t1.1 | SELECTIN LIGAND RELATED, golgi apparatus protein 1 | 99.56 | 3 | 3007.98 | 45.86 | 43 | 3.98 | 53 |
| Cre12.g512300.t1.1 | LIPOXYGENASE | 117.92 | 4 | 2399.25 | 40.09 | 33 | 2.07 | 44 |
| Cre12.g517900.t1.1 | Chloroplast-associated SecA protein | 114.00 | 5 | 2029.16 | 32.72 | 29 | 1.25 | 30 |

The first 5 identified proteins are listed according to their rank (rk) for each strain. The score and coverage of the proteins and the number of identified peptides, which also correspond to specific peptides, are displayed. The values "emPAI" indicating the "exponentially modified Protein Abundance Index" and the number of total (specific) spectra observed ("spectral counts"; relevant and duplicated) may serve to give an estimation of the relative abundance of a protein in one sample.

LOX Inhibitors Prohibited Carbon Reserve (Lipid and Starch) Formation

Based on current results, the inventors hypothesized that the kinase STD1 act as a negative regulator of LOX1 protein. Indeed, products of lipoxygenase, oxylipins, are precursors to a large array of signaling molecules playing roles in many developmental as well as stress response signaling networks. To test this hypothesis, catechol (Sigma Cat#452637) was used. Catechol is a known lipoxygenase inhibitors, which inhibits the activity of lipoxygenase by quenching the cellular reactive oxygen species. Two different catechol concentrations (5 mM and 10 mM) were initially tested. With the presence of 5 mM catechol, both TAG and starch accumulation were inhibited in the std1 mutant after 6-day under nitrogen starvation (FIG. 14). Catechol also inhibited TAG accumulation in response to nitrogen starvation in WT strains, however no effect on starch accumulation was observed. Other conditions are tested.

From the above, it appears that inactivation of STD1 in std1 mutant provokes a LOX1 up-regulation, thus leading to the formation of a family of oxylipins that are involved in starch and TAG accumulations, inhibition of LOX activity by catechol preventing starch and TAG accumulation.

REFERENCES

Ball, S. G., Dirick, L., Decq, A., Martiat, J. C., Matagne, R. F., 1990. Physiology of starch storage in the monocellular alga *Chlamydomonas reinhardtii*. Plant Sci. 66, 1-9.

Becker, W., Joost, H. G., 1999. Structural and functional characteristics of Dyrk, a novel subfamily of protein kinases with dual specificity. Prog. Nucl. Acid. Res. Mol. Biol. 62, 1-17.

Berthold, P., Schmitt, R., Mages, W., 2002. An engineered *Streptomyces hygroscopicus* aph 7" gene mediates dominant resistance against hygromycin B in *Chlamydomonas reinhardtii*. Protist. 153, 401-412.

Chochois, V., Constans, L., Dauvillée, D., Beyly, A., Solivérès, M., Ball, S., Peltier, G., Cournac, L., 2010. Relationships between PSII-independent hydrogen bioproduction and starch metabolism as evidenced from isolation of starch catabolism mutants in the green alga *Chlamydomonas reinhardtii*. Int. J. Hydrogen Energ. 35, 10731-10740.

Dauvillee, D., Stampacchia, O., Girard-Bascou, J., Rochaix, J. D., 2003. Tab2 is a novel conserved RNA binding protein required for translation of the chloroplast psaB mRNA. EMBO J. 22, 6378-6388.

Davies, J. P., Yildiz, F. H., Grossman, A., 1996. Sac1, a putative regulator that is critical for survival of *Chlamydomonas reinhardtii* during sulfur deprivation. EMBO J. 15, 2150-2159.

Delrue, F., Li-Beisson, Y., Setier, P. A., Sahut, C., Roubaud, A., Froment, A. K., Peltier, G., 2013. Comparison of various microalgae liquid biofuel production pathways based on energetic, economic and environmental criteria. Bioresource Technol. 136, 205-212.

Goodson, C., Roth, R., Wang, Z. T., Goodenough, U., 2011. Structural correlates of cytoplasmic and chloroplast lipid body synthesis in *Chlamydomonas reinhardtii* and stimulation of lipid body production with acetate boost. Eukaryot. Cell. 10, 1592-1606.

Gouy, M., Guindon, S., Gascuel, O., 2010. SeaView version 4: A multiplatform graphical user interface for sequence alignment and phylogenetic tree building. Mol. Biol. Evol. 27, 221-224.

Grossman, A., 2000. Acclimation of *Chlamydomonas reinhardtii* to its nutrient environment. Protist. 151, 201-224.

Han, J. F., Miranda-Saavedra, D., Luebbering, N., Singh, A., Sibbet, G., Ferguson, M. A. J., Cleghon, V., 2012. Deep evolutionary conservation of an intramolecular protein kinase activation mechanism. Plos One. 7.

Harris, E. H., 2009. The *Chlamydomonas* sourcebook. Second edition. Academic Press.

Hu, Q., Sommerfeld, M., Jarvis, E., Ghirardi, M., Posewitz, M., Seibert, M., Darzins, A., 2008. Microalgal triacylglycerols as feedstocks for biofuel production: perspectives and advances. Plant J. 54, 621-639.

Katoh, K., Misawa, K., Kuma, K., Miyata, T., 2002. MAFFT: a novel method for rapid multiple sequence alignment based on fast Fourier transform. Nucleic Acids Res. 30, 3059-3066.

Kindle, K. L., 1990. High-frequency nuclear transformation of *Chlamydomonas reinhardtii*. Proc. Natl. Acad. Sci. USA. 87, 1228-1232.

Larkum, A. W. D., Ross, I. L., Kruse, O., Hankamer, B., 2012. Selection, breeding and engineering of microalgae for bioenergy and biofuel production. TiBiotech. 30, 198-205.

Li-Beisson, Y., Shorrosh, B., Beisson, F., Andersson, M. X., Arondel, V., Bates, P. D., Baud, S., Bird, D., Debono, A., Durrett, T. P., Franke, R. B., Graham, I. A., Katayama, K., Kelly, A. A., Larson, T., Markham, J. E., Miguel, M., Molina, I., Nishida, I., Rowland, O., Samuels, L., Schmid, K. M., Wada, H., Welti, R., Xu, C., Zallot, R., Ohlrogge, J., 2010. Acyl-lipid metabolism. *Arabidopsis* Book. 8:e0133. doi: 10.1199/tab.0133. Epub 2010 Jun. 11.

Liu, C. M., Willmund, F., Whitelegge, J. P., Hawat, S., Knapp, B., Lodha, M., Schroda, M., 2005. J-domain protein CDJ2 and HSP70B are a plastidic chaperone pair that interacts with vesicle-inducing protein in plastids 1. Mol. Biol. Cell. 16, 1165-1177.

Matcher, M., Schladebeck, S., Mosch, H. U., 2011. The Yak1 protein kinase lies at the center of a regulatory cascade affecting adhesive growth and stress resistance in *Saccharomyces cerevisiae*. Genetics. 187, 717-730.

Merchant, S. S., Kropat, J., Liu, B. S., Shaw, J., Warakanont, J., 2012. TAG, You're it! *Chlamydomonas* as a reference organism for understanding algal triacylglycerol accumulation. Curr. Op. Biotechnol. 23, 352-363.

Moriya, H., Shimizu-Yoshida, Y., Omori, A., Iwashita, S., Katoh, M., Sakai, A., 2001. Yak1p, a DYRK family kinase, translocates to the nucleus and phosphorylates yeast Pop2p in response to a glucose signal. Genes & Dev. 15, 1217-1228.

Peltier, G., Schmidt, G. W., 1991. Chlororespiration—an adaptation to nitrogen deficiency in *Chlamydomonas reinhardtii*. Proc. Natl. Acad. Sci. USA. 88, 4791-4795.

Ral, J. P., Colleoni, C., Wattebled, F., Dauvillee, D., Nempont, C., Deschamps, P., Li, Z. Y., Morell, M. K., Chibbar, R., Purton, S., d'Hulst, C., Ball, S. G., 2006. Circadian clock regulation of starch metabolism establishes GBSSI as a major contributor to amylopectin synthesis in *Chlamydomonas reinhardtii*. Plant Physiol. 142, 305-317.

Rohde, J. R., Bastidas, R., Puria, R., Cardenas, M. E., 2008. Nutritional control via Tor signaling in *Saccharomyces cerevisiae*. Curr. Opin. Microbiol. 11, 153-160.

Rumeau, D., Becuwe-Linka, N., Beyly, A., Louwagie, M., Garin, J., Peltier, G., 2005. New subunits NDH-M, -N, and -O, encoded by nuclear genes, are essential for plastid Ndh complex functioning in higher plants. Plant Cell. 17, 219-232.

Schroda, M., Vallon, O., Wollman, F. A., Beck, C. F., 1999. A chloroplast-targeted heat shock protein 70 (HSP70) contributes to the photoprotection and repair of photosystem II during and after photoinhibition. Plant Cell. 11, 1165-1178.

Schulz-Raffelt, M., Lodha, M., Schroda, M., 2007. Heat shock factor 1 is a key regulator of the stress response in *Chlamydomonas*. Plant J. 52, 286-295.

Siaut, M., Cuine, S., Cagnon, C., Fessler, B., Nguyen, M., Carrier, P., Beyly, A., Beisson, F., Triantaphylides, C., Li-Beisson, Y. H., Peltier, G., 2011. Oil accumulation in the model green alga *Chlamydomonas reinhardtii*: characterization, variability between common laboratory strains and relationship with starch reserves. BMC Biotechnol. 11.

Sulpice, R., Pyl, E. T., Ishihara, H., Trenkamp, S., Steinfath, M., Witucka-Wall, H., Gibon, Y., Usadel, B., Poree, F., Piques, M. C., Von Korff, M., Steinhauser, M. C., Keurentjes, J. J. B., Guenther, M., Hoehne, M., Selbig, J., Fernie, A. R., Altmann, T., Stitt, M., 2009. Starch as a major integrator in the regulation of plant growth. Proc. Natl. Acad. Sci. USA. 106, 10348-10353.

Tamura, K., Peterson, D., Peterson, N., Stecher, G., Nei, M., Kumar, S., 2011. MEGA5: Molecular evolutionary genetics analysis using maximum likelihood, evolutionary distance, and maximum parsimony methods. Mol. Biol. Evol. 28, 2731-2739.

Tolleter, D., Ghysels, B., Alric, J., Petroutsos, D., Tolstygina, I., Krawietz, D., Happe, T., Auroy, P., Adriano, J. M., Beyly, A., Cuine, S., Plet, J., Reiter, I. M., Genty, B., Cournac, L., Hippler, M., Peltier, G., 2011. Control of hydrogen photoproduction by the proton gradient generated by cyclic electron flow in *Chlamydomonas reinhardtii*. Plant Cell. 23, 2619-2630.

Wijffels, R. H., Barbosa, M. J., 2010. An outlook on microalgal biofuels. Science. 329, 796-799.

Wilson, W. A., Roach, P. J., Montero, M., Baroja-Fernandez, E., Munoz, F. J., Eydallin, G., Viale, A. M., Pozueta-Romero, J., 2010. Regulation of glycogen metabolism in yeast and bacteria. FEMS Microbiol. Rev. 34, 952-985.

Wykoff, D. D., Davies, J. P., Melis, A., Grossman, A. R., 1998. The regulation of photosynthetic electron transport during nutrient deprivation in *Chlamydomonas reinhardtii*. Plant Physiol. 117, 129-139.

---

The invention claimed is:

1. A method for producing biomass feedstock, comprising the steps of:
   (i) cultivating green microalgae cells in which the expression and/or the activity of the dual-specificity tyrosine-phosphorylation-regulated kinase (DYRKP-1) protein is impaired in comparison to wild-type green microalgae cells,
   wherein the amino acid sequence of said DYRKP-1 protein is SEQ ID NO: 1, or a sequence having at least 90% sequence identity to SEQ ID NO: 1 and comprising the DH box sequence of SEQ ID NO: 3, and wherein said impairment is obtained by silencing, knocking down, mutating and/or interrupting the DYRKP-1 gene or by inhibiting the activity of the DYRKP-1 protein by a chemical compound acting as a specific inhibitor; and
   (ii) inducing an accumulation of a reserve compound and/or an increase in biomass production by said microalgae, in comparison to wild-type green microalgae cells, by incubating the microalgae cells in a deficient medium, wherein said deficient medium is deficient in at least one element, the concentration of said element being at least 10-fold below the concentration of said element in a classical medium used for microalgae medium;
   wherein the biomass produced is oil or starch.

2. The method according to claim 1, wherein said microalgae lack a functional DYRKP-1 gene, wherein the coding sequence of said DYRKP-1 gene is SEQ ID NO: 2, or a sequence having at least 80% sequence identity to SEQ ID NO: 2.

3. The method according to claim 1, wherein said microalgae are *Chlamydomonas*.

4. The method according to claim 1, wherein said microalgae are *Chlamydomonas reinhardtii*.

5. The method according to claim 1, wherein the deficient medium comprises a medium deficient in at least one element selected from the group consisting of nitrogen, sulfur and phosphorus.

6. The method according to claim 1, wherein step (ii) comprises illuminating the microalgae cells.

7. The method according to claim 6, wherein said illumination is performed at an intensity comprised between 25 and 2000 µmol photons $m^{-2}$ $s^{-1}$, during 8 to 24 hours per day.

8. The method according to claim 5, wherein the step of incubating the microalgae cells in the deficient medium lasts at least 24 hours.

9. The method according to claim 8, wherein the step of incubating the microalgae cells in the deficient medium lasts from 2 to 8 days, preferably from 3 to 6 days.

10. The method according to claim 1, wherein in step (ii), the cells are incubated during 2 to 6 days in a deficient medium comprising acetate as the organic carbon.

11. The method of claim 1, wherein in step (ii), the cells are incubated during at least 15 hours in photoautotrophic conditions in a deficient medium.

* * * * *

SEQUENCE LISTING

```
<160> NUMBER OF SEQ ID NOS: 24

<210> SEQ ID NO 1
<211> LENGTH: 1278
<212> TYPE: PRT
<213> ORGANISM: Chlamydomonas reinhardtii

<400> SEQUENCE: 1

Met Ser Ala Thr Gly Gly Gln Ser Glu Gly His Val Ala Pro Pro Glu
1               5                   10                  15

Pro Met Ser Leu Asp Thr Leu Asn Phe Val Val Asn Phe Leu His Ser
            20                  25                  30

Ser Gly Phe His Lys Ala His Ser Ala Leu Leu Gln Glu Phe Ser Thr
        35                  40                  45

Arg Leu Asn Pro Thr Ala Glu Gly Ala Leu Phe Ala Ala Ala Arg Thr
    50                  55                  60

Ser Val Ser Ala Cys Ser Ala Pro Pro Ser Thr Ser Glu Tyr Val Glu
65                  70                  75                  80

Arg Ala Leu Glu Ala Leu Ser Pro Pro Arg Ser Lys Ser Ala Gln Ala
                85                  90                  95

Gly Pro Ser Trp Glu Gly Phe Pro Gly Pro Ala Ala Gln Pro Lys Ala
            100                 105                 110

Gln Ser Thr Ala Gly Ala Val Glu Ser Ala Pro Ala Pro Ala Pro Pro
        115                 120                 125

Pro Pro Ser Lys Pro Ala Thr Pro Val Ser Pro Pro Thr Thr Ala Pro
130                 135                 140

Val Thr Arg Ala Lys Arg Arg Gln Ser Arg Pro Ser Ala Thr Arg Gln
145                 150                 155                 160

Arg Pro Ala Trp Asp Gly Glu Val Asp Asp Tyr Asp Gly Met Asp Asp
                165                 170                 175

Pro Gly Tyr Ser Arg Lys Glu Val Pro Asn Pro Ser Arg Phe Ala Glu
            180                 185                 190
```

```
Ile Glu Leu Asp Ala Ala Ser Gly Asp Glu Gly Ser Glu Arg Gln Tyr
            195                 200                 205

Phe Met His Gln Pro Gly Asp Leu Asn Tyr Asp Asp Ile Glu Ser Glu
        210                 215                 220

Val Ser Ala Ser Asp Leu Glu Gly Ile Thr Ala Ala Ser Ser Val Gln
225                 230                 235                 240

Ser Gly Asn Tyr Thr Gly Gly Asp Thr His Asp Glu Thr Trp Asp Phe
                245                 250                 255

Gly Pro Ile Asp Ile Lys Phe Ala Glu Pro Val Ser Thr Pro Ser Lys
            260                 265                 270

Ser Pro Glu Lys Gln Glu Ala Glu Glu Arg Arg Pro Val Leu Ser Arg
        275                 280                 285

Val Glu Ser Leu Ser Ser Phe Lys Asp Phe Glu Met Glu Arg Gly
290                 295                 300

Phe Glu Ala Asp Gly Glu Gly Gly Gln Ile Ser Ser Lys Val Ser
305                 310                 315                 320

Glu Ala Glu Tyr Ala Ala Asp Pro Glu Val Ile Asp Phe Pro Val Pro
                325                 330                 335

Val Pro Ala Val Asn His Glu Asp Val Glu Leu Phe Arg Asn Gln Arg
            340                 345                 350

Arg Pro Ser Pro Thr Ser Ser Met Asp Val Ala Ala Gly Ser Leu Ala
        355                 360                 365

Pro Ser Val Ala Pro Ser Glu Gln Gln Pro Ser Glu Ser Thr Gly Ser
370                 375                 380

Gln Glu Arg Gln Arg Lys Gly Thr Gly Lys Ser Thr Ser Leu Leu Lys
385                 390                 395                 400

Ser Leu Ala Gly Arg Ser Ala Asp Ala Arg Asp Gly Ala Gly Leu Thr
                405                 410                 415

Leu Gly Ser Ser Ala Leu Ser Ser Gly Gly Ala Ser Ser Ser Ala Ala
            420                 425                 430

Arg Pro Ser Ala Pro Thr Val Gly Thr Gly Ala Ala Ser Gly Gly
        435                 440                 445

Gly Gly Phe Gly Gly Gly Gly Phe Gly Gly Gly Gly Phe Gly Gly Gly
450                 455                 460

Phe Ser Phe Pro Val Thr Pro Pro Thr Ala Asp Glu Pro Asp Gln Arg
465                 470                 475                 480

Leu Phe Thr Ser Trp Pro Ser Val Arg Ser Ser Cys Thr Ser Glu Pro
                485                 490                 495

Val Ala Met Ser Asp Asp Asn Ala Leu Pro Ala Glu Tyr Ala Asp
            500                 505                 510

Asp Glu Tyr Ser Lys Tyr Arg Leu Ser Ser Arg Ser Thr Ser Met Ala
        515                 520                 525

Ala Gln Asp Leu Pro Glu Gln Arg Lys Thr Ala Asp Gly Glu Thr Ser
530                 535                 540

Gly Thr Leu Ala Ser Pro Asp Gly Asn Ser Ala Ala Gly Ser Gly Thr
545                 550                 555                 560

Ala Arg Gln Ala Gly Ala Gly Ala Pro Ala Ala Asp Ala Ala Ala Asp
                565                 570                 575

Leu Asp Phe Ser Leu Glu Trp Glu Phe Arg Pro Pro Leu Ser His Glu
            580                 585                 590

Ser Arg Glu Pro Ser Leu Glu Phe Ser Thr Ala Asn Thr Asp Asp Glu
        595                 600                 605

Gly Leu Gly Thr Pro Lys Ala Val Ala Ala Ala Ala Ala Ala Ala Ala
```

-continued

```
            610                 615                 620
Ala Ala Ala Ala Ala Ala Ala Asn Glu Val Ser Ala Val Leu Thr
625                 630                 635                 640

Leu Glu Pro Thr Pro Ser Ala Ser Ala Gly Val Ala Ala Ala Ala
                    645                 650                 655

Pro Ala Pro Ala Ala Gly Ser Gly Pro Gly Gln Glu Pro Glu Val Glu
                660                 665                 670

Gly Gly Asp Val Leu Asp Thr His Asn Gly Ser Val Thr Leu Ala Gly
            675                 680                 685

Glu Val Glu Ala Ala Ala Ala Gln Leu Val Gln Leu Met Pro Gln Leu
        690                 695                 700

Ala Leu Ile Asp Asp Ala Asp Ala Gly Ser Lys Pro Gly Thr Pro Val
705                 710                 715                 720

Asp Ala Leu Glu Arg Lys Asp Ser Ser Gln Val Val Ala His Arg Ile
                    725                 730                 735

Asn Phe Glu Ser Glu Asp Leu His Asp Ala His Ser His Asp Gly Gly
                740                 745                 750

Ala Ser Val His Ser Ala Pro His Ile Gly Ala Ala Ala Glu Ala Val
            755                 760                 765

Pro Glu Pro Leu His Glu His Glu His Glu Arg Asp Asp Gln Ser Ser
        770                 775                 780

Ile Ser Ala Ala Ile Ala Ala Val Glu Val Ala Ala Glu Ala Asp Asp
785                 790                 795                 800

Glu Asp Thr Asp Leu Gly Glu Asp Gly Val Ala Ala Ala Ser Phe
                    805                 810                 815

Ser Glu Pro Ala Ser Tyr Asp Ala Asp Ala Asp Val Asp Glu Pro
                820                 825                 830

Glu Pro Leu Ser Gly Leu Ala Asp Asp Glu Glu Arg Leu Gly Gly Asp
            835                 840                 845

Glu Asp Asp Asp Glu Asp Asp Glu Asp Glu Asp Glu Asp Glu Glu
        850                 855                 860

Asp Glu Ala Gly Arg Arg Ser Ser Gly Gly Val Val Gly Val Gly Ala
865                 870                 875                 880

Gly Gly Glu Trp Gly Asp Glu Gln His Leu Arg Ala Pro Asp Ala Lys
                    885                 890                 895

Asp Ile Ala Arg Ala Arg Pro Glu Ser Ser Leu Thr Pro Arg Tyr His
                900                 905                 910

Met Asp Glu Gln Gly Asn Val Leu Tyr Glu Tyr Asp Pro Asp Tyr Ile
            915                 920                 925

Asp Arg Lys Tyr Glu Val Phe Glu Leu Arg Val Ile His Arg Arg His
        930                 935                 940

Arg Thr Gly Phe Glu Glu Thr Lys Asp Phe Pro Ile Arg Leu Asn Asp
945                 950                 955                 960

Leu Ile Ala Gly Arg Tyr Gln Val Met Asp Phe Leu Gly Ser Ala Ala
                    965                 970                 975

Phe Ser Arg Ala Val Gln Ala Leu Asp Ile Lys Thr Gly Gln Leu Val
                980                 985                 990

Cys Leu Lys Ile Ile Lys Asn His  Lys Asp Tyr Phe Asp  Gln Ser Leu
            995                 1000                1005

Asp Glu  Ile Lys Leu Leu Lys  Tyr Val Asn Thr Met  Asp Pro Asn
        1010                1015                1020

Asp Glu  Tyr Ala Ile Val Arg  Leu Tyr Asp Phe Phe  Tyr Tyr Lys
        1025                1030                1035
```

```
Glu His Leu Phe Leu Val Cys Glu Leu Leu Arg Ala Asn Leu Tyr
    1040                1045                1050

Glu Phe Gln Lys Tyr Asn Lys Glu Ser Gly Asp Pro Ala Tyr Phe
    1055                1060                1065

Thr Asn Ala Arg Ile Gln Arg Ile Ala Arg Gln Ala Leu Arg Ser
    1070                1075                1080

Leu Ala Phe Leu His Ser Leu Gly Leu Ile His Ser Asp Leu Lys
    1085                1090                1095

Pro Glu Asn Ile Leu Ile Lys Ser Tyr Ser Arg Cys Glu Val Lys
    1100                1105                1110

Val Ile Asp Leu Gly Ser Ser Cys Phe Ile Thr Asp Gln Leu Ser
    1115                1120                1125

Ser Tyr Val Gln Ser Arg Ser Tyr Arg Ala Pro Glu Val Ile Leu
    1130                1135                1140

Gly Leu Pro Tyr Asp Tyr Lys Val Asp Val Trp Ser Leu Gly Cys
    1145                1150                1155

Ile Leu Ala Glu Leu Ser Ser Ser Phe Val Leu Phe Gln Asn Asp
    1160                1165                1170

Ser Leu Ser Thr Leu Leu Ala Arg Leu Glu Gly Ile Leu Gly Pro
    1175                1180                1185

Val Pro Glu Trp Met Leu His Lys Gly Arg Tyr Ala His Arg Phe
    1190                1195                1200

Tyr Thr Arg Ser Gly Met Leu Tyr Glu Arg Asn Ala Thr Thr Gln
    1205                1210                1215

Lys Tyr Asp Met Leu Gln Pro Lys Arg Thr Ser Leu Arg His Arg
    1220                1225                1230

Met Pro Asp Ala Asp Glu Gly Leu Leu Glu Phe Val Gly His Leu
    1235                1240                1245

Leu Thr Val Asp Pro Arg Lys Arg Pro Thr Ala Ala Glu Ala Leu
    1250                1255                1260

Lys His Pro Trp Leu Gln Gln Glu Tyr Pro Ser Leu Asp Ser Met
    1265                1270                1275

<210> SEQ ID NO 2
<211> LENGTH: 5200
<212> TYPE: DNA
<213> ORGANISM: Artificial Sequence
<220> FEATURE:
<223> OTHER INFORMATION: DYRKP-1 cDNA sequence including 5' UTR and 3'
      UTR
<220> FEATURE:
<221> NAME/KEY: misc_feature
<222> LOCATION: (165)..(167)
<223> OTHER INFORMATION: Start codon : nt n, n+3
<220> FEATURE:
<221> NAME/KEY: misc_feature
<222> LOCATION: (3999)..(4001)
<223> OTHER INFORMATION: Stop codon : nt m, m+3

<400> SEQUENCE: 2
gtattcaata accacaggta ccttacttac cagacttgct atcacggtcc tcgttgacct      60
ctgaagtcgt cgagatggtt gtgcctgaac ctagttggcc aaggctcgtt tgagaggggc     120
ttgccatagt gctcagcagg ggacaaggcc cgcaagtggt caaaatgtca gcaacggggg     180
gccaaagtga gggccatgtc gctccgcctg aaccgatgtc gctggatacg cttaattttg     240
tcgtgaactt tctccattcg tccgggtttc acaaggcgca cagcgcactg ctccaggagt     300
tcagcacgcg gctgaacccc accgcggaag gagcgctctt cgcagctgcg cgaacttcgg     360
```

```
tcagcgcttg ttccgctcca ccttccacgt cggagtatgt ggagcgtgcg ctggaggctc      420
tatctcctcc tcgcagcaag tctgcgcagg cgggaccgag ctgggaagga tttccgggac      480
cggcagcgca gccaaaggcg cagtccacag ctggtgcagt tgaaagtgcg ccagctcccg      540
ccccgccacc gcccagcaag ccagctacgc ctgtcagccc tccgactacg gctcctgtaa      600
cacgtgctaa acgtcgacaa tccaggccct cggctacccg gcaacgacct gcctgggacg      660
gagaggtgga tgactacgat ggcatggacg acccgggcta tagccggaag gaggtgccga      720
acccgtcgcg cttcgcggag attgagctcg acgctgcaag cggcgacgag ggcagcgagc      780
ggcaatactt catgcaccag cccggcgacc tcaactatga tgatatcgag tcagaggtgt      840
ccgcctcgga cctggagggc atcaccgcag ccagcagcgt gcagtcgggg aactacacag      900
ggggtgacac gcacgacgaa acctgggact tcggccccat agatatcaag ttcgcggagc      960
cggtcagcac gcccagcaag agcccggaga agcaagaagc ggaggagcgg cggccggtgc     1020
tttcgcgcgt ggagtcgctc agcagctctt ttaaggactt cgagatggag cggggctttg     1080
aggcagacgg cgagggcggg ggccagatct catcaaaggt gtcggaggcg gagtacgcag     1140
cggacccgga ggtgattgac ttccctgtgc cggtgccggc ggtgaaccat gaggacgtgg     1200
agctgttccg caaccagcgg cggcccagcc ccacgtcctc catggacgtg ccgccggct      1260 cgctggcgcc gtccgtagca ccctcggagc agcagccttc cgaaagcacg ggcagtcagg     1320
agcggcagcg caagggcacg ggcaagagca cttcgctgct caagtcgctg gccgggcggt     1380
cagcggacgg tcgcgacggt gccggcctga cgctgggtag cagcgcgctc agcagcggtg     1440
gcgccagtag ctctgcggcg cgacccagcg cacccacggt aggcaccggc ggcgccgctt     1500
ccggtggtgg cgggttcggc ggtggcggct ttggcggcgg cggctttggc ggcggcttca     1560
gcttcccggt gacgccgccc acggcggatg agccagacca gcggctgttc acgtcgtggc     1620
cttccgtccg cagcagctgt acgtcagagc cggtggccat gtcggacgac gacaacgcgc     1680
tgccggccga gtacgcggac gacgagtact cgaagtaccg gctcagcagc cgcagcacgt     1740
ccatggcggc gcaggaccta ccggagcagc gcaaaaccgc ggacggcgaa acctctggca     1800
cgcttgccag ccccgatggc aactccgcgg ccgggtcagg cacggcgcgg caggccggcg     1860
ccggcgcgcc tgccgcagac gccgccgcag acctggattt ctcgctggag tgggagttcc     1920
ggccgccgct cagccacgag tcgcgggagc cgtcgctgga gttctccaca gccaacacgg     1980
acgacgaggg gctggggaca cccaaggcgg tcgcggcggc ggcagctgcc gccgccgccg     2040
ccgccgctgc ggcggccgcg aacgaggtca gcgcggtgct cacactggag ccgacaccgt     2100
cggcgtcagc gggtgtggcc gcggcggcgg cgccagcgcc ggccgctggg tccgggccgg     2160
ggcaggagcc ggaggtcgag ggcggcgacg tgctggacac gcacaacggc tcggtgacgc     2220
tgcggggcga ggtggaggcg gcgcggcgc agctggtgca gctgatgccg cagctggcgc     2280
tcatcgacga cgctgacgcc ggcagcaagc cgggcacgcc ggtggacgcg ctggagcgga     2340
aagactcctc ccaagtggtg gcgcaccgca tcaacttcga gtcggaggac ctgcacgacg     2400
cccactccca cgacggcggc gcctccgtgc actccgcgcc gcacatcggc gcggccgcgg     2460
aggccgtgcc cgaaccctgg cacgagcacg aacacgagcg cgacgaccag tccagcatca     2520
gcgccgccat cgcggcggtg gaggtcgccg cggaggcgga tgacgaggat acggacctgg     2580
gtgaggatgg cgttgcggca gcggcgtctt tttccgagcc ggcgtcgtac gatgccgatg     2640
acgccgacgt ggatgagccg gagccgctgt cggggctggc ggatgatgag gagcggctgg     2700
```

```
gcggcgacga ggatgatgat gaggacgatg aagatgacga ggacgaggac gaggaggacg    2760
aggccgggag acgcagcagc ggcggcgtgg tgggcgttgg cgccggcggc gagtggggcg    2820
acgagcagca cttgcgcgcg ccggacgcca aggacattgc ccgcgcgcgg cccgagtcca    2880
gcctgacgcc ccgctaccac atggacgagc agggcaacgt gctgtacgag tacgaccctg    2940
actacatcga ccgcaagtac gaggtgtttg agctgcgcgt catccaccgc cgccaccgca    3000
ccggcttcga ggagaccaag gacttcccca tccgcctcaa cgacctcata gcgggcaggt    3060
accaggtgat ggacttcctg ggctccgccg ccttcagccg cgcggtacag gcgctggaca    3120
tcaagacggg gcagctggtg tgcctcaaga tcatcaagaa ccacaaagac tactttgacc    3180
agtcgctgga cgagatcaag ctgctcaagt acgtcaacac catggacccc aacgacgagt    3240
acgccatcgt gcgcctgtac gacttcttct actacaagga gcacctgttc ctggtgtgcg    3300
agctgctgcg cgccaacctg tacgagttcc agaagtacaa caaggagtcg ggcgacccgg    3360
cctacttcac caacgcgcgc atccagcgca tcgcgcggca ggcgctgcgc tcgctggcgt    3420
tcctacactc gctggggctg atccactccg acctcaagcc cgagaacata tcatcaaga    3480 gctacagcag gtgtgaggtc aaggtgattg acctgggctc ctcctgcttc atcacggacc    3540
agctcagcag ctacgtgcag agccgctcct accgcgcgcc ggaggtcatc ctgggtctgc    3600
cctacgacta aaggtggac gtgtggtctc tgggctgcat cctggcggag ctgtccagca    3660
gctttgttct tttccagaac gactcgctgt ccacgctgct ggcgcggctg gagggcattc    3720
tgggccccgt gcccgagtgg atgctgcaca agggccgcta cgcgcaccgc ttctacacgc    3780
gcagcggcat gctgtacgag cgcaacgcca ccacccagaa gtacgacatg ctgcagccca    3840
agcgcacctc gctgcggcac aggatgccgg acgcggacga ggggctgctg gagttcgtgg    3900
gccacctgct gacggtggac ccgcgcaagc gccccaccgc cgccgaggcg ctcaagcacc    3960
cctggctgca gcaggagtac ccctcgctcg acagcatgta ggcgggcggc ggacagtggc    4020
ggccagtggc gcaagcgctg gcgctgggc cgcgctaagg ggtgctgcag cagcaggacc    4080
agcagagcgg aggccggcgg cagaggccgg gatggggccc gcggcagttt caggcagcaa    4140
gcggaaaccg gcaaggcttg acaacaactg ttttgtgggt gggtgggtaa tgcgggcttc    4200
cagagtggac ttcagcattt ggggttctgg ggtcgagggg ctacaggctg gctgctttgg    4260
agaggattgg gcggtcatag gggcacatac gtattgtttg gcagtcaca gcggctttc    4320 aggctcgggc gggagaagtt actgcatggc atagtacgca gaggaaggaa tagggggcgtg    4380 cattcggagc cgtgcggcag acagcgcggg ctgacgtcaa ccggcggctg tgtgctcgtg    4440
cgcggaaggc ggttctgctg ttgcgcacat gggtcattat cattcgacac gtatcaggcg    4500
acgtcggcac acaatcgagg ccgaggtatt ggcctcccca ccaagcaagg agtcaggaag    4560
ggcccaaaga gatctcacgc gagtgacgtg cgagtcctgt tgcctacctg gtgtgcaagt    4620
tatctacgcc gcatgggac tcccgcggct gtgccgcgtc tgcgcgcgca acattgcaac    4680
ataccggtgc gcacgtttgc acccggtttt tcagatgaag tttgggttca agtgcggggt    4740
agcggctcag cgggtcttcg catctacatg tcctggcgga agagtgcgtg tctggtgtcg    4800
agtcatcgcg ggggcatgcg cagaccgttt gccagggggc tggggccctg cgatgcgaag    4860
gcaacgaaca agtgtgcgtg ggctgggtgt gtgtgtgcat gtgtcagggt gtgcttgcgg    4920
gcgcgctcgt gaatctgtgt tgtgttggtg tatgcatgaa cgcggtggcg tggcagctca    4980
catggtaagt gctgtgtgga ggccctgggc agaatcagcg aagcggtgtg gtgtcattga    5040
aggtcaagct gtgcaaccca gtaacaggga cgaccccgca gggagagggg cgccatggta    5100
```

```
gctgggcagg actggggaag gtggcggcat atcactgaga gtatgtagcg cgtcgacagg    5160
gggcaacggc caacacgccg tcgtgtaaca cattacacgc                          5200
```

<210> SEQ ID NO 3
<211> LENGTH: 11
<212> TYPE: PRT
<213> ORGANISM: Artificial Sequence
<220> FEATURE:
<223> OTHER INFORMATION: DYRK protein
<220> FEATURE:
<221> NAME/KEY: VARIANT
<222> LOCATION: (2)..(2)
<223> OTHER INFORMATION: X = R or K
<220> FEATURE:
<221> NAME/KEY: VARIANT
<222> LOCATION: (8)..(8)
<223> OTHER INFORMATION: X = any
<220> FEATURE:
<221> NAME/KEY: VARIANT
<222> LOCATION: (10)..(10)
<223> OTHER INFORMATION: X = D, E or N
<220> FEATURE:
<221> NAME/KEY: VARIANT
<222> LOCATION: (11)..(11)
<223> OTHER INFORMATION: X = F or L

<400> SEQUENCE: 3

His Xaa Thr Gly Phe Glu Glu Xaa Lys Xaa Xaa
1               5                   10

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4

```
cgaagcatgg acgatgcgtt                                                  20
```

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5

```
cgagactgcg atcgaacgga ca                                               22
```

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6

```
ctggtgctgc gcgagctggc ccacgaggag                                       30
```

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7

```
tggttcgggc cggagtgttc cgcggcgtt                                         29

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gtctagaatg tcgctccgcc tgaaccgatg                                        30

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
gtctagacta catgctgtcg agcgagg                                           27

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
catagtgctc agcaggggac aaggc                                             25

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
agcgtgccag aggtttcgcc gtc                                               23

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
ccgcggacgg cgaaacctct ggcac                                             25

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gatctcgtcc agcgactggt caaagtag                                          28

<210> SEQ ID NO 14
<211> LENGTH: 29
<212> TYPE: DNA
```

```
<213> ORGANISM: Artificial Sequence
<220> FEATURE:
<223> OTHER INFORMATION: primer

<400> SEQUENCE: 14
gcggatccga cgagcagggc aacgtgctg                                  29

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
cggcaagctt ctacatgctg tcgagcgagg                                 30

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
aatcgtgcgc gacatcaagg agaa                                       24

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
ttggcgatcc acatttgctg gaaggt                                     26

<210> SEQ ID NO 18
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Wherein Xaa at position 4 is Tyr or Phe
<220> FEATURE:
<221> NAME/KEY: MISC_FEATURE
<222> LOCATION: (7)..(7)
<223> OTHER INFORMATION: Wherein Xaa at position 7 is Asp or Glu
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Wherein Xaa at position 16 is Asp or Glu

<400> SEQUENCE: 18

Asn Xaa Gly Xaa Asp Asp Xaa Asn Xaa Asp Tyr Xaa Xaa Xaa Xaa Xaa
```

```
<210> SEQ ID NO 19
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein Xaa at position 2 is Asp or His
<220> FEATURE:
<221> NAME/KEY: MISC_FEATURE
<222> LOCATION: (9)..(9)
<223> OTHER INFORMATION: Wherein Xaa at position 9 is His or Tyr
<220> FEATURE:
<221> NAME/KEY: MISC_FEATURE
<222> LOCATION: (13)..(13)
<223> OTHER INFORMATION: Wherein Xaa at position 13 is Lys or Arg
<220> FEATURE:
<221> NAME/KEY: MISC_FEATURE
<222> LOCATION: (14)..(14)
<223> OTHER INFORMATION: Wherein Xaa at position 14 is Asn or Ser

<400> SEQUENCE: 19

Asn Xaa Gly Tyr Asp Asp Asp Asn Xaa Asp Tyr Ile Xaa Xaa Gly Glu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Wherein Xaa at position 7 is Asp or Glu
<220> FEATURE:
<221> NAME/KEY: MISC_FEATURE
<222> LOCATION: (10)..(10)
<223> OTHER INFORMATION: Wherein Xaa at position 10 is Asp or Ser
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Wherein Xaa at position 14 is Pro or Leu
<220> FEATURE:
<221> NAME/KEY: MISC_FEATURE
<222> LOCATION: (15)..(15)
<223> OTHER INFORMATION: Wherein Xaa at position 15 is His or Gly or Arg

<400> SEQUENCE: 20

Asn Xaa Gly Tyr Asp Asp Xaa Arg Gly Xaa Tyr Xaa Val Xaa Xaa Asp
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein Xaa at position 2 is Asp or Asn
```

```
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Wherein Xaa at position 11 is Tyr or Leu
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Wherein Xaa at position 16 is Asp or any
      naturally occurring amino acid

<400> SEQUENCE: 21

Asn Xaa Gly Xaa Asp Asn Glu Asn Xaa Asp Xaa Ile Xaa Val Asn Xaa
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Wherein Xaa at position 8 is Asp or Glu
<220> FEATURE:
<221> NAME/KEY: MISC_FEATURE
<222> LOCATION: (10)..(10)
<223> OTHER INFORMATION: Wherein Xaa at position 10 is Asn or Asp
<220> FEATURE:
<221> NAME/KEY: MISC_FEATURE
<222> LOCATION: (12)..(12)
<223> OTHER INFORMATION: Wherein Xaa at position 12 is Asn or Pro
<220> FEATURE:
<221> NAME/KEY: MISC_FEATURE
<222> LOCATION: (16)..(16)
<223> OTHER INFORMATION: Wherein Xaa at position 16 is Ser or Ala

<400> SEQUENCE: 22

Asn Arg Thr Gly Phe Glu Glu Xaa Lys Xaa Phe Xaa Val Leu Asn Xaa
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Wherein Xaa at position 10 is Asp or Glu
<220> FEATURE:
<221> NAME/KEY: MISC_FEATURE
<222> LOCATION: (11)..(11)
<223> OTHER INFORMATION: Wherein Xaa at position 11 is Phe or Leu
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Wherein Xaa at position 16 is Ser or Thr
```

```
<400> SEQUENCE: 23

Asn Arg Thr Gly Phe Glu Glu Asn Lys Xaa Xaa Pro Val Xaa Asn Xaa
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein Xaa at position 2 is Arg or Lys
<220> FEATURE:
<221> NAME/KEY: MISC_FEATURE
<222> LOCATION: (10)..(10)
<223> OTHER INFORMATION: Wherein Xaa at position 10 is Asp or Glu
<220> FEATURE:
<221> NAME/KEY: misc_feature
<222> LOCATION: (14)..(14)
<223> OTHER INFORMATION: Xaa can be any naturally occurring amino acid

<400> SEQUENCE: 24

His Xaa Thr Gly Phe Glu Glu Ser Lys Xaa Phe Pro Arg Xaa Gly Asp
1               5                   10                  15
```